United States Patent [19]
Husseiny et al.

[11] Patent Number: 5,692,029
[45] Date of Patent: Nov. 25, 1997

[54] DETECTION OF CONCEALED EXPLOSIVES AND CONTRABAND

[75] Inventors: Abdo A. Husseiny, LaPlace; Edwin D. Stevens, New Orleans; Zeinab A. Sabri, LaPlace, all of La.

[73] Assignee: Technology International Incorporated, LaPlace, La.

[21] Appl. No.: 467,983

[22] Filed: Jun. 6, 1995

Related U.S. Application Data

[62] Division of Ser. No. 341,139, Nov. 16, 1994, abandoned, which is a continuation of Ser. No. 4,858, Jan. 15, 1993, abandoned.

[51] Int. Cl.⁶ .................................................. G01N 23/201
[52] U.S. Cl. ........................................ 378/88; 378/86
[58] Field of Search ................................ 378/86, 88

[56] References Cited

U.S. PATENT DOCUMENTS

| | | |
|---|---|---|
| 3,678,278 | 7/1972 | Peil . |
| 3,832,545 | 8/1974 | Bartko . |
| 3,919,467 | 11/1975 | Peugeot . |
| 3,924,064 | 12/1975 | Nomura et al. . |
| 3,982,125 | 9/1976 | Roder ................................ 378/186 |
| 4,004,212 | 1/1977 | Wortman ............................. 378/86 |
| 4,031,545 | 6/1977 | Stein et al. . |
| 4,047,035 | 9/1977 | Denhoven et al. . |
| 4,137,567 | 1/1979 | Grube . |
| 4,139,771 | 2/1979 | Dennhoven et al. . |
| 4,216,499 | 8/1980 | Kunze et al. . |
| 4,251,726 | 2/1981 | Alvarez . |
| 4,357,535 | 11/1982 | Haas . |
| 4,363,965 | 12/1982 | Soberman et al. . |
| 4,379,348 | 4/1983 | Haas et al. . |
| 4,469,623 | 9/1984 | Danielson et al. . |
| 4,539,648 | 9/1985 | Schatzki . |
| 4,599,740 | 7/1986 | Cable . |
| 4,759,047 | 7/1988 | Donges et al. . |
| 4,783,794 | 11/1988 | Dietrich . |
| 4,788,704 | 11/1988 | Donges et al. . |
| 4,799,247 | 1/1989 | Annis et al. . |
| 4,809,308 | 2/1989 | Adams et al. . |
| 4,817,121 | 3/1989 | Shimizu et al. . |
| 4,854,163 | 8/1989 | Mount . |
| 5,007,072 | 4/1991 | Jenkins . |
| 5,022,062 | 6/1991 | Annis . |
| 5,091,924 | 2/1992 | Bernbach et al. . |
| 5,097,494 | 3/1992 | Pantelleria et al. . |
| 5,307,272 | 4/1994 | Butler et al. ............... 364/424.02 |

FOREIGN PATENT DOCUMENTS

| | | |
|---|---|---|
| 0218240 | 4/1987 | European Pat. Off. . |
| 2934966 | 3/1981 | Germany . |
| 1550887 | 8/1979 | United Kingdom . |
| 1566256 | 4/1980 | United Kingdom . |

*Primary Examiner*—Craig E. Church
*Attorney, Agent, or Firm*—Sixbey, Friedman, Leedom & Ferguson, PC; Gerald J. Ferguson, Jr.; Donald R. Studebaker

[57] ABSTRACT

The invention is a detector for detection of concealed explosives, drugs and contraband using x-rays imaging and powder pattern techniques and ultrasonics. In case of inspection of carry-on baggage a combination of computer-aided x-ray transmission imaging and x-ray diffraction analysis is used to screen; confirm and localize threats. The x-ray transmission is used to segregate dense baggage and cargo which are inspected by x-ray backscatter imaging to identify suspicious objects. All suspicious objects are carefully analyzed by x-ray diffraction. In another embodiment a slow processing system uses diffraction for identification of threats and x-ray radiography for localization of the objects. In case of drugs concealed in compartments aboard marine vessels or air crafts a hand-held x-ray system is disclosed which can be used in three modes of operation: x-ray transmission, x-ray backscatter, or x-ray diffraction dependent on the architecture of the compartment. In case of buried mines an oscillating dual-energy x-ray backscatter imaging is used for antipersonnel mines and a combination of x-ray backscatter imaging and prompt gamma detectors is used for antivehicle and antiaircraft mines. Ultrasonic detectors are disclosed for detection of explosives on persons. Also, a tracking system based on bar-code identification system and a central computer is disclosed for baggage.

10 Claims, 46 Drawing Sheets

120 OR 160 kV

SMALL RC TIME CONSTANTS

100 μs

160kV

120kV

DETECTION OF CONCEALED EXPLOSIVES AND CONTRABAND

This is a Divisional application of Ser. No. 08/341,139, filed Nov. 16, 1994 which is a continuation of Ser. No. 08/004,858, filed Jan, 15, 1993, both now abandoned.

BACKGROUND OF THE INVENTION

1. Field of the Invention

The invention relates generally to a non-vapor system for detection of concealed contraband including: all types of explosives or drugs in carry-on baggages and hand-held items; contraband in checked-in baggage and air cargo as well as freight containers; explosives carried by individuals across a security check point, drugs concealed in hidden compartments aboard planes, leisure boats, or ships; and buried explosive-filled ordnance such as antipersonnel, anticraft, and antivehicle mines.

2. Background of the Invention

Shadowgraphs based upon radiographic imaging are currently in use for detection of explosives in carry-on baggage and articles in airports and at some security points at the entrance of secured buildings. Existing radiographic imaging provides low contrast images which are inadequate specially in identification of state-of-the-art explosives, weapons, and drugs. Plastic and water-based explosives may escape present interrogation capabilities. Reliance on humans in interpretation of radiographic displays is subject to the influence of a basic human trait which is temporal variability in response to stimuli. Such human factors may be compensated for when baggage interrogation results in high rate of false alarms. However, misses can defeat the whole objective of screening. As an interrogation device, shadowgraphs and line scanners are only useful as a deterrence to casual threats. This is aside from the fact that it is by far the least expensive and the most informative device in the market.

Due to the inadequacy of shadowgraph interpretation, airlines have instituted, in some international airports, their own search team as a second level of defense although radiographic screening, frisking, and visual screening are employed extensively in such airports. The process is usually a cause of delay and annoyance to passengers. Also, training security operators on handling explosives can be costly and would require special skills. Furthermore, the possibility of misses due to difficulty in visual recognition of a threat will remain a source of concern. Although airport baggage interrogation can be accomplished in principle, by automated conveyers and microprocessors, human involvement provides an additional level of deterrence.

Premeditated actions and advanced explosives technology and camouflage can possibly defeat existing screening arrangements. Also, screening stations are vulnerable to sabotage and can be a target for terrorist actions since suspected baggages are screened in the same spot as baggages containing benign objects. Apprehension of terrorists around the screening station and the procedure of inspection can expose innocent passengers to high risk. Generally, manual search of suspicious carry-on baggage or personal articles at security checking points involves an element of risk to operators, innocent individuals, passengers, or passers-by since accidental or inadvertent engagement of an explosive charge cannot be dismissed.

At security check points at airports or critical installations, screening of individuals for concealed explosives and contraband, using metal detectors, goes hand in hand with screening carry-on baggage. Existing metal detectors are not adequate for advanced plastic explosives and the potential spread of plastic guns. X-rays cannot be used on people due to the danger of ionizing radiation. Regardless of the level of exposure, the produced effects are undesirable. The use of sniffers employed in many security systems are likely to have low detection probability for military explosives and new water gel explosives, and hermetically sealed objects can defeat the whole detection system. A non-breachable security point will ultimately involve a system combining at least two techniques including sniffers (gas chromatography), metal detection, acoustics, etc. The redundancy provides a high confidence of establishing a hard-to-breach barrier against terrorists and illegal traffic of explosive and contraband.

Accordingly, there is a need in the art for: a cost-effective, integrated system for screening carry-on baggages and individuals at security check points which are not limited to vapor detection, which overcome the limitations of currently used shadowgraphs and metal detectors and accurately detect typical charges of various types of explosives concealed in carry-on baggage and on individuals, and which may operate as a stand alone system or work in concert with existing systems; a system for enhancement of shadowgraphs by adequate computer-aided detection especially in image processing and interpretation, to provide the viewer with proper cues, and to strengthen the security measures for casual and premeditated threats without significant changes in existing systems and without the need for modification of procedures or additional training of attendants of security terminals; a means to replace or minimize manual search of suspicious articles and carry-on baggage by a means of identification and a means of localization of threats; and a reliable system for detection of concealed explosives and explosive-filled ordnance carried by individuals at security check points, especially in airports, public and government buildings, and critical installations.

Additionally, the magnitude of destruction from detonation of explosives concealed in checked-in baggage and air cargo would be of immeasurable consequence in terms of loss of lives and irreparable economical damage. Nevertheless, concealment of explosives in checked-in baggage and air cargo is believed to have a low likelihood due to exposure of terrorists, if on-board, to risk without having the bargaining power that they may have if the explosives are at hand. In case the threat is flown separately, the only objective would be destruction without the associated publicity of a cause and demands. However, the inadequacy of tracking checked-in baggage and associating each piece of luggage to a passenger on board allows for flying a threat without a risk to the terrorist. Recent events do not dismiss potential problems since explosives can be implanted in checked-in baggage without the associated passenger being on board or a threat can be unwittingly checked-in by an innocent passenger for someone else. Also, isolated suicidal acts and criminal intentions cannot be discounted. Furthermore, the damage of a single incident would have an extensive toll on lives in addition to the psychological, political, and economical impacts.

Existing radiographic imaging approaches and vapor detection systems are not adequate for dense items even with the use of hard x-rays, since dense checked-in baggage and air cargo are the most difficult to interrogate using x-ray transmission systems. Also, the use of nuclear and neutron systems poses problems of potential damage to the content of the baggage or cargo, of lack of public acceptance, of the need for extensive training, and of high implementation costs.

Furthermore, current tracking system used by most airlines allows an opportunity for boarding a checked-in baggage without the associated passenger. Due to the huge number of passengers and baggage being transported via airborne vessels, the task of physically keeping track of individual passengers along with their baggage as they progress through their flight schedule is becoming rather tedious, inadequate and manpower intensive. This is in addition to an increasing potential of breach of security barriers, loss of revenue, and the additional costs incurred in locating misplaced luggage. Recurring events have shown that separation of a passenger from his/her baggage can lead or encourage implantation of explosives and contraband in the often unidentified pieces of luggage which may not be traced to a particular traveler. The inadequacy of checks and the increased rate of omission and commission of errors in the existing tracking system can lead to disruption of the flow of an important portion of the public transportation system and exposure of innocent lives to undue risk.

A computer-aided scheduling and management system has been broadly applied by airline companies, travel agencies, and airports for many years. However, the existing systems are only restricted to static modes of operation; such as information, ticketing, reservation, schedule planning, and flight confirmation. Most of the functions whether done manually or via computers are human intensive and subject to inadvertent or intentional diversion and human errors. of the utmost importance, the present system fails to cope with the dynamically evolving nature of air transport. Keeping track of the dynamics of the movement of airborne passengers and baggage is especially critical with the increasing complexity in situations of heavy air traffic.

Increasing air travel loads with no changes in personnel leads to a high-demand on upgrading concepts of further automation in airport operations. Existing computer facilities; such as "The Official Airline Guide (OAG)" have the capabilities of connecting individual passenger's personal computer to the central information database through a telephone call and a modem. For example, the "Travelshopper" of TransWorld Airlines, and "Easy Sabre" of American Airlines are developed for automated ticket reservation and confirmation. However, all these computer functions provide only the service of static information which cannot ensure or assist in monitoring and verification of the passenger's trip flow. Hence, means for physical tracking of flow of each individual passenger and the accompanying baggage are lacking. Such shortcomings do affect air travel security and anticipated services.

Accordingly, there is a need in the art for a system to track checked-in luggage and a non-vapor, non-nuclear means capable of screening dense baggage and air cargo for detection of typical charges of several pounds of concealed state-of-the-art explosives which may escape existing interrogation capabilities.

Drugs such as cocaine or heroin (as well as designer drugs) are often smuggled in concealed compartments as well as in the open environment aboard marine vessels and aircrafts. The Coast Guard boarding parties are often unable to discriminate between innocent and suspicious compartments during the search of suspected craft in known drug trafficking areas. This is partially due to lack of the necessary and sufficient evidence prior to opening a compartment to avoid unsubstantiated destruction of an area of the vessel or the craft.

Accordingly, there is a need in the art to provide a system for non-destructive remote inspection for use in interdiction of drugs on marine vessels and aircrafts.

Historically, mines and hidden explosive devices have proven to be of significance in both low and high intensity conflicts. Mines destroyed over twenty five percent of the vehicles in World War II. That percentage almost tripled (nearly seventy percent) in Vietnam. The associated loss of personnel makes improvements in countermine technology imperative. Mines come in a wide assortment; including a variety of explosives, whether as primary or secondary charges. Some of the most common explosives are TNT, Amatol, composition B or composition C. Fuzing techniques include pressure, seismic, anti-disturbance, magnetic, trip line or a combination as well as command operated. Casings include metallic or nonmetallic (plastic). Burial depth varies between surface laid and buried. In spite of the vast development in warfare technology, the state-of-the-art for detection of mines and buried explosive devices lag behind. Though, mines have been a major contributor to the increasing lethality of the battle field, current mine detection devices are based on simple but outmoded technologies that lack accuracy in detection. They involve either manual probing or the use of metal detectors. Both methods are manpower intensive, slow and leave human operators exposed to a fire coverting. Misses in detection are not tolerable and false alarms tend to lower the confidence in the whole device and leads to major errors.

Accordingly there is a need in the art for a detection system capable of real time operation at normal troop advance rates, with high detection/false target ratios, and with sufficient standoff to allow foot soldiers or carrying vehicles or aircrafts to avoid engaging a detected mine.

Additionally, a highly dependable detector for mines in combat fields may require the use of two technologies for verification, for elimination of false alarms, and for versatility in application in various situations, such as soil/water coverage, metal/non-metal casings. Accordingly, there is a need in the art for a dual system especially designed for variable combat conditions.

U.S. Pat. No. 4,251,726 (Luis W. Alvarez) relates to deuterium tagging in an mount at least ten (10) times the natural abundance of the deurerium isotope occurrence and to a method of detecting the tagged article, such as explosives concealed in airline luggage includes subjecting tagged compounds with energy quanta sufficient to carry out the reaction D→n+p–2.23 MeV and detecting the number of neutrons generated where n is a neutron, p is a proton and 2.23 MeV is the threshold energy required for the reaction. The apparatus includes a conveyor and a vertically scanning shutter in combination with a linear accelerator for generating the x-ray energy in the order of 4 MeV and a boron trifluoride proportional counter for detecting neutrons. Also, U.S. Pat. No. 3,114,832 (Luis W. Alvarez) relates to the use of x-ray technique to detect Barium tagging. Furthermore, U. S. Pat. No. 4,469,623 (Richard D. Danielson and Robert A. Prokop) relates to detection of articles by the use of vapor-permeable microcapsules containing perfuloralkyl bromides as tags for explosives to permit detection of the articles by a gas- electron-capture detector, and U.S. Pat. No. 4,363,965 (Robert K. Soberman, Kenneth Dervitz, Louis L. Pytlewski) relates to a detection/identification method for determining the presence of a Moessbauer isotope-containing taggant in explosives, weapons, currency, tax stamps, identification documents, etc. The detector includes a Moessbauer isotope-containing detecting substance that is identical to the taggant, and a sensing element responsive to the presence of the tagging substance in the carrier material, provided that the Moessbauer isotope of the tagging substance is in a state of resonance excitation and causes excitation of the Moessbauer isotope of the detecting substance.

None of these references teaches the identification of concealed articles without tagging. Tagging explosives or detonator is impractical when dealing with terrorists who have access to variety of explosives produced under uncontrolled conditions and home made explosives.

Great Britain Patent No. 1,566,256 (Anthony Jenkins, Douglas Walter Issrove) relates to a method and apparatus for detecting a constituent in an atmosphere, especially for revealing nitro explosives by detection of emitted vapors. The apparatus comprises two flow paths each containing an electron capture detector and having a common sample inlet, means in one flow path for altering the flow time of the particular constituent, an indicator for receiving a signal path from the detector in that path, and an isolator in the signal path for preventing passage of a signal in the absence of the constituent. This cited reference teaches identification of explosives in case of release of vapor but does not teach detection of hermetically sealed explosives.

Great Britain Patent No. GB 2,057,135 (William Lloyd Rollwitz, James Darwin King, George Andrew Matzkanin) relates to quick screening of suspect letters and packages for the presence of explosives by placing in a holder inside a coil between the poles of a magnet which exerts a constant magnetic field while the coil exerts a pulsed radio-frequency magnetic field orthogonal to the constant magnetic field. U.S. Pat. No. 2,934,966 (James Darwin King, George Andrew Matzkanin, William Lloyd Rollwitz) relates to an apparatus and method for detecting explosives by nuclear magnetic resonance materials suspected of containing explosives are exposed to a constant magnetic field and an impulse modulated magnetic high-frequency field perpendicular to the constant field. The methods in both patents do not teach the art of detection of baggage without the potential damage of content and the interference from the presence of metallic objects. The magnetic field can destroy watches and jewelry.

U.S. patent application Ser. No. 847,425 the U.S. counterpart of French Patent 2,433,187 (William O. Gregory, Larry H. Capots, Luigi Morelli, John Mulke, III, Thomas A. Nolan, Jr.) relates to electrical circuits for identification of materials in heterogeneous systems, for example explosives in envelopes and parcels using their complex characteristics of dielectric response. The method does not teach the art of detecting various types of explosives, especially those having metallic casing.

Great Britain Patent No. 1,550,887 (Bain Griffith) relates to an apparatus and method for detecting explosives in closed suitcases or packages by irradiating the case with thermal energy neutrons at 0.01–0.1 eV/neutron and measuring the number of neutrons transmitted to determine the amount of nitrogen in the case, irradiating with 106 eV/neutron to convert oxygen to nitrogen-16 which is measured by a Geiger Counter, and comparing the two measurements to determine whether the proportions of nitrogen and oxygen indicate the presence of explosives. A display device is described for a 2-dimensional image useful for scanning luggage to be loaded onto an aircraft.

French Patent No. 2,588,969 (Gerard Grenier) relates to a device for the detection of substances such as explosives and comprises a generator of preferably 14 MeV neutrons for passage through an object suspected of containing an explosive, a Ge detector, and an analysis means coupled to the detector for analysis of the gamma-rays emitted by the object. The nitrogen-oxygen ratio of the object is determined and compared to that for known explosives.

None of these references cited teaches the specific identification of concealed articles by characterization of the chemical and physical composition of explosives using non-vapor and non-nuclear means. Further, none of the references noted hereinabove teaches the use of x-rays for the detection of explosives in baggages.

European Patent No. 0218240 (Luis W. Alvarez) relates to an apparatus and method of detection including using a 40 MeV (or higher energy) x-ray source as a narrow beam emanating from a microtron. Irradiation of nitrogen with high energy x-rays produces 511 keV annihilation radiation from the decay of an exceedingly short-lived isotope of nitrogen reaction 14N (x-rays, gamma, 2n) $12_N$ where N is a nitrogen, n is a neutron. The apparatus detects concentrations of nitrogen between 20% and 30% by weight such as is common in explosives. The apparatus uses high resolution imaging to determine nitrogen content in each two inch cube of the bag's volume in two seconds with the ability to re-examine in 16 seconds Nitrogen concentrations and consequently expected concealed explosives are easily mapped in two or three dimensions quantitatively. The method has the disadvantages of false alarms, large size, high cost and the potential escape of exotic nitrogen-free explosives from detection.

U.S. Pat. No. 4,817,121 (Hiromu Shimizu; Isao Horiba) relates to an apparatus for checking baggage with x-rays utilizing an x-ray source for irradiating x-rays toward an object to be checked on a conveyor with a fan-shaped beam, an x-ray detector including a plurality of detecting elements aligned along each of two arms of an L-shape arranged so that one arm extends substantially parallel and another arm extends substantially perpendicularly to a conveying surface of the conveyer means with the detecting elements providing electrical signals in proportion to intensity of the detected x-rays passed by and through the object as measured data, and a picture processor for converting the measured data into a picture signal for display on a display device. The picture processor includes a distortion correcting circuit for processing the measured data from the L-shaped x-ray detector so that the measured data corresponds to data obtained by detecting elements arranged along one straight line.

U.S. Pat. No. 4,799,247 (Martin Annis; Paul J. Bjorkholm) relates to an x-ray imaging device for increasing the ability to recognize, in x-ray produced images, materials of low atomic number. A flying spot scanner illuminates an object to be imaged in a raster pattern; the flying spot repeatedly sweeps a line in space, and the object to be imaged is moved so that the illuminating beam intersects the object. At least a pair of x-ray detectors are employed, each pair associated with signal processing apparatus and a display. The two detectors employed (and the associated electrons and display) are selected from a set of three which includes a transmitted detector located at the line in space which is repeatedly traversed by the pencil beam, a forward scatter detector which is located further from the x-ray beam than the object to respond to photons scattered by the object being illuminated out of the path of the beam, and a backscatter detector which is located closer to the x-ray source than the object being imaged and also arranged to detect photons scattered out of the beam path by the object. Also set forth in the above referenced patent, all three detectors and their associated electronics/displays are employed.

U.S. Pat. No. 4,788,704 (Gerhard Donges; Cornelius Koch) relates to an x-ray scanner and detector signal processing system for scanning objects moving on a conveyor path and for processing the detector signals acquired by the scan has a comparator for identifying faulty signals, the comparator being in a control chain for an image storage memory such that, in the event of a faulty detector signal, the contents of a memory row preceding the faulty detector signal are transferred into the memory row into which the faulty detector signal, if a correct signal, would have been stored. The system also includes a correction element for generating a reference signal at 100% radiation intensity in which the mean value of a number of measured signals is formed. The system also includes an element for reducing the amplitude of the useful signal during measurement in comparison to the amplitude allocated to a radiation intensity of 100%.

U.S. Pat. No. 4,783,794 (Rolf Dietrich) relates to a baggage inspection system has a conveyor path disposed between an x-ray source, which generates an x-ray beam, and a radiation detector for detecting radiation passing through articles on the conveyor path. The conveyor path is formed by two surfaces disposed at a fight angle being inclined relative to the horizontal so that articles on the conveyor path are forced by gravity to lie against one of the surfaces. At least one of the surfaces is a moveable surface, and the other surface may also be a moveable surface, or a roller surface or a plate against which the articles slide. The radiation detector may be an angled detector row so as to encompass substantially all of the radiation beam within its field of view. U.S. Pat. No. 4,759,047 (Gerhard Donges; Rolf Dietrich) also relates to a baggage inspection system has a conveying path for moving articles to be inspected through an x-ray beam. The conveyor path is disposed between an x-ray source for generating the beam and a radiation detector. The radiation detector consists of a number of individual detectors, with the number of individual detectors per unit length being greater in a first region of the detector than in a second region thereof. The first region is disposed at the level of the conveying path for optimally displaying the smaller articles transported by the conveyor path, while the second region is suited for display for larger articles.

U.S. Pat. No. 4,599,740 (Arthur P. Cable) relates to a radiographic examination system for performing x-ray examination of large items such as International container units is formed as an installation comprising housings for one or a plurality of x-ray sources such as linear accelerators which in operation transmit a continuous beam of radiation across a conveyor along which the units to be inspected are displaced either continuously or incrementally. The radiation transmitted through a container is detected in a folded sensor screen or array extending on one side and over the position occupied by a container under inspection. The sensor screen or array produces optical signals which are converted into electrical signals by a photo-diode array or a camera system such as a television camera, and transmitted as pulse coded electrical signals by a coding transfer unit to display screens and signal recording equipment where an image of the transmitted information can be displayed and/or recorded for further use.

U.S. Pat. No. 4,539,648 (Thomas F. Schatzki) relates to detection of agricultural contraband in baggage using a radiant energy imaging system for selectively enhancing the image of objects having rectangular cross section, such objects being contained in a material having a different density-absorption coefficient product than the objects. In the invention, the gradient image of the spatially resolved transmitted intensity of the radiation is calculated and eroded to preferentially remove the edges of images of objects having rectangular cross section. The invention finds particular use in detecting agricultural contraband contained in baggage or parcels.

U.S. Pat. No. 4,379,348 (David J. Hass; Costas Blionas; Joseph P. Muenzen) relates to x-ray security screening system involving an optical magnification system for viewing magnified portions of articles being inspected in x-ray examination systems. A combination of a full screen lens and at least one magnification lens are provided for variously inspecting the entire article or only suspicious pans thereof.

U.S. Pat. No. 4,357,535 (David J. Haas) relates to an apparatus for inspecting hand-held articles and persons carrying same. The inspection system is provided to simultaneously x-ray inspect hand carried articles and provide metal detection of the person of the carder. These different inspections are independent, and may be carried out separately from one another. The x-ray inspection involves the insertion of a hand carried item into a chamber, and guiding it along the x-ray inspection station by holding a handle outside of the detector. Metal detection of the person may be accomplished independently by walking through a metal detector arch.

U.S. Pat. No. 4,137,567 (Hans J. Grube) relates to a system for processing passengers and their luggage at civil airports including a passenger processing counter for verifying airline tickets and confirming passenger identity, equipment for conveying large luggage to be separately stowed aboard the plane from the counter to the plane and installations for performing a security check of both the passengers and their hand or cabin luggage. The system is characterized by a movable conveyor belt extending from the passenger passageway for lined-up passengers and the counter in close proximity thereto but inaccessible to the passengers from the station for passenger processing to a point of pickup and handling by secure airport personnel. A passenger security check zone is provided for allowing a security check of the individual passengers and is designed in a manner of a one-way gate for allowing a security check of the individual passengers and is designed in the manner of a one-way gate for allowing only one-way travel of passengers through the passenger passageway from a point immediately following the passenger processing station through to a verification zone which immediately follows the security check zone and where a passenger becomes cleared by the system. A second movable conveyor belt is provided on the opposite side of the passenger passageway and starting immediately prior to the security check zone for the passengers. The second conveyor belt provides a security check of the hand or cabin luggage of the passengers and terminates behind the verification zone. The second conveyor belt is inaccessible to passengers while they are passing through the passenger security check zone and becomes accessible to particular and already cleared passengers so that they may retrieve their security checked hand or cabin luggage after passing through the security check zone and upon reaching the verification zone.

U.S. Pat. No. 3,924,064 (Yasuji Nomura; Koichi Koike; Kazuo Yamamoto) relates to an x-ray inspection apparatus for baggage whereby generating an x-ray image of an object is disclosed. X-rays are radiated to the object in the form of pulses, and the image is converted to a video-signal for one field and recorded. The recorded video-signal is repeatedly regenerated at field cycle until a next video-signal is produced. In such as system, inspection may be made while the object is being rapidly transferred at an extremely low x-ray radiation level. U.S. Pat. No. 3,919,467 (Ridge Instrument Company, Inc.) relates to an x-ray baggage inspection system in which an x-ray generator directs a beam through an object of baggage and the resulting image, appearing on a fluorescent screen, is scanned by a low light level TV camera and the image stored, the generator being turned on for a selected number of TV scans or frames. The number of frames and thus the intensity of image accumulated and stored in a video scan converter, is controlled by the operator to enable only the radiation exposure necessary to obtain a legible TV image, the image being displayed on a TV monitor.

Westinghouse Research and Development Center (J. R. Schneeberger and W. C. Divens), Pittsburgh, Pa., describes a rapid screening system for airline passenger baggage for explosives using x-ray contrast profiles. The system employs a Ba-133 isotope as the irradiating source and a linear array of scintillation detectors which are sequentially scanned to obtain independent x-ray detection values for each resolution element over the entire bag profile area. Data is digitized and a real-time connectivity analysis is made by an on-board computer to establish the size of each separate object at the same or greater contrast. An alarm is sounded whenever any object exceeds the minimum size associated with the threat object at its detection threshold. Throughput time is such that bags can be screened at the rate of one/second. The system was evaluated through tests at several airports in which nearly 6000 airline passenger bags were screened to obtain their shape/detector profiles.

IRT Corp (Hans J. Weber), San Diego, Calif., disclosed an automated high speed letter bomb detector system as a self-contained unit which combines the high processing throughput rates of modern mail-handling equipment with fully automated mail screening using remote sensing radiometric gaging techniques, real-time data processing, and automated decision implementation. Three nuclear gages are integrated into a multiparameter sensor capable of discriminating between explosives and paper on the basis of a determination of deuterium concentration and of the ratio of high-Z versus low-Z element constituents. The resulting explosives detector determines the presence of explosives in less than 100 ms in letter mail. This rapid detection capability is achieved by optimizing sensor technology and geometry to the case of letter mail. As a consequence, the sensor is specialized for letter mail with a limited application for other uses.

Aerospace Corp (Fredrick L. Roder), Washington, D.C., discloses an explosives detection method using dual-energy computerized tomography wherein the numerical reconstruction of a cross-sectional image of an object from a data set consisting of the line-integral projections of that cross section obtained at different aspect angles is utilized. The adaptation of dual-energy CT to the detection of relatively small amounts (approximately 100 g) of any of a broad spectrum of explosives concealed in suitcases and packages was shown.

The Bechtel CARGOSCAN™ system developed in collaboration with American Science and Engineering, Inc. using a Varian Associates, Inc. Linatron disclose a hard transmission x-ray system capable of penetrating a ten (10) inch of steel to detect a hidden pistol.

U.S. Pat. No. 4,139,771 (Manfred Dennhoven; Claus Kunze; Rainhard Kuehn) relates to a luggage inspection apparatus utilizing fluoroscopic examination in conjunction with an x-ray generator, with the fluoroscopic picture being received by a TV camera, the video signals of which are supplied to an intermediate store for ultimate supply to a TV monitor, the camera containing an AC line-coupled pulse generator for synchronizing the camera and the x-ray flash generator, which pulse generator is electrically interconnected with a synchronizing unit which, upon the initiating of a starting pulse, thus likewise synchronously triggers the x-ray flash generator with respect to the AC supply line. Also, U. S. Patent No. 4,047,035 (Manfred Dennhoven; Claus Kunze, Rainhard Kuehn) relates to a baggage inspection apparatus utilizing an x-ray generator for fluoroscopic examination of luggage and the like in which an x-ray detector is disposed in the beam path of the x-ray generator, operative to control switch means for switching off the high voltage of the x-ray beam generator in the event the intensity and/or duration of the x-ray radiation exceeds a predetermined value.

U.S. Pat. No. 3,618,218 (Le Roy E. Pell) relates to an inspection apparatus for use with an airline ticket and check-in counter includes an x-ray and fluoroscopic examination unit and a frequency modulation monitor, all positioned on a frame adjacent a baggage weighing platform. A sliding x-ray impervious shield is supported on the frame and is positioned over the weighing platform and baggage thereon during the x-ray inspection.

U.S. Pat. No. 4,216,499 (Claus Kunze; Manfred Dennhoven) relates to a baggage inspection system utilizing fluoroscopy of baggage pieces and the like, employing an X-ray flash unit, a television pick-up unit for scanning the x-ray image, storage of the television image and subsequent image reproduction by a television monitor, in which, in accordance with the invention, the memory is a digital solid state memory for the digital storage of a half frame, of an interlaced video frame of the television pick-up unit, with a capacity of 6 to 8 bits per image-point of the image signal to be stored.

However, Science applications international corporation (SAIC), Sunnyvale, Calif. (Richard I. Miller, Gaynor L. Abbott, Sylvia A. Davey, Peter T. Smith) disclose an evaluation of x-ray fluorescence detectors which are presently available for detecting concealed explosives, for example in airplane luggage and cargo. The method is found to be inadequate for concealed explosives, because the areas capable of being detected are too small and the resolution at high count rates is not high enough.

When x-ray fluorescence is used to analyze a sample, the energy of the fluorescent x-rays is proportional to the atomic number of the element. Thus light elements yield very low energy x-rays which cannot penetrate the baggage, and therefore, are not detected. X-ray fluorescence is thus limited to the detection of heavy elements, such as the lead in detonators. In contrast, when x-ray diffraction is used for the analysis, the scattered x-rays have the same energy as the probe beam. Thus, highly penetrating short wavelength x-rays may be used to probe highly absorbing materials. In addition, since each chemical compound has a characteristic pattern, not only are all elements detected, but the actual chemical compounds can be identified. The problem thus becomes one of obtaining an adequate signal to noise ratio.

Nuclear techniques have also been disclosed for mine detection including: U.S. Pat. No. 3,832,545 (John Bartko) which pertains to a nuclear technique for monitoring objects such as luggage and parcels to determine the presence of specified nitrogen containing materials such as explosives as a function of the nitrogen content and concentration profile. Objects to be analyzed to determine the presence of nitrogen are subjected to a thermal neutron environment and the gamma ray radiation produced by the object in response to nitrogen reactions is monitored by gamma ray detectors. The gamma ray detectors produce indications of the nitrogen content of the object and the concentration profile of the nitrogen in the object. The information provided by the gamma ray detectors is processed to determine if the measured nitrogen content and concentration corresponds to a class of nitrogen containing material of interest, i.e. explosives. U.S. Pat. No. 3,982,125 (Frederick L. Roder) which relates to a method and apparatus for compensating for height variations in certain nuclear gauging applications, particularly nuclear mine detection, are disclosed. A source of monoenergetic photons and a pair of detectors are provided. One of the two detectors includes a K-edge filter, whereas the second detector does not. After processing, the outputs of the two detectors are applied to a suitable readout device. The combination of the filtered detector and unfiltered detector provide a means to compensate for any height variation of the source-detector assembly above the medium under study; thereby permitting any change in the average atomic number of that medium to be discerned.

Also, improvement on existing mine detectors based on electromagnetic techniques is disclosed in U.S. Pat. No. 4,004,212 (Donald E. Wortman) which relates to a mine detector system that utilizes an explosive comparator to increase the sensitivity and selectivity. The system utilizes a generator to transmit a signal simultaneously toward the area to be scanned for mines and towards a sample of the explosive sought. Detectors are positioned within the device to receive the reflected signals from both the area to be scanned and the sample explosive. The outputs from both detectors are fed to preferably a null type comparator for correlation. When the two signals correlate, mine presence is indicated.

None of these prior art references disclose a system that utilizes a combination of low or medium energy x-ray transmission, x-ray diffraction and/or x-ray backscattering system for baggage and cargo, or an ultrasonic system for screening of individuals. Also, none of the literature cited teaches the identification of dynamite (granular, 4 percent), C-4 (Military Specs), water gel/slurry/emulsions $NH_4 NO_3$ (ammonium nitrate), sheet explosives (PETN), TNT, cocaine, and heroin. Also, none of the prior art teaches the combination of an x-ray backscattering detector and prompt gamma detector to detect antipersonnel, antivehicle or anticraft mines at an appropriate standoff.

SUMMARY OF THE INVENTION

According to the present invention, a system is disclosed for detecting explosives and other contraband at security check points, in carry-on baggage and on individuals crossing security check points. In a second aspect of the invention, a system detects explosives in dense baggage and air cargo. In a third aspect of the invention, a system detects drugs concealed in compartments and sealed closets aboard ships. In a fourth aspect of the invention a hand-held system detects antipersonnel buried explosive-filled ordnance. In a fifth aspect of the invention a system detects antivehicle and anticraft land mines at a standoff position.

It is an object of the present invention to provide an integrated security check point system for explosive detection which can work independently or in concert with other existing detection systems, and which encompasses screening of carry-on baggage and hand-held items using a combined x-ray transmission and x-ray diffraction units and screening of individuals by a walk through and/or hand-held ultrasonic imaging apparatus based on the state-of-the-art sonic/ultrasound devices to maintain a thorough, rapid and continuous screening while helping in prevention of criminal acts; using a procedure similar to that in existence in concourse while-through metal detectors or shadowgraphs in airports and security checkpoints in some buildings.

It is another object of the present invention to provide a screening system for dense checked-in baggage and air cargo for contraband and explosives using a combination of x-ray techniques and adequate tracking system.

It is a third object of the present invention to provide a detector for drugs such as cocaine and heroin hidden in concealed compartments or open environment aboard marine vessels or aircrafts.

It is a fourth object of the present invention to provide a standoff detection system for buried or hidden explosive-field ordnance whether in combat zones or in ranges of unidentified explosive locations.

It is a further object of the present invention to provide an unattended mode of operation of the screening system including automation of the detection system in a manner that allows no or minimal demand on human interface; while the role of the operators (security personnel) will be limited to vigilance tasks wherein no perception, cognition or decision-making is required.

It is a still further object of the present invention to provide an explosive detector capable of localization of a threat and capable of detection of a wide variety of explosives without being defeated by countermeasures of concealments or methods negating the effect of the detector.

It is a still further objective of the present invention to provide a screening system that meets public acceptance and that does not pose any human or economical risk.

It is a still further objective of the present invention to provide airports with an integrated tracking system for passenger/baggage tracking within airports and from flight to flight which combines the features of: a multipurpose, adaptive, computer-driven and automated system; a design based upon realistic assumptions and credible scenarios, an operation that requires minimum human intervention whether on the part of passengers or airline personnel; a capability that can be adapted to a changing pattern of air travel whether daily or seasonally, which accommodates for changes in the security measures, and which would assist the airlines in passenger boarding verification and misplaced baggage location and would accommodate for modifications in airports and changes in schedules; ease of implementation to facilitate air travel while assuring compliance with regulations and accommodating for any possible changes; and a system that can be retrofitted to present air travel systems without extensive changes or cost to both the passengers and the airlines.

It is a still further object of the present invention to provide an apparatus and a method that achieve high processing rate and detection probability, with a low percentage of false alarms at a modest cost.

It is a still further object of the present invention to provide readily interpretable signals to den the operators via alarms (sound horns, flashing/blinking light or screen) and an audio-visual output of the security system which will not require further interpretation or decision making by security personnel.

It is a still further object of the present invention to provide a screening system for which the capital cost including installation is modest and is comparable to existing detectors, and for which the operation and maintenance costs is within the range of the costs of existing systems, and for which the operation and maintenance tasks are not labor intensive.

In a first embodiment of the invention, an x-ray diffraction system is provided for thorough interrogation of suspicious baggage after preliminary inspection using an enhanced shadowgraph, and an acoustic system is provided for inspection of individuals following screening by an enhanced metal detector. Since both interrogation of carry-on baggage or articles and inspection of individuals or passengers are performed simultaneously and have to be coordinated, the function of the security check point is treated as an integral process although each task relies on separate systems.

For screening carry-on baggage, support and enhancement of the existing radiographic units is accomplished by increasing the image contrast and the use of computer assist in interpretation of the images to maintain a high processing rate. A cost-effective computer-aided enhancement to the shadowgraphs is disclosed to provide the proper cues to the viewer without significant changes in existing systems and without the need for modification of procedures or additional training of the security terminal attendants. The enhanced shadowgraph has the features of: edge enhancement, depth analysis, surface texture perception, zooming capability, contrast enhancement (for detection of plastic threats), and discrimination between a threat, suspected threat and no threat. Suspicious carry-on baggage are directed to a second screening station which involves an x-ray diffraction unit for verification and localization of the presence of a threat. Since suspicious objects are likely to represent a very small percentage of the processed baggage, delays in the x-ray diffraction can still yield the desired processing rate on the average. Also, the station where suspicious baggage is screened needs to be relatively isolated from the flow of the main screening. Readiness for seizure, disposal and apprehension can be implemented at a station located near to the second station.

The first aspect of the invention also relates to detection of concealed explosives and explosive-filled ordnance carried by individuals at security check points employing an enhanced metal detector followed by an ultrasonic detector. An alternative to the use of x-rays is the sonar scanning which has no known harmful effects on human and can provide true images. Ease of performance and relative detection accuracy provides a viable means that can complement or replace the metallic detectors which can be easily defeated by plastic guns and non-metallic explosives.

By adding an x-ray backscatter unit to the configuration of the first aspect of the invention, an arrangement can be made to segregate dense baggage from light baggage wherein the dense baggage is inspected by x-ray backscatter to localize threat and suspicious objects prior to x-ray diffraction analysis to speed up the interrogation of cargo and dense baggage in the second aspect of the invention. A piece of baggage or cargo item in which a suspicious object is located either by x-ray radiography or x-ray backscattering would be directed to the x-ray diffraction analysis station. The object would be positioned in the x-ray beam by a computer for analysis of the image. The x-ray diffraction pattern would then be collected and compared with patterns of known explosives. Alternatively, the dense baggage and cargo are interrogated by an x-ray diffraction system and a radiographic unit is used to localize threats. In both cases a baggage tracking system is provided to assure high probability of detection.

In interrogation of carry-on baggages and articles as well as dense baggage and cargo, the screening system of the present invention, utilizes x-ray diffraction unit in which a monochromatic beam of x-rays strikes the solid object to be interrogated. Microcrystals in the object are diffracted with a pattern of intensifies which are a "finger print" of the solid phase of the object. Each metal, explosive, drug compound, etc., which forms a well defined crystalline phase yields a unique diffraction pattern. Liquids and amorphous solids such as glass, wood, leather, etc., do not produce a well defined diffraction pattern. An extensive library of x-ray powder diffraction patterns, including common explosives, available from the Joint Committee of Pattern Diffraction Standards (JCPDS) is used. X-ray diffraction provides the capability of analyzing objects using powder x-ray patterns of known explosives which are readily stored in the computer. The stored patterns are continuously updated to cope with the evolution of explosives technology. Relatively high energy (short wavelength) x-rays are used, as with x-ray imaging, in order to provide sufficient penetration. As a result, the diffracted x-rays are being compressed into smaller angles of scattering in the forward direction.

The baggage tracking component of the invention comprises a cost-effective, computer-driven automated system to physically keep track of trip flow of passengers and baggage as they progress through their flight schedule within airports and also from flight to flight, if transfers are involved. This invention provides an efficient and user-friendly information service that would provide for increased security of air travel, minimize loss of revenue by improving passenger boarding verification, eliminate inconveniences and cost of locating misplaced baggage, and further the automation of airport operations without impact on current airport operations in terms of high cost, increase in manpower, or growth of demand on existing labor. Some of the features of the tracking system include: correct and accurate provision of information on passenger boarding and baggage loading; easy access to exact information on air travel flows of individual passengers and baggage; efficient updating of dynamic information in real time; user-friendly instruction and information on flight particulars at the local airport, for passengers; effectively interfacing between inter-airport and inter-company communications; automatic sort and classification of baggage during transfers; and securely tracking passengers and their baggage.

The third aspect of the invention provides a portable x-ray drug detection probe capable of detecting cocaine or heroin (as well as designer drugs) for use in interdiction of drugs on marine vessels. The x-ray source is such that the x-rays would be capable of penetrating a host of barriers of different thicknesses and construction material including wood, fiberglass, plastics and steel. The probe can be modified in-situ to provide standard x-ray radiographic imaging, x-ray backscatter imaging, or x-ray diffraction analysis or a combination thereof to provide a versatile drug detection capability for probing various configurations, geometries and arrangements of concealed compartments.

In the fourth aspect of the invention, a hand-held mine and explosives detection system is disclosed employing dual-energy x-ray backscatter imaging. The detector is provided for use in range clearance and for use by dismounted troops to detect buried antipersonnel mines. The detector is capable of real time operation, at normal troops advance rates; high efficiency; high detection/false target ratios (signal-to-noise ratio); high reliability; negligible miss incidents; and low mass and manufacturing cost. The operation provides sufficient standoff to avoid engaging a detected mine. Typical standoff ranges are 10–100 for dismounted troops, 50–500 meters for armored vehicles, and 250–2,500 meters for aircraft with the maximum as the most desirable. The detector consists of a 20 kW rotating anode x-ray generator which switches between two x-ray energies at a rate of 60 switches/second. An oscillating collimator sweeps across an area of 60 cm at a rate of 1 sweep/second, that is m forward speed of 120 cm/min can be achieved. Four scintillation detectors with an area of 20 cm$^2$ each are displaced at differing heights. Both the source and detectors will be located approximately 30 cm above the surface.

A variation on the hand held detector, is a vehicle mounted detector using an arrangement similar to the backscatter system for dense baggage screening.

For detection of antivehicle and anti-aircraft mines in sandy soils and in surf areas, a system that combines the x-ray backscatter imaging capability and a prompt gamma detection unit is provided in the fifth aspect of the invention. The x-ray backscatter imaging is suitable for locating alien objects and the prompt gamma detection unit is appropriate for identification of explosives. The x-ray backscatter unit is similar to that for the dense baggage. The prompt gamma detector uses nuclear activation techniques to specifically detect carbon, nitrogen, and oxygen. The method consists of using a pulsed Deuterium-Tritium 14 MeV neutron generator. Ten (10) microsecond neutron pulses can be produced to irradiate the objects. Materials exposed to the fast neutrons undergo inelastic neutron capture, neutron emission reactions X(n,n')X*. These reactions produce prompt high energy gamma rays on the order of 2 to 8 MeV that are characteristics of the irradiated material(s). The emitted gamma radiation is detected with large volume Bismuth Germanate (BGO) detectors. The prompt high-energy gamma rays are chosen as the measured parameters because at these energies, the true signal to noise ratio is greatly improved. In addition, the thermal neutron effects and natural background are reduced by factors of approximately 50 to 100.

The prompt gamma system explicitly depends on measuring the nitrogen content of the interrogated area. The versatility of the technique in various environments which include soil and/or water coverage, and metal or non-metal casings allows it to discriminate against false signals as the nitrogen to carbon ratio and nitrogen to oxygen ratio of the targeted area can be continuously assessed. Based on actual neutron generator and detector performance, a mine containing one (1) kilogram of explosives (30% by weight nitrogen), and buried to a depth of up to three (3) feet below soil (or water) surface can easily be detected. Field coverage rates for the detection method can approach up to one acre per hour. The conceptualized system is of moderate size and weight, and is adaptable to battlefield conditions.

DETAILED DESCRIPTION OF THE INVENTION

Figure 1:
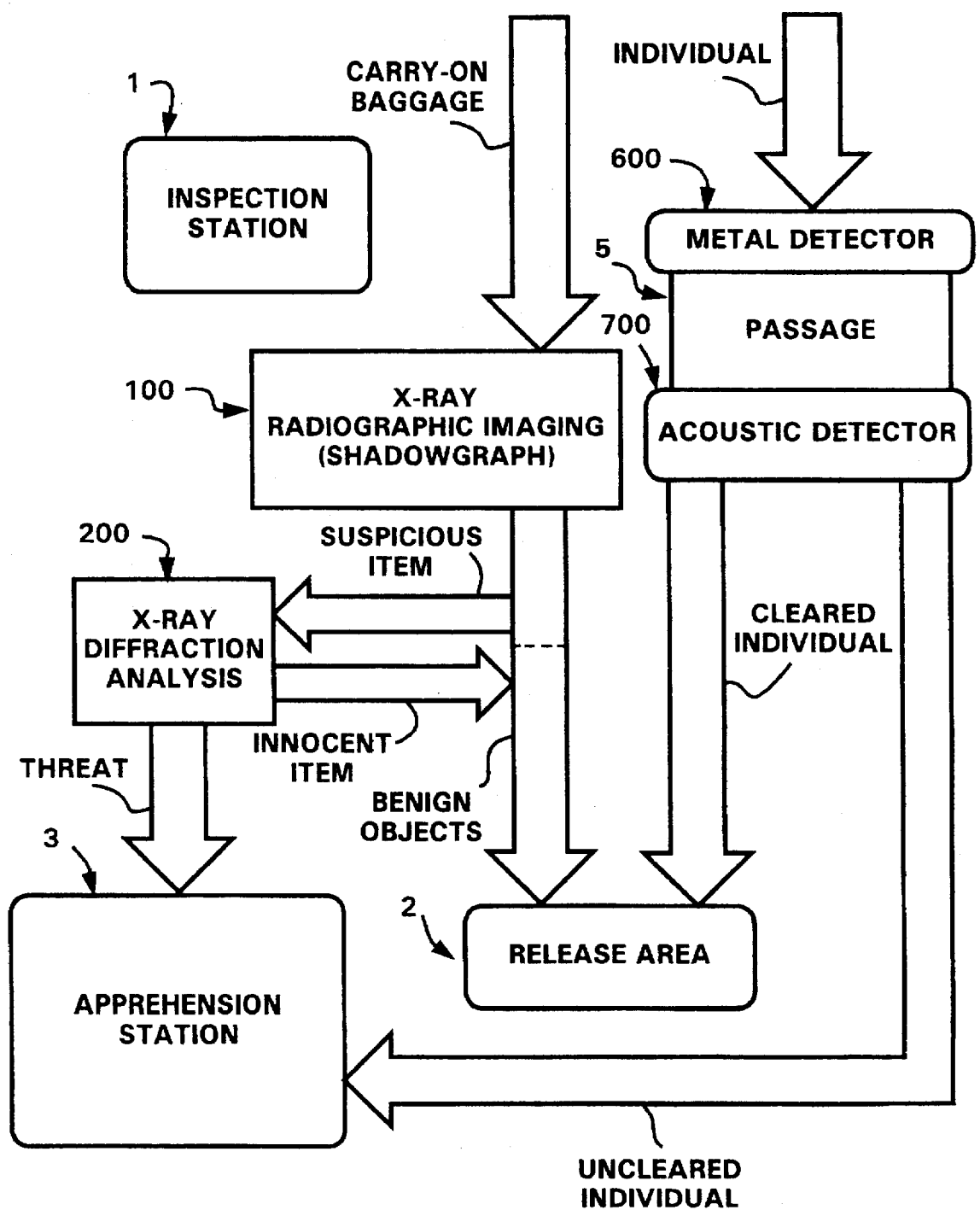
FIG. 1 shows a flowchart of the screening process at the security check point including: the improved shadowgraph and the x-ray diffraction system for explosives and contraband in carry-on baggage, and the ultrasonic detection system for detection of explosive-filled ordnance and explosives on individuals.

In the first aspect of the invention, the individual or passenger gets screened as the associated carry-on items are being processed. Both the individual and the baggage carry a similar identification which is placed on the baggage bar code as well as on an identification badge or airline ticket carried by the individual associated with the baggage. As an individual places the carry-on baggage on a conveyer, the individual screening process commences by the inspection station 1 as shown in FIG. 1. The individual is first checked by a metal detector 600. If a suspicious item is present an audio alarm will sound. Whether metal objects are present or not, the individual proceeds through a passage way to the ultrasonic system 700 to detect other forms of explosive devices and other contraband to verify the initial detection. In the case of the screening system for carry-on baggage and hand-held articles, the action unit 200 is utilized to verify suspicious items after initial examination of the carry-on baggage by an enhanced shadowgraph unit 100. Benign articles would be released at station 2, while items containing threat will be directed to an apprehension station 3, far from the passenger's or individual's reach.

Figure 2:
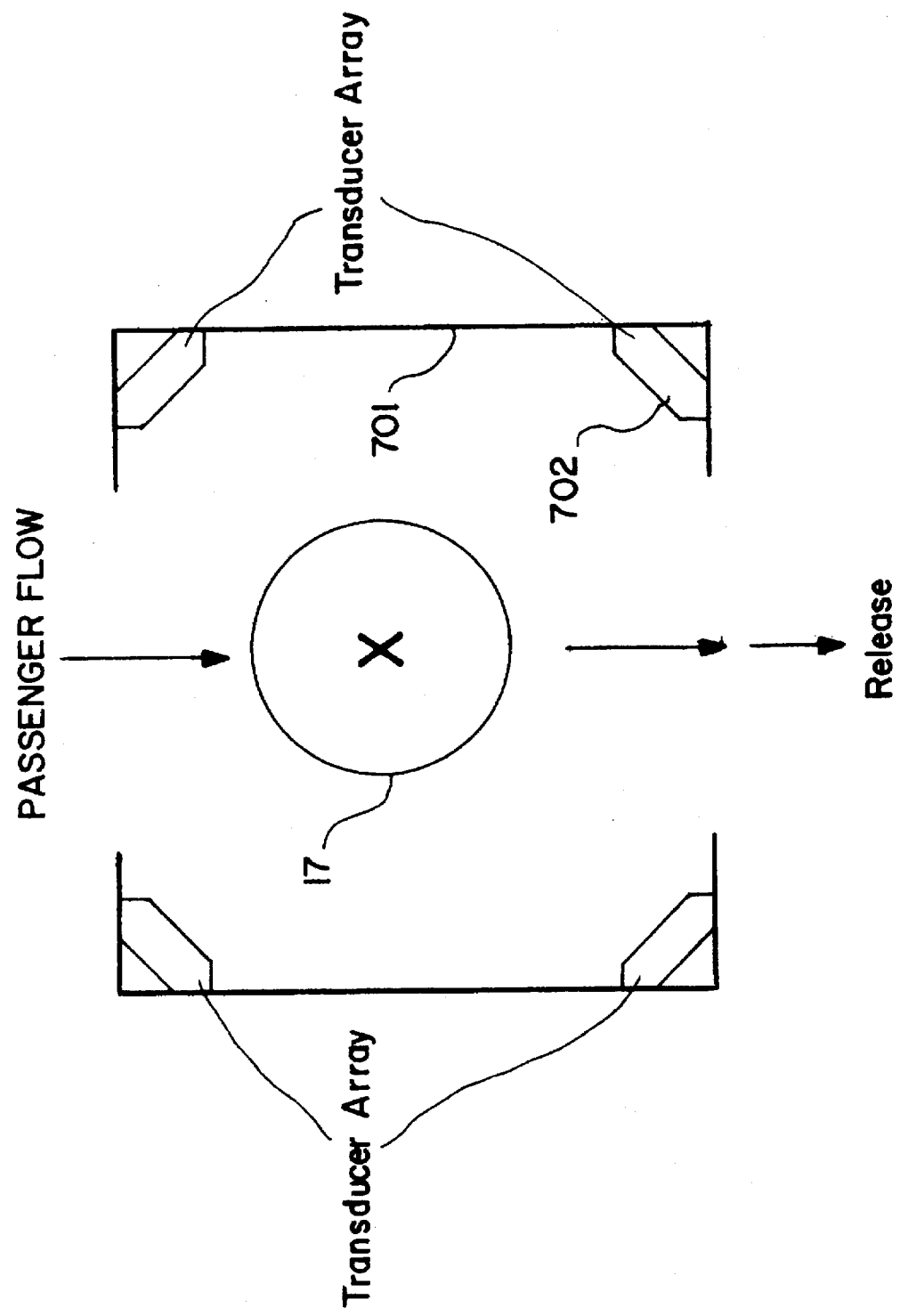
FIG. 2 schematically shows the top view and flow of individuals in a walk-through ultrasonic detector as well as the hand-held ultrasonic detector.

The configuration of the ultrasonic system 700 is shown in FIG. 2, wherein a two-sided compartment 701 surrounds the person during inspection. At each of the four corners a transducer array 702 is placed. The person to be checked enters the compartment and stands on a rotating platform 17 at the center of the compartment. The platform rotates in segments of 90° each until 360° rotation is completed to allow for exposure to the sound waves and proper interrogation. Signals from the transducer are processed by a computer system, generating a 2½-dimension image that shows the contrast between objects carried on the person. Cleared persons would proceed without interruption, otherwise an audio alarm will sound off if a contraband is detected. The image will be interpreted by the computer leading also to a flashing screen and the switch on of a red light. For confirmation of a suspicion a hand-held ultrasonic detector may be used for body search. The detector would include a transducer and an audio alarm to indicate location of a contraband.

A 1-dimensional transducer array would produce a 2-dimensional plot of distance to the body surface vs. horizontal position. Since the passenger must be scanned from head to foot, an additional dimension must be added to the scan. This could be done by turning the passenger in front of a vertical 1-dimensional transducer array. More conveniently, a two-dimensional array could be used which scans in both the horizontal and vertical directions. Since the object producing the echos is close to the source, very little time is required to wait for the echo, so scanning can be done quickly.

One of the first applications of ultrasonics was in the detection of submerged objects such as submarines. The delay in time between a generated pulse and the submerged object gives a measure of the distance. An array of transducers can be used to generate sound waves travelling in any desired direction. Using a delay circuit to delay the oscillation of adjacent transducers, a wave front will be generated at some angle from the transducer array. As a detector, the transducer array similarly becomes sensitive to the direction of the returning echo. This is the principle used in scanning sonar systems.

When there is a large difference in acoustic impedance between materials, sound waves will tend to be reflected rather than penetrating the object. Acoustic impedance values for typical explosives are more than 10,000 times the impedance for air and usually twice to 10 times those for substances normally presence in clothes and personnel articles. Sound waves propagating through air will therefore be almost entirely reflected from a passengers body and any solid or liquid objects in his possession, clothing, being porous, will partially reflect and partially transmit the ultrasonic waves.

The original mount of energy will be decreased due to losses in characteristic of the air medium, and it can be computed by the following relation:

$$I_x = I_o \exp(-2ax)$$

where $I_x$ is the actual intensity, $I_o$ is the original intensity, a is the absorption coefficient, and x is the travelled distance.

Figure 3:
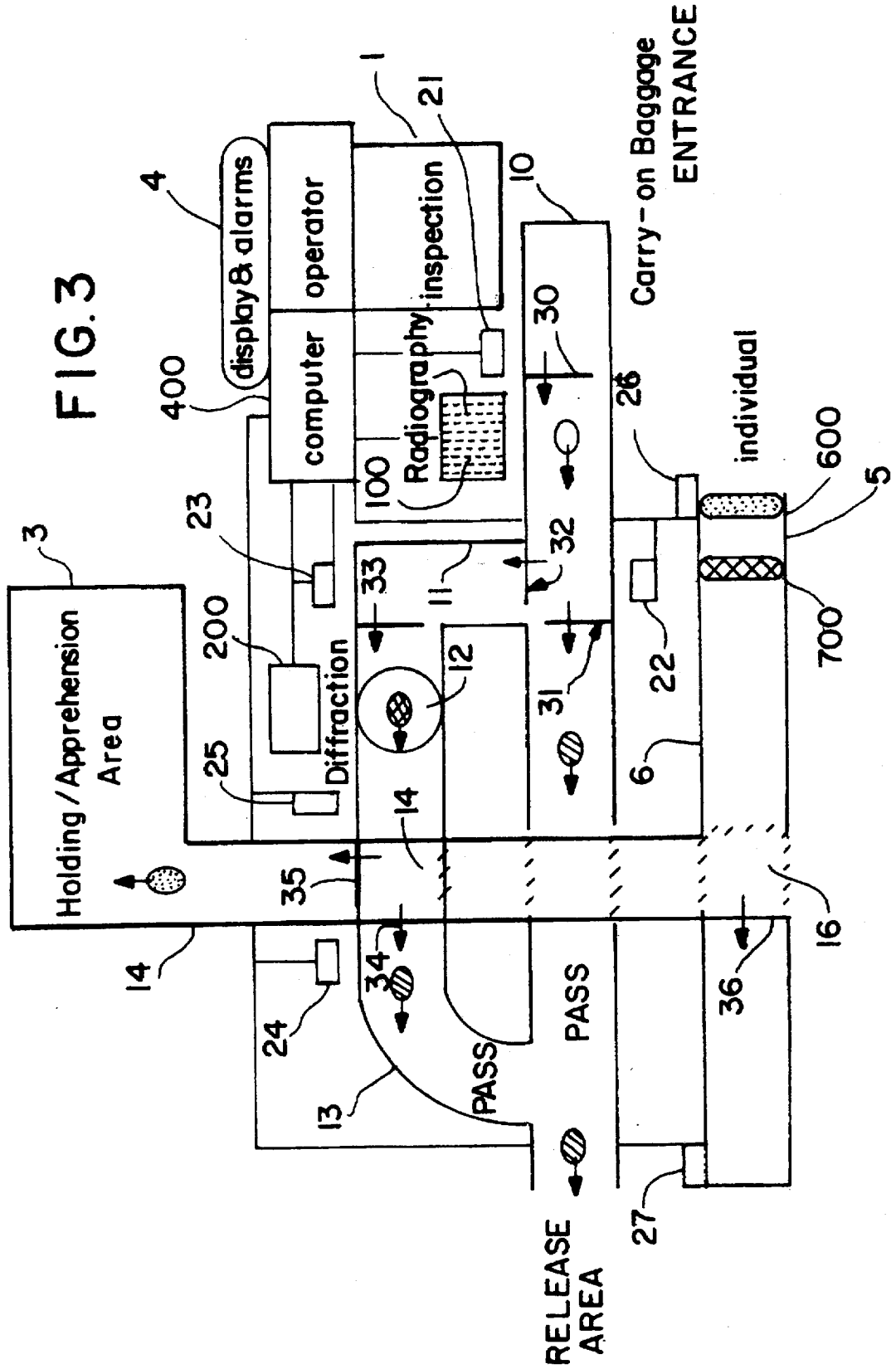
FIG. 3 is a schematic top view of the layout and the process flow of an automated, human-supervised operation of the explosives detection systems of FIG. 1 for carry-on baggage and for individuals.

The values of acoustic, velocity, and absorption coefficient for air and other gases can be used to determine the distance of the individual's skin and/or foreign object on the person s body to the transducer by measuring the time and intensity of the backscatter signal. FIG. 3 schematically shows a top view of the layout and the process flow of the explosives and contraband detection system for carry-on baggage and individuals at security check points. An article to be inspected is placed on a lower level conveyer 10, at station 1, the bar-code placed earlier at the ticketing podium or badging center is read by the bar-code reader 21, and the information is sent to a microprocessor 400, as the baggage crosses gate 30. Next, the baggage is examined by the shadowgraph radiographic unit 100, and the image is observed by the operator at station 4, while the signal from the shadowgraph is sent for processing to the computer 400, and the image is displayed on a video screen. An innocent article continues to move on conveyer 10, its bar code is recorded by reader 22 before crossing gate 31 which is normally open, and the article passes inspection and is released.

In case of a suspicious article or identification of a threat, the video screen flashes, a red light indicator turns on, and an audio alarm sounds, the computer sends a signal to actuate relays on gates 32 and 33 to open, to actuate a relay on gate 31 to close, and to put conveyer 11, into motion. In case the operator identifies a suspicious article at station 4, contrary to the results of the computer image analysis, the operator can override the computer control system. The suspicious article is then directed to the diffraction unit 200 for analysis through gate 33, after recording its bar-code in the reader 23.

The diffraction detection station 200 serves the dual purpose of detecting the presence of an explosive and providing a three-dimensional (effectively, 2½ dimension) image of the baggage based on the diffracted pattern of the explosive, allowing the location of the object to be determined.

At the x-ray diffraction station 200 the object is positioned on the rotating platform 12 for interrogation of each side and to provide the necessary depth information. The baggage would be placed in the correct position by the rotating platform 12, in front of the x-ray beam by computer control of the horizontal and vertical motion of the baggage. Items would be scanned at a faster rate as they pass in front of the detection station on the conveyor. After the first interrogation cycle is completed, a computer signal from the computer system 400, sets the platform 12 in motion and rotates the object (baggage), 90°, then 180°, and then 270°. The rotation occurs until all quadrants of the object are interrogated, whether or not a threat is detected at one of the earlier cycles. This is to carefully specify the location of the threat. If the diffraction system identifies the article as innocent, the article proceeds to conveyer 13, crossing gate 34, which is normally open, its bar-code is recorded by the reader 24, and the article is released. In case of identification of a threat at the diffraction unit 200, the computer closes gate 34, actuates a relay to operate elevator 15 which lifts the article to an upper conveyer 14 after opening gate 35, where the bar code is read by reader 25, and the article is apprehended at station 3 for further interrogation and action.

The signals from the bar code readers 21, 22, 23, 24 and 25 are fed to the computer system 400 which processes the radiographic images from the radiograph 100, performs the analysis of the diffraction patterns from the diffraction unit 200, actuates the alarm systems, rotates platform 12, and operates the elevator 15 and the conveyers 10, 11, 13 and 14 as well as the rotating platform 12.

The different routes of the process flow are controlled by signals fed from the computer 400 to relay switches controlling successive exit doors 30 through 35. The items are introduced to the test routines in a sequential manner. The entrance and exit of each item follows the first-in first-out (FIFO) principle, in which case, one item only should exist in the test line. In order to speed up the operation by examining more than one item at a time, use is made of code labels on the items in which case a code verifier is used at each door in order to route the specific item to the suitable exit or test.

As the individual places the associated carry-on baggage on conveyer 10, the individual places the ticket or identification card on the information recorder 26 and the individual walks through the metal detector facility 600. In ease of no detection, the individual proceeds through the passage 5 which is screened from the conveyers by a barrier 6 to the next step. If a metallic object is detected, audio, visual and video alarms will be actuated. In both cases, the individual enters the ultrasonic facility for interrogation. If the detection is negative the person leaves through swing gate 36 which is normally open after recording the identification information by the reader 27. If a threat is detected, gate 36 is closed and an elevator 16 proceeds to the upper level and the individual proceeds to station 3, for further action. In case of suspicion, the individual may be inspected by a hand-held detector and if necessary apprehended and hand searched.

Figure 4:
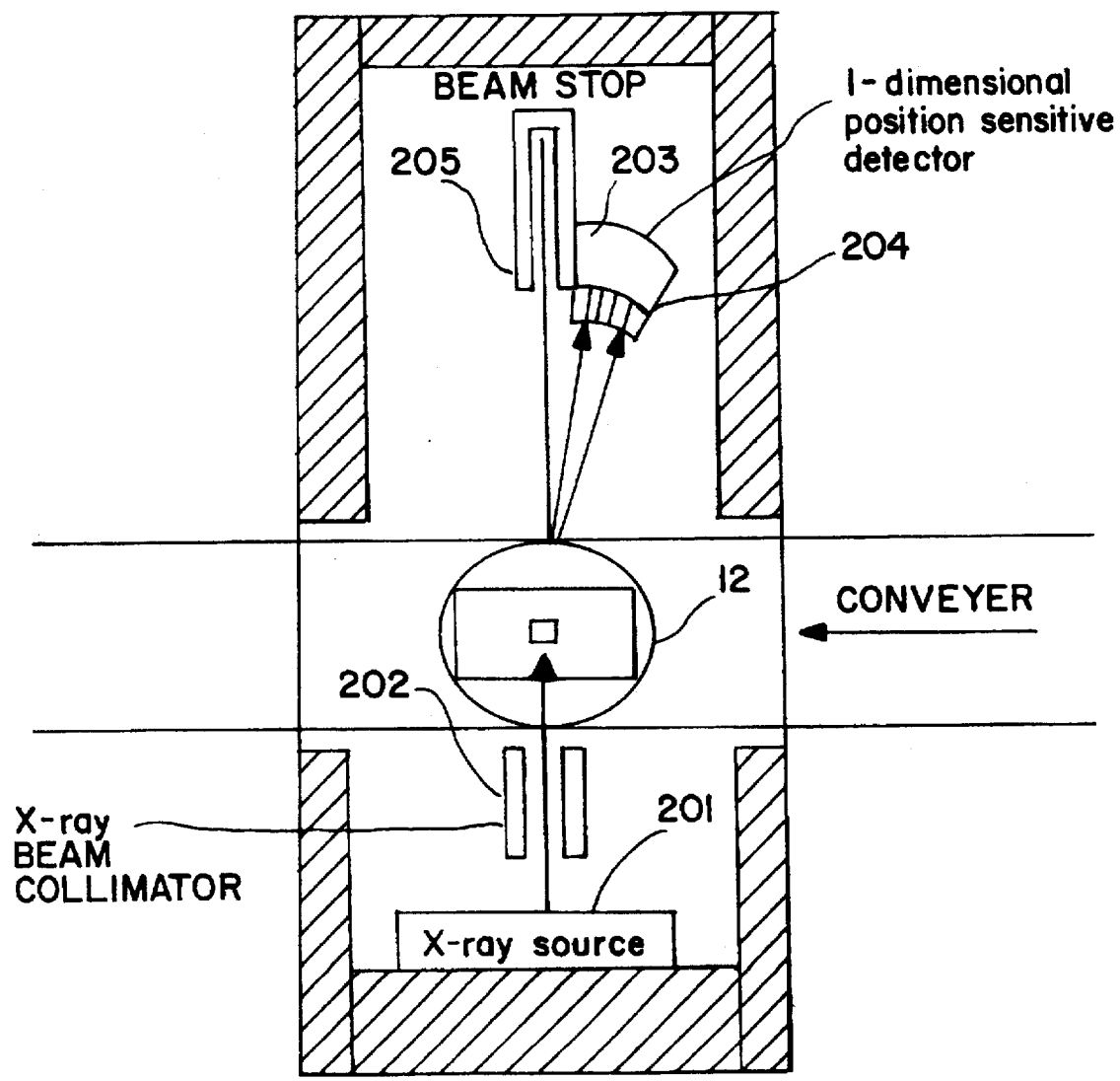
FIG. 4 shows top view of an x-ray diffraction station for inspection of baggages

FIG. 4 shows a top view of a cross section of the x-ray diffraction station 200 wherein an x-ray source 201, produces x-rays which are focussed into a single narrow spot focus beam by the x-ray beam collimator 202. The narrow beam gives the greatest sensitivity and best signal-to-noise ratio by eliminating most of the background scattering from other areas of the object. Since scattering will only occur from material in the probe beam, using a narrow beam will greatly reduce the background scattering. Sensitivity will increase with increased numbers of diffracted x-ray counts collected. An intense source of x-rays, such as that from a rotating anode x-ray generator, is used to produce short wave-length x-rays because the scattering intensity is proportional to $\lambda^3$, where $\lambda$ is the x-ray wavelength.

A 1-dimensional position sensitive detector 203 is used to minimize the length of time required to collect the entire spectrum (I vs. 2$\Theta$) simultaneously, where I is the x-ray intensity and e the angle of scattering. In addition, the position sensitive detector 203, would allow the entire spectrum to be collected simultaneously, rather than scanned as in a conventional instrument, thus reducing data collection time and increasing the signal-to-noise ratio. Background scattering is minimized by choosing a direction which encounters the minimum amount of other material (i.e. the shortest path through the baggage). Additional reduction in background scattering is obtained by using carefully designed slits 204 in from of the detector 203. A beam stop 205 is used to prevent reflection from the transmitted beam.

The ultimate sensitivity depends on the mount of sample in the x-ray beam, the time spent collecting the diffracted x-rays, and the amount of other material contributing to the background scattering. The signal-to-noise ratio may be improved by increasing the intensity of the beam or by increasing the length of time spent measuring a particular spot in the sample. Generally, an effective explosive charge would have to be much larger than the typical 1–2 gm samples used in analytical x-ray powder diffraction instruments. Such instruments typically operate at a relatively low power of ~1 kW. The increased sample size and increased tube power would thus compensate for the lower scattered intensity at short wavelengths and the shorter data collection time available.

Figure 5:
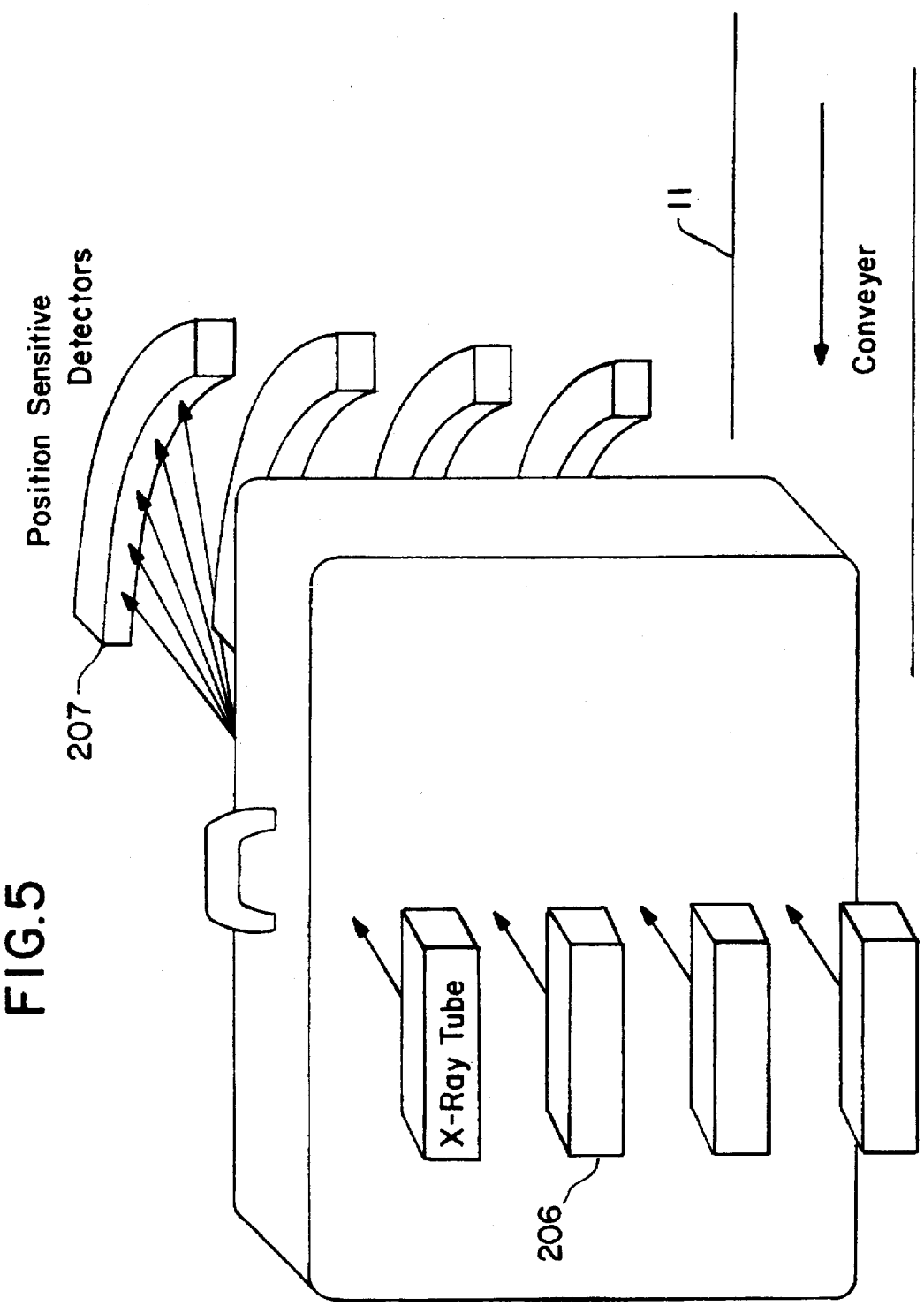
FIG. 5 shows a vertical array of x-ray sources and x-ray detectors for a simple unattended x-ray diffraction system.

Alternatively, a simpler system for unattended screening of carry-on baggage, as shown in FIG. 5, only detects the presence or absence of explosives and contraband and hence does not require a rotating platform. Items would be scanned at a faster rate as they pass in front of the detection station on the conveyor 11. The unattended system consists of a vertical array of x-ray sources 206, and position sensitive x-ray detectors 207. In this case, the baggage would be slowly translated on a conveyer 11 past the x-ray sources. Data collected by each detector would be periodically stored and would thus represent a sum of the diffraction spectra of all materials from a certain area of the item. In this case, the line focus of the x-ray source may be used, increasing the incident intensity and thus further reducing the required exposure time.

An intense x-ray source is employed in the invention to assure rapid analysis since the scattered intensity varies as $\lambda^3$. The x-ray beam is small (~2 mm) to allow accurate interrogation of suspicious objects. A rotating anode x-ray generator of the type which is currently commercially available for diffraction studies is used in connection with the present invention. Typical operation would be at 100 kV and the total power of 12 kW. For carry-on baggage screening, less expensive x-ray sources are used in the invention. For unattended operation, a larger x-ray beam (4 mm×25 mm) is used to probe a larger area of the sample. The baggage slowly moves on a conveyer belt in front of the beam (or an array of x-ray beams). A vertical array of x-ray tubes and detectors thus probe the entire item.

In this aspect of the invention, a single wavelength is selected from the source spectrum using a graphite single crystal monochromator. This limits powder diffractometers for the analysis of small samples. For this invention, shorter wavelengths in the range of medical x-rays are employed to get sufficient penetration of the interrogated baggage rather than the soft x-rays typically used in commercial instruments. For the scan to be completed in as short a time as possible, an intense x-ray source and a detector system which records the diffracted x-ray spectrum at all angles simultaneously is utilized in the invention.

The inventive aspects of the approach is in the use of a detailed analysis method such as x-ray diffraction for processing carry-on baggage, and in providing a computer for image processing and interpretation of the shadowgraph in a manner compatible with the current practice. Another factor is the use of x-rays in which extensive experience has been gained in design, applications, operation, and depth of knowledge in associated hazard as well as potential of use.

Figure 6:
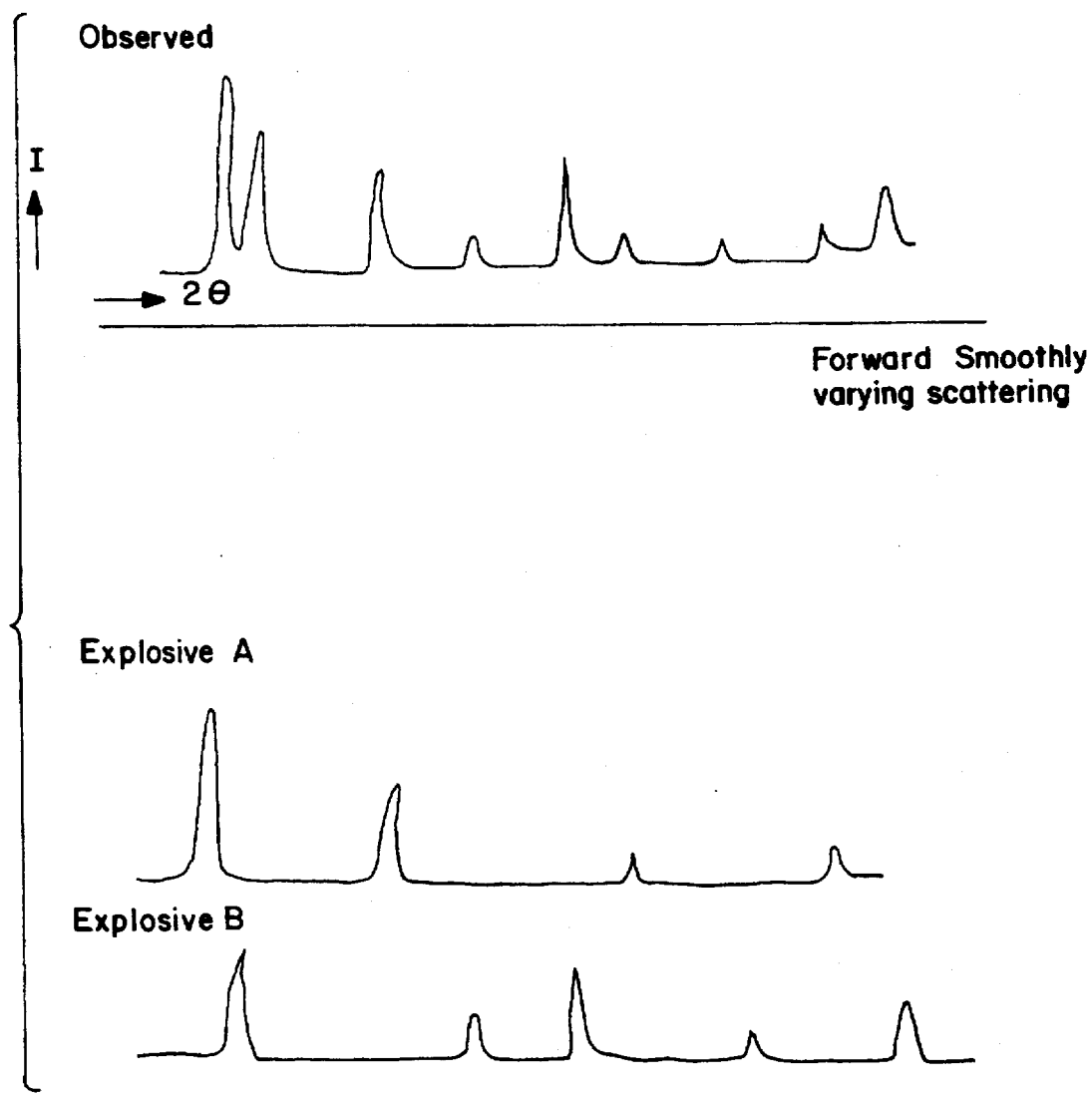
FIG. 6 shows x-ray powder pattern matching process.

FIG. 6 shows x-ray powder pattern matching process, wherein the patterns of known explosives are rapidly compared with the observed spectrum on a screen 60, since each crystalline chemical compound has a unique x-ray powder pattern. The x-ray pattern consists of a series of lines at fixed scattering angle (for a given wavelength) and fixed intensity. The widths of the Lines vary slightly with differences in microcrystalline particle size. When several different substances are present in the x-ray beam, their spectra will be superimposed in the observed pattern, but they can usually and easily be resolved by well known pattern matching and subtraction techniques, yielding in addition, the relative amounts of each substance. The computer will add stored (known) patterns to get best fit to observed pattern, giving relative percentage of each kind of explosive. The least-squares method is used; that is, $$S_{min} = \sum_{2\Theta} (I_{obs} - I_{calc})^2.$$

where $S_{min}$ is the minimum of the sum of the square of the difference between $I_{obs}$, the observed intensity and the calculated (from the pattern) intensity, $I_{calc}$, which is given by, $$I_{calc} = (\%A)I_A + (\%B)I_B + \ldots$$

%A, %B, ... are adjustable parameters.

The x-ray diffraction pattern is easily distinguished from forward (Compton) scattered x-rays which vary in intensity smoothly with angle, and thus contribute a broad background under the diffraction pattern. (See FIG. 6). To obtain a rapid detection of possible explosives in real time, the spectrum (I vs 2Θ) would be analyzed as follows:

First, the slowly varying background would be removed by least-squares fit of a polynomial function to the data. Since the signal from the explosives consists of rapid variations in intensity as a function of 2Θ, they cannot be absorbed in this fit. After background subtraction, the resulting spectrum will be analyzed using the above equations. Since the pattern of each possible explosive, $I_A(2\Theta)$, is known, a least squares fit adds only one parameter, %A for example, for each explosive.

If the spectrum consists of intensity measurements, $I_{obs}$, at 1000 2Θ values, than the presence of as many as 100 different explosives could be simultaneously detected while still maintaining a desirable overdetermination of 10 times more observations than parameters. Since this analysis is a linear least-squares process, it is mathematically well-behaved. The accuracy of the determination is therefore expected to be the absolute size of the signal (which is dependent on the amount of explosive present rather than correlations between parameters or the contributions from benign objects. A lower limit on detectability of explosives is acceptable however, since very small amounts would not present a significant risk. The actual lower-limit can be estimated from detailed computational modeling of the system.

Every solid has a unique x-ray powder diffraction pattern. For most chemical compounds, such as metals, explosives, drugs, the patterns consist of a series of lines in the spectrum whose positions and intensities are a fingerprint of the material. Amorphous and polymeric materials such as glass, wood, leather, and fabrics show only a few weak lines at low scattering angles and/or broad amorphous features in the spectrum. Thus, most of the benign materials likely to be found in baggage or cargo will only increase the background scattering.

Patterns for crystalline nylon, wool, and other fabrics show only a few weak lines and amorphous scattering at low angles and can probably be ignored, or alternatively stored in the computer memory and subtracted from the spectrum. The detection system of the invention differentiates water-based explosive systems from other liquids, in the imaging stage, by the difference in the density and orientation of the liquid-air interface between water-based explosive systems and other liquids. The water-based explosive systems have the unique properties of higher-density (1.1–1.4 g/cm$^3$) and the liquid-air interface is not horizontal. In the diffraction stage, differentiation of suspicious items is achieved by x-ray powder patterns. Water-based explosives show characteristic powder patterns when undissolved TNT, Al or other additives often found the exposure of the baggage to radiation at only a single wavelength, greatly reducing the total exposure to be received by the baggage. Since the time required to measure the complete spectrum is short, the total radiation dose to the baggage is minimized, and is not significantly greater than in an x-ray radiographic scan. Other than the fogging of photographic film, no damage to baggage is expected for x-rays in the 50–100 kV range.

A position sensitive detector is used to analyze objects as quickly as possible. The detector of preference is a one-dimensional proportional counter, which is commercially available, and which is filled with xenon gas to improve the efficiency at high x-ray energies. Output from the detector is directed to a microcomputer for analysis. For unattended operation, the spectrum recorded from each detector will be dumped to the computer memory as soon as a sufficient signal is collected. The pattern corresponding to an explosive material could then be traced to an approximate location in the baggage.

The major components of the preferred embodiments including the x-ray tubes and the position-sensitive detectors which are commercially available. The x-ray tubes are operated separately, that is a failed tube will not affect the operation of the others. Any failure is likely to short the tube and the failed tube can be easily replaced. The electronic components can be assembled in plug-in boards which can be easily replaced. The minimum hardware required for data processing is: one (1) supermicrocomputer, or a personal computer such as IBM or a clone, an analog-to-digital converter (ADC), an audio alarm, a visual alarm, and an analog display monitor. The hardware architecture is based on a local area network (LAN).

Analysis by x-ray powder diffraction is a proven technology and widely used analytical technique. A number of commercial manufacturers market x-ray in water based explosives are present. X-ray powder patterns from undissolved ammonium nitrate (if present as in slurry) are also appropriate for recognition of water-based explosive systems and for differentiation from other liquids.

Sheet explosives should be relatively easy to detect in a diffraction system, as opposed to a radiographic imaging system, since in the unattended mode the powder pattern is collected over a relatively large area of the baggage. Sheet explosives show the characteristic x-ray powder pattern of PETN crystallites. Sheet explosives have higher density (1.4–1.55 $g/cm^3$) compared with paper, fabric, and similar shaped materials which have substantially lower densities (0.7–1.2 $g/cm^3$).

Figure 7:
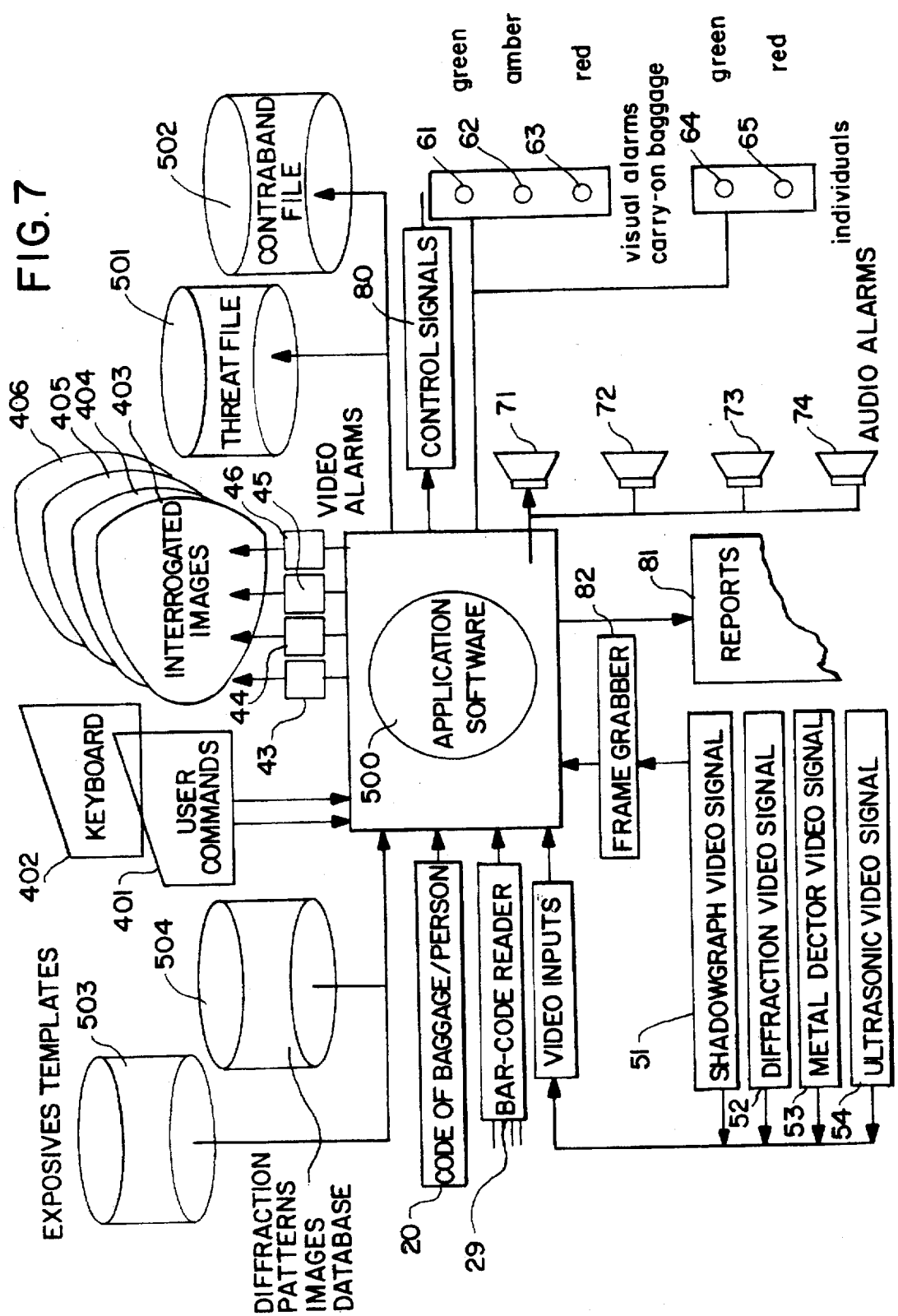
FIG. 7 shows a functional diagram of the central processing system at the security check point as it relates to FIG. 3.

FIG. 7 shows a functional diagram of the shadowgraph enhancer and the x-ray action. The processor 400 responses to user manual commands 401 from a keyboard 402, records inputs from bar-coder 20 and bar code recorder 29 which receives signals from bar-code readers 21 through 27, video inputs from shadowgraph 51, from the diffraction unit 52, from the metallic detector 53, and from the ultrasonic detector 54. Four video screens are provided for display of interrogated images: screen 403 for interrogated images from the shadowgraph, screen 404 for diffraction images display to identify and localize threats in carry-on baggage, screen 405 from the metal detector and screen 406 for the ultrasonic detector for display of images from individuals' inspection. Each screen has a flashing capability in case of identification of a threat or contraband. The flashing of screens 403, 404, 405, and 406 is respectively induced by the video alarm interrupters 43, 44, 45, and 46. Stored on the computer 400 are a threat file 501, contraband file 502, explosive templates 503, and a database of threat and contraband patterns 504. The application software 500 includes software for image enhancement and matching algorithms. The outputs include signals to three visual annunciators for carry-on baggages the green indicator 61 for innocent object, the amber indicator 62 for suspicious objects and the red indicator 63 for threat. For individual screening, a green light 64 indicates a cleared person and a red light 65 indicates an uncleared person. This is in addition to audio alarms 71, 72, 73, and 74 that sound off in the operator station 4 and the holding station 3, to annunciate a threat sums detected respectively by the shadowgraph, the diffraction unit, the metal detector or the ultrasonic detector. The system outputs also include control signals 80 directed to gates and conveyers in response to detection outcome, and printed reports 81 on identified threats.

The view on the shadowgraph screen is triggered by input signal 51 and is displayed on the monitor screen 403 as a two-dimensional image with different gray scales. Discrimination and interpretation of images of threats depends on human visual judgement, in which case a threat may be missed. Hence, images are transferred to the computer for analysis by a depth and contrast program to enhance the view and/or give an alarm in real time. The image processing includes three steps: digitization of the picture and saving it in the computer memory, analysis of the picture contents and discrimination of the threat objects by an application software, and delivering the alarm at the right time.

The analog picture fed to the shadowgraph monitor is transferred directly to a frame-grabber 82 which changes the RGB signal to hue-saturation-intensity (HSI) signal ready for processing by the computer. Two types of processing are available. The first is Hue and saturation processing with a color picture including: color identification, edge enhancement, and object differentiation; color desaturation/ saturation, colorimetric analysis, and colorization; compression/decompression; frequency domain analysis; and tinting, retouch, thresholding and special effects. The colors employed are artificial and have no relationship with the original colors of the items in the baggage. Alternatively, intensity or gray"scale processing with a black and white picture may be used. This involves: edge enhancement, noise reduction, and histogram analysis, arithmetic and logic operations, frequency domain analysis such as the fast Fourier transform (FFT), and compression/decompression.

Whether color pictures or gray scale pictures are used, a picture data-base is constructed to contain the signatures of some threats (firearms, grenades, incendiary and explosive devices, or pure incendiaries and explosives etc.) in different positions. These signatures are stored in the computer external storage as templates for comparison with the input picture data. Depending on the program logic, if a match occurs between the input picture and the reference template, the response may be an audible alarm or an audio/video alarm. The minimum hardware required is an IBM-PC or compatible, an analog RGB display monitor, a 512 kB RAM (Random Access Memory), and a frame-grabber, for example (DT 2871 HSI) color frame-grabber board). Furthermore, the enhancer utilizes a flashing capability of the monitor which will identify the threat in the baggage for inspection by the diffraction unit.

The algorithm of pattern recognition depends on prestored signatures or templates in the computer memory, which are compared to the interrogated picture. The method of comparing two pictures should not depend on the shape or the size of the threat but on the specific characteristics of ultrasonic waves in the medium of the expected threat such as absorption coefficient and velocity, etc. In this way the probability of detection will be raised considerably. Image processing of the pictures received from the passengers ultrasonic detector is enhanced by pre- and post-image filtering and averaging three or more images based on several scan directions.

Figure 8:
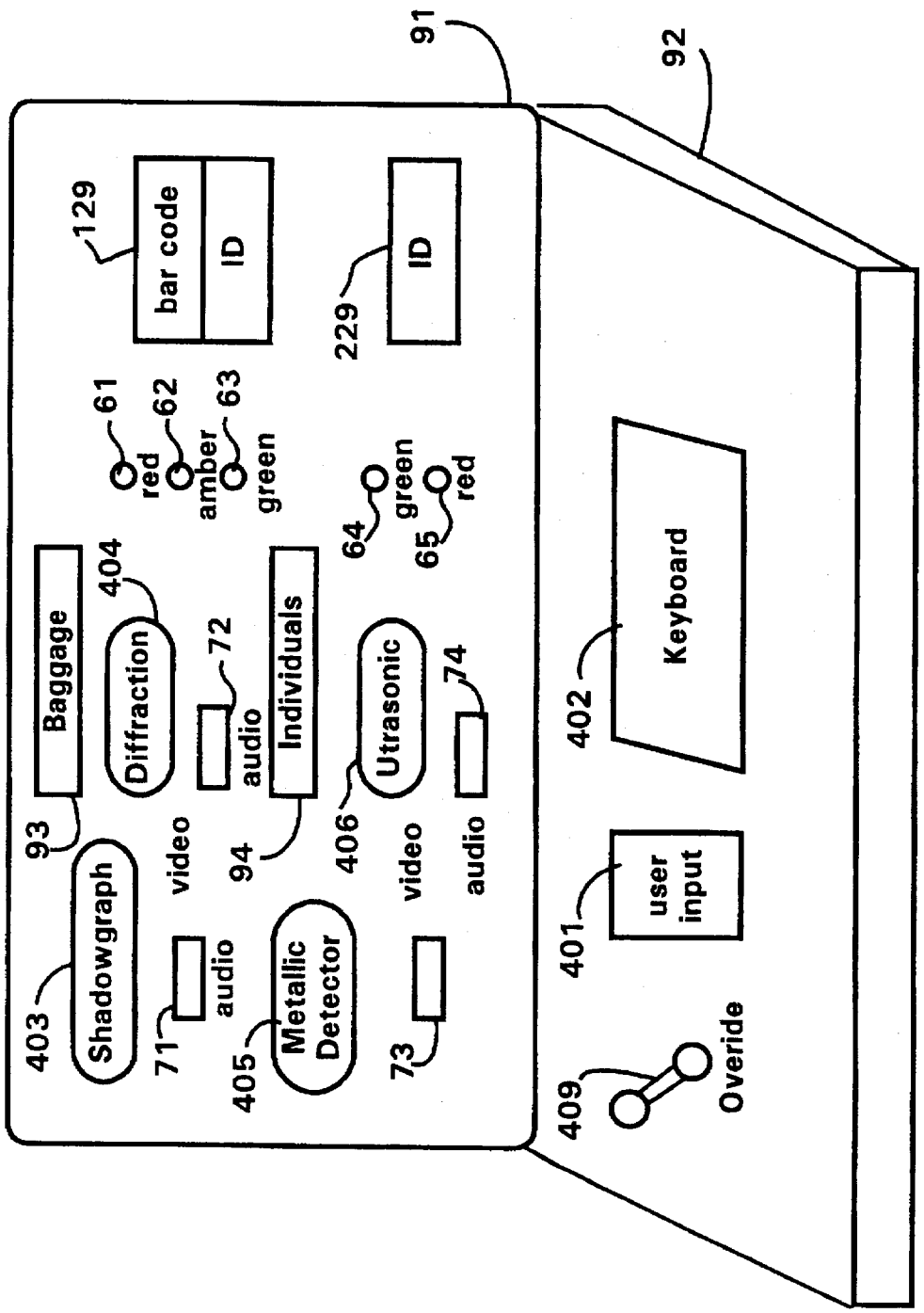
FIG. 8 shows a schematic of the display and control panel of the security check point supervisor.

FIG. 8 is a schematic of the display panel 91 and the control panel 92 in the operation room 4 which is available for the system operator. The display panel is partitioned in two areas: one area 93 is allocated for carry-on baggage and one area 94 is identified for individual screening information. In the baggage screening display area, the video screen 403 shows images from the shadowgraph and screen 404 shows images from the diffraction interrogation unit; audio alarm 71 for annunciation of a threat identified by the shadowgraph and audio alarm 72 for indication of a threat detected by diffraction; visual alarms comprising green light 61 for benign baggage, amber light 62 for suspicious, and red light for threat; and the display 129 for the bar-code identification of the baggage. In the individual screening area the video screen 405 displays images associated with the metallic detector and the screen 406 for images associated with the ultrasonic detector, audio alarm 73 for annunciation of a threat detected in metallic detection and audio alarm 74 for threats detected by ultrasonics, and green light for cleared persons and red light for uncleared persons, and the display 229 for the identification code of the individual. The control panel 92 includes user command inputs controls 401, a keyboard 402 and an override control 409 to interfere with the automated operation in case of a detected failure of recognition.

Figure 9:
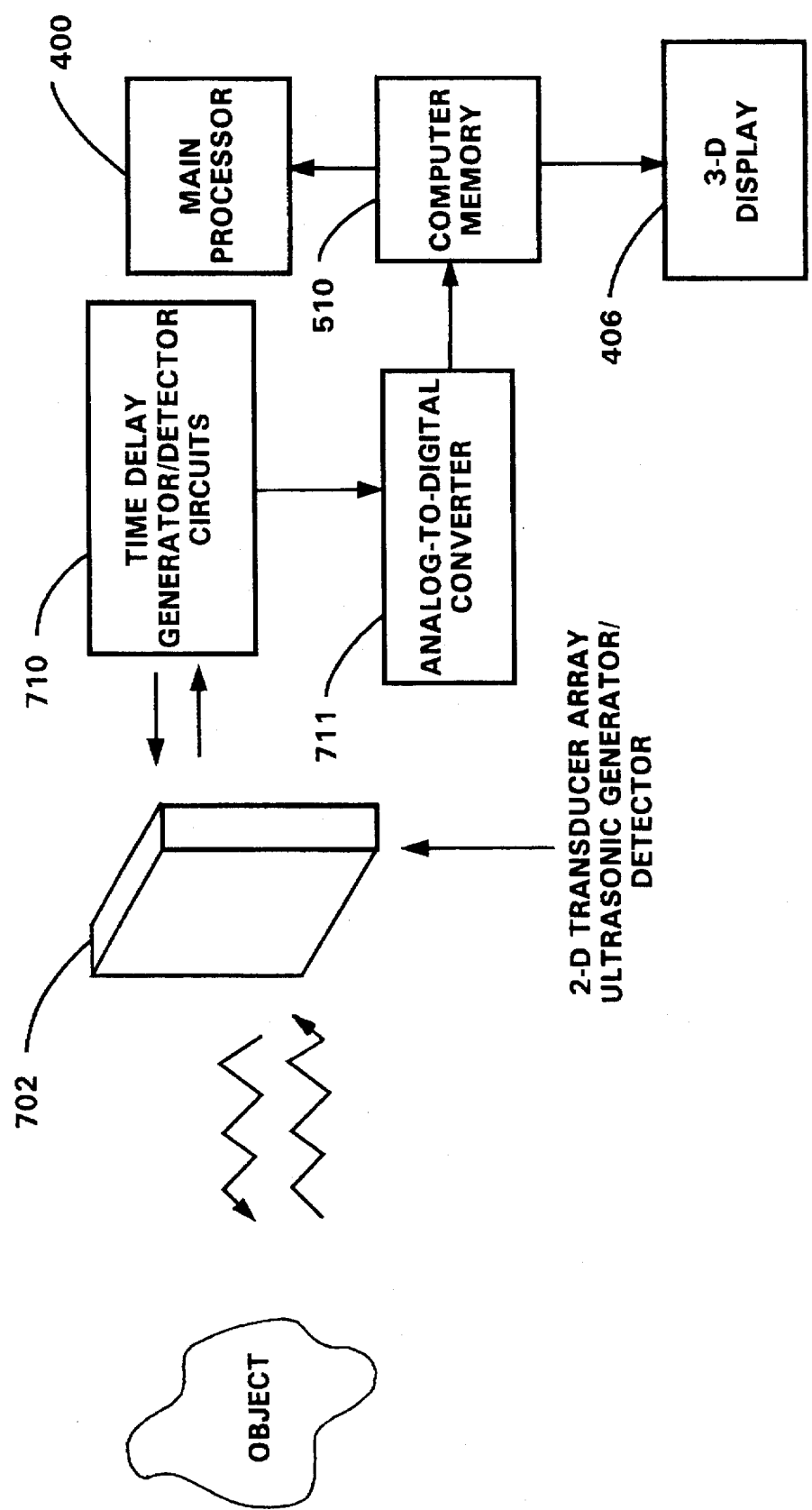
FIG. 9 is a block diagram showing the arrangement of major components of the ultrasonic detector for individuals.

FIG. 9 is a block diagram of the individual screening system showing the relationship of the ultrasonic detector components. The signals from the 2-dimensional transducer array ultrasonic generator or detector 702 are directed to the time delay generator and detector circuits 710 and then processed by an analog-to-digital converter (ADC) 711 prior to being recorded in the computer memory 510 of the main processor 400 and displayed on a 3-dimensional display 406. By means of pattern recognition algorithms, the picture can be analyzed in order to know if it contains a threat.

The intensity of reflected sound waves decreases rapidly when reflection does not occur normal to the surface (the "golden rule" of ultrasonics). Therefore, in order to provide full coverage of the passenger, the screening chamber has transducers located at each of the four corners. The four transducers (FIG. 2) are operated in a sequential order to avoid interference with each other. A whole body scan should not take significantly longer than current metallic screening systems. The output of the 2-dimensional transducer array is fed to a cathode ray tube (CRT) 406 for display. Some additional difficulty is presented by the fact that the data to be interpreted is fully 3-dimensional in character. Rapid analog to digital conversion would allow the image to be displayed with a current generation 3-D graphics display system, such as the Evans and Sutherland PS 390. This system can display, rotate, and translate 3-D graphics data at 365,000 vectors per second. Multiple echos such as those due to both clothing and body surface could be visually distinguished by using alternate colors. Scans could also be stored for later reference.

The relatively low frequencies of ultrasonic (about 20–60 kHz) have wide applications; for example, as ultrasonic burglar alarms, as rodent repellers and as obstacle avoidance aids for the blind. Various non-destructive testing devices for metals use ultrasonics. Other industrial applications include drilling and cleaning. In the upper range of the spectrum, medical applications are increasing in popularity especially in imaging to replace x-rays. Sonars are used under water for detection and navigation. Basically, the expansion of ultrasound applications have resulted in development of various types of transducers and detectors which are adapted in the invention.

Figure 10:
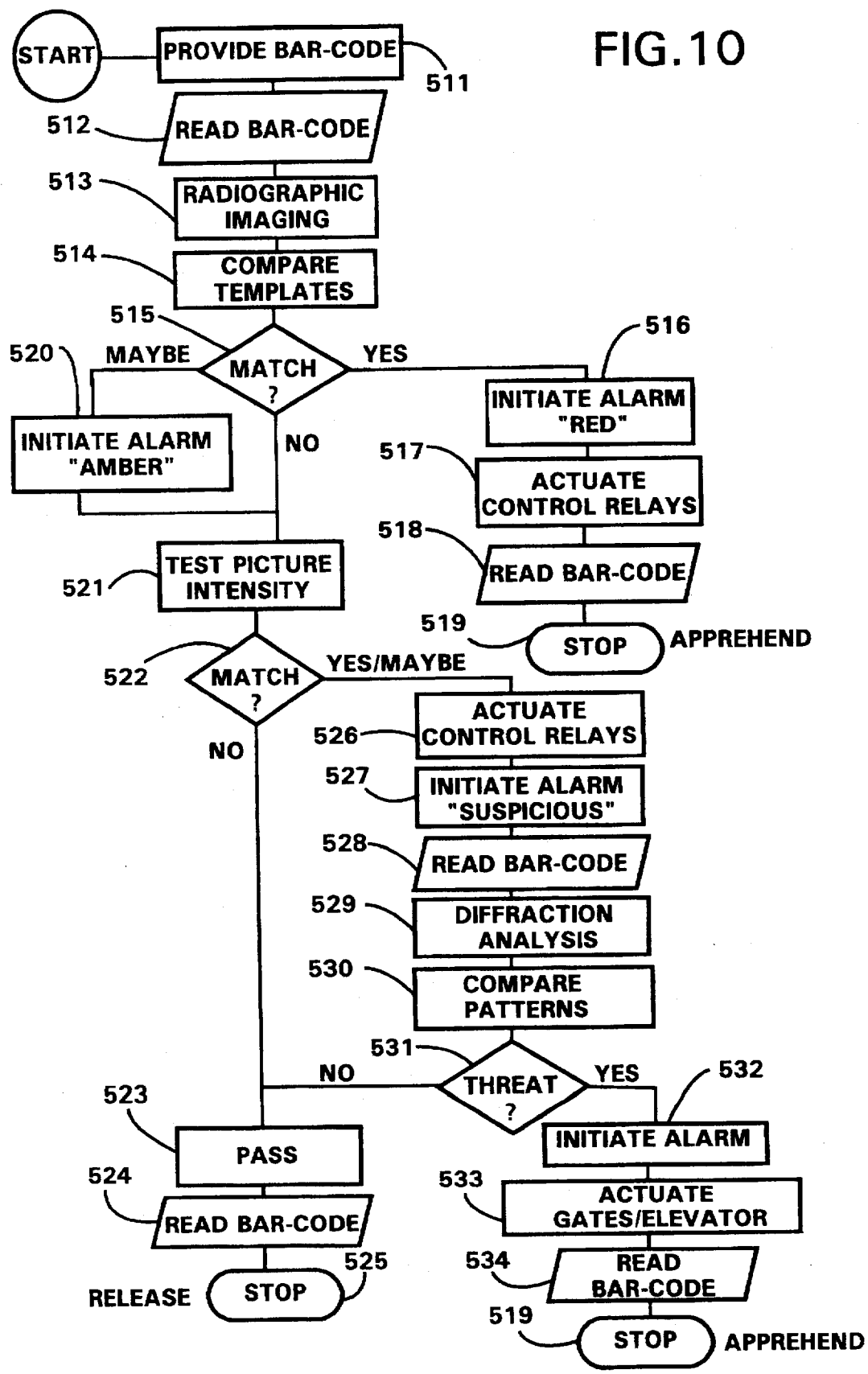
FIG. 10 shows a system logic flow diagram of the algorithm of the combined shadowgraph and diffraction screening process as it relates to FIG. 3 for concealed contraband in carry-on baggage.

FIG. 10 is a system logic flow diagram of the algorithm used in the combined shadowgraph and diffraction screening process for detection of concealed contraband in carry-on baggage, showing the algorithms used for processing a typical carry-on baggage or article. The inspection procedure starts by step 511 with affixing on the baggage and the passenger ticket or the identification badge of the individual an identification bar-code or equivalent, reading the bar code in step 512 by reader 21 (FIG. 3), performing radiographic imaging in step 513, comparing in step 514 the interrogated image with templates previously stored in the image database of different threats 501 and contraband 502 (FIG. 7). If a sure match occurs in the matching step 515, between the input image and the reference image, a signal is initiated in step 916 by a computer signal which is fed to the loudspeaker 71, to the red light 63 and to flash the screen of the video alarm 43 (FIG. 7), to indicate the presence of a threat in the baggage. In addition, control signals 80 (FIG. 7) will be sent in step 517 to swing gates to control routes of the examined baggage in the lines of detection. Then, the bar-code of the item is recorded in step 518 and then directed in step 519 to the apprehension station 9 (FIG. 3). If a match in step 515 indicates a suspicious object a signal is issued by the computer in step 520 to turn on the amber light 62 (FIG. 7) and the next step 521 of the interrogation takes place.

If no match is found or a suspicious object is detected in step 515, the picture intensity is tested in step 521, perforating an intensity match in step 522. If no match is found the article passes inspection in step 523 and the procedure is terminated by checking the bar code for validation in step 524 by means of reader 24 (FIG. 3) and the article is released in step 525. If a match is made, a suspicious article may be present and hence the amber light 62 (FIG. 7) is lit in step 526. The article is directed in step 527 to the diffraction station as suspicious item by actuating the appropriate control relays to gates 31, 32, and 33 and conveyer 11 (FIG. 3) through signals generated by computer controls 80 (FIG. 7).

The inspection procedure starts by step 528 at the diffraction unit with reading the bar code of the suspicious item by reader 23 (FIG. 3), performing diffraction analysis in step 529, and comparing (step 530) the interrogated pattern with patterns previously stored in the database of different threats 504 (FIG. 7). If a match occurs between the input pattern and the reference pattern in step 531; alarm signals are initiated in step 532, by the program and fed to the loudspeaker 72, the red light 63, and the video alarm 43 (FIG. 7) to indicate the presence of a threat. In addition control signals, in step 533, will be sent by computer output 80 (FIG. 7) to swing gates 34, conveyer 14 and elevator 15 (FIG. 3) to control routes of the examined baggage and cargo in the lines of detection and the bar-code is recorded in step 534 by the reader 25 (FIG. 3) to proceed with apprehension 519. If no match is made in step 528, the article is passed in step 523, the bar code is recorded in step 524 by reader 24 (FIG. 3) and the baggage is released in step 525.

The concurrent individual screening utilizes a redundant system that involves the traditional metal detection or sniffers. In that these systems are known in the art, their structure will not be set forth herein in detail. The ultrasonic detector, however, is based on an acoustic configuration. Sound waves at frequencies above the human hearing limit of 20 kHz are ultrasonic. Sound waves in air propagate at 330 m/second. An ultrasonic pulse at a frequency of 330 kHz will therefore have a wavelength (and maximum resolution) of 1 min. Ultrasonic sound waves are generated using a transducer. One type of transducer consists of a piezoelectric crystal to which an alternating electronic current is applied. The electric field produces a distortion of the crystal generating a mechanical wave. The opposite effect occurs, so transducers can also be used to detect sound waves.

Figure 11:
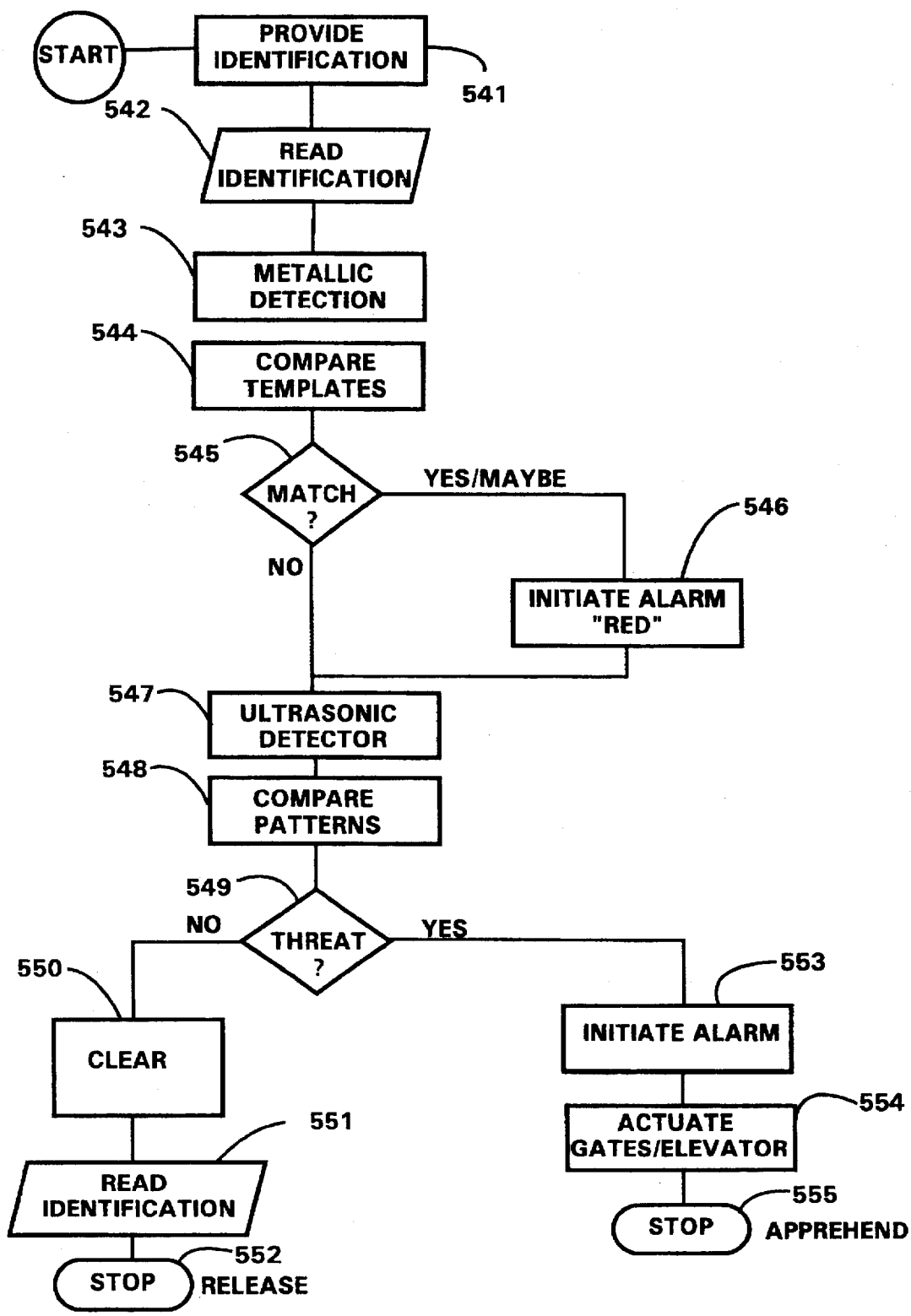
FIG. 11 shows the algorithm for screening individuals at a security check point for contraband.

FIG. 11 shows the algorithm for individual screening. The process starts by providing an identification in step 541 similar to that on the associated baggage by coder 20 (FIG. 7). Upon start of the screening the identification is read in step 542 by reader 26 (FIG. 3) and metallic detection is performed in step 543, comparing in step 544 the interrogated image with templates previously stored in the image database of different threats 501 and contra-band 502 (FIG. 7). If a match occurs in step 545, between the input image and the reference image, a signal is initiated in step 556 by a computer signal which is fed to the loudspeaker 73 and to indicate the potential presence of a threat. The individual then proceeds to inspection by ultrasonics in step 547 wherein the image is compared with stored threats in step 548. If in the matching step 549, the person is cleared in step 550, the identification is recorded in step 551 and the person is released in step 552. If the person is not cleared a signal is sent in step 553 to actuate the audio alarm 74, to light the red light 65 and to flash the screen of the video alarm 45 (FIG. 7). In addition, control signals 80 (FIG. 7) will be sent to swing gate 36 and elevator 16 to control the passage of the individual in the lines of detection in step 554 and the person is directed to holding station or apprehension in step 555.

Ultrasonic imaging has become an important medical diagnostic tool in cases where x-ray radiography or tomography is inappropriate, for example in obstetrics. By placing the transducer in contact with the skin, a 2-dimensional scan of the body interior can be obtained and displayed on a CRT. The transducer must be in contact with the body, otherwise most sound waves will be reflected by the surface rather than penetrating the body.

Most applications of ultrasonics involve propagation of sound in liquids or solids, where the attenuation is relatively low. Bats, however, navigate and locate prey by emitting ultrasonic chirps. Also, an automatic focusing camera has been developed by Polaroid based on ultrasonic pulse-echo ranging. The frequency range used by medical applicator, is not efficient if the air is used as a medium for propagation, even though the range from 20 kHz to 100 kHz can be used for transmission of ultrasonic waves in the air. Keeping in mind that the resolution required for medical applications (about 1 mm) is much higher than the resolution required for passengers screening, successful propagation and detection can be achieved using ultrasonic waves within this frequency range.

Figure 12:
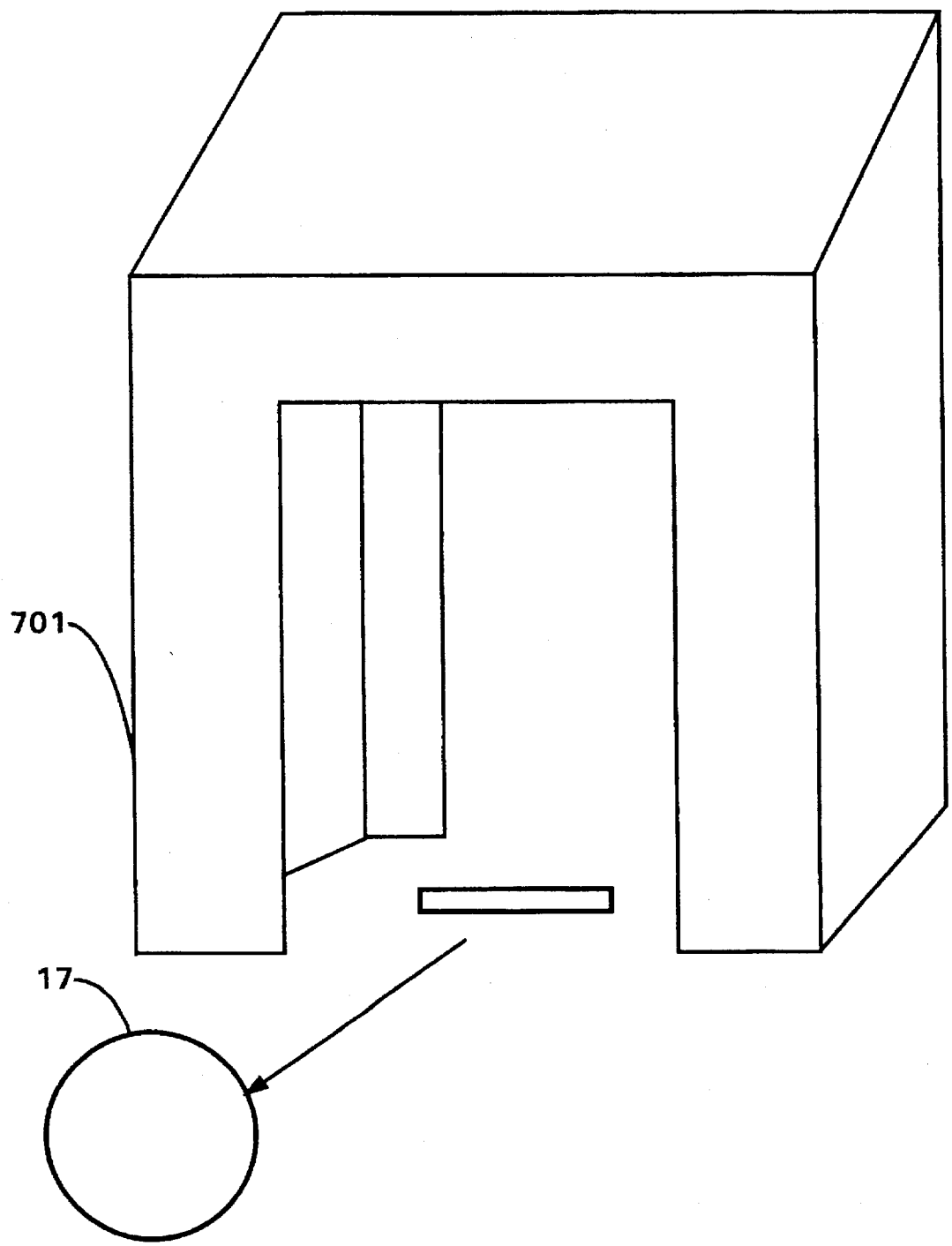
FIG. 12 shows a view of the ultrasonic arc detector.

With the sonar detector set forth herein for screening of personnel for explosives and other non-metallic objects using ultrasonic sound waves, an individual or passenger enters a screening chamber as shown in FIG. 12 which will provide a rapid surface scan from four (4) directions. Ultrasonic waves reflected from the body surface are detected and converted into 2 or 3-dimensional images on a CRT display 406 (FIG. 7). Any solid objects, such as explosives, plastic guns, etc., hidden below the clothing will be detected as irregularities in the body surface. Unlike x-rays, ultrasonic sound waves beyond the normal range of human hearing have no adverse medical consequences.

Acoustic waves are used as tools of interrogation since they induce no harm if reflected from the outer surface of the body, especially at the low frequency and intensity of interest here. Acoustic detection does have limitations, however, the selection of the appropriate frequency, imaging technique, and configuration allows those limitations to be overcome. Although sonars have been successful in water navigation, propagation in air has limited their applications. Also, ultrasonics have been used in diagnostics and are gradually replacing x-rays. However, the transducer has to be in intimate contact with the skin and often a conducting gel has to be used. The acoustic frequency is high enough that the waves can not propagate in air. The ultrasonic system is acceptable as safe by the public and does not represent any hazard when used in the range of interest. Also, the ultrasonic system does not effect hearing aids and pacemakers.

Figure 13:
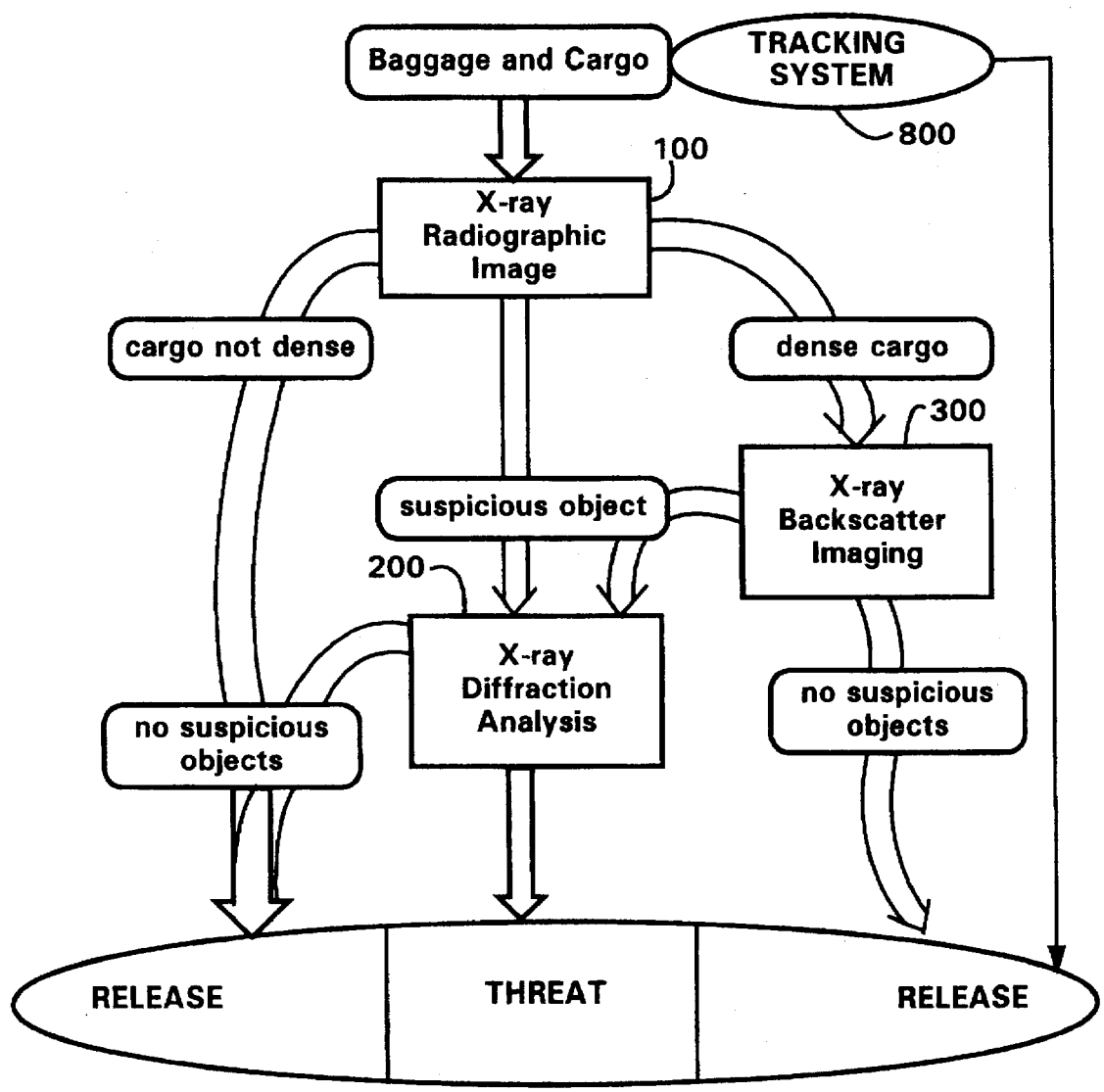
FIG. 13 shows a flow chart of the screening process for concealed explosives in dense checked-in baggage and air cargo using x-ray radiography, backscattering and diffraction.

In the second embodiment of the present invention, a non-vapor, non-nuclear explosive and contraband detection system is disclosed for checked-in baggage and/or air cargo, which are mostly dense items. This embodiment of the present invention proceeds as with the previously discussed embodiment of the invention with the screening of checked-in baggage illustrated in FIG. 1 and FIG. 3 with the addition of an x-ray backscattering unit for interrogation of dense cargo prior to detailed analysis by x-ray diffraction. The flowchart of the system is depicted in FIG. 13 wherein the procedure comprises the use of a standard x-ray radiographic imaging unit 100 as a first stage. In case of dense cargo, the screened item proceeds to an x-ray backscatter imaging unit 300 for interrogation. Should an object raise suspicion, the item is directed to an x-ray diffraction analysis unit 200 for detailed analysis, otherwise it will pass the checking process and get released. Items which are not dense, wherein suspicious objects are located by the x-ray radiographic imaging can be directly moved to the x-ray diffraction analysis for detailed interrogation. In addition, a tracking system 800 is employed with the detection process to associate each piece of checked-in baggage with a passenger.

Figure 14:
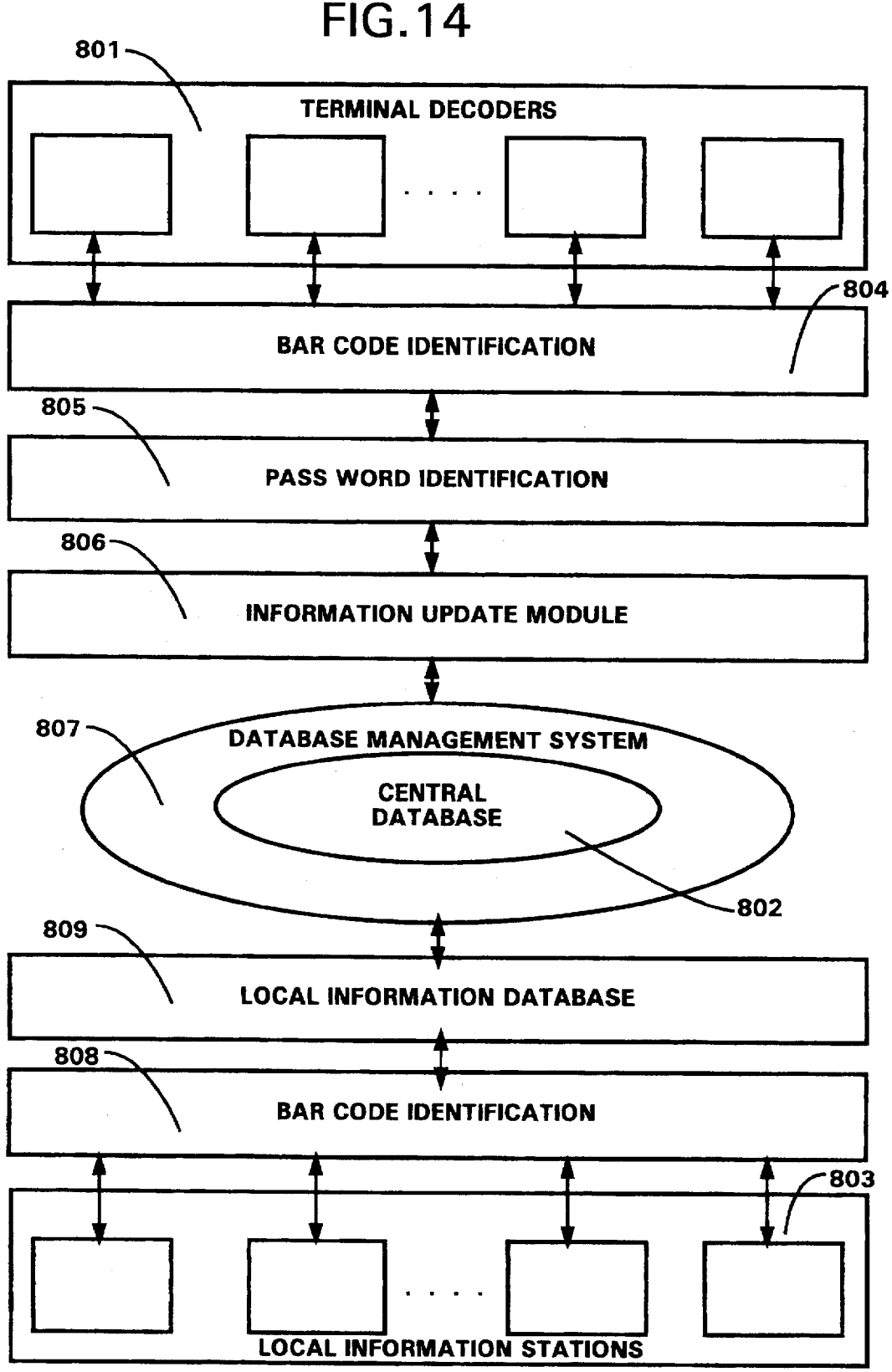
FIG. 14 shows a flow chart of the modules of the airline baggage tracking system.

FIG. 14 shows the basic modular structure of the tracking system which consists of three major subsystems: terminal decoders 801, a central database 802, and local information stations 803. The bar code and decoder play the major role of tracking while the central database provides information support. The bar code is printed linewise in a serial fashion by means of an impact printer, and a microprocessor or a computer provides storing, retrieving, and rapid processing of information. The integration of the central database, the local information station and the terminal decoder involves a delicate network for security and service. Dynamic situations of passenger boarding and baggage loading can be clearly defined. Consequently, potential service interruption or security violation can be inhibited. Also, better service information can be made available without adding any extra loads to airline personnel.

Terminal decoders 801 comprise either portable light-pen bar code decoders or desk-top style scanners, which can be provided at check-in terminals or curb-side check-ins, passenger boarding entrance, baggage sorting station, and baggage claim area. Each decoder provides identification and validation through the bar code identification module 804 and the password identification module 805, and verifies and updates information via access to the central database through the information update module 806 for validation and verification of on-board and off-board situations. The bar code identification module 804 recognizes acceptable bar codes and performs the identification. The password identification module 805 checks passwords of terminal decoder 801, and updates the data in the central database 802 if the password is valid. The information updating module 806 turns on the appropriate channel to access and update the information in the central database 802 directly.

The central database 802 stores and provides personal data, travel information, and the track of the accompanying checked-in baggage based on information or requests received from different local information stations 803 and terminal decoders 801. As shown in FIG. 14, the central database 802 is managed by a database management system 807 which provides information to a specific query from different local information station and terminal decoders.

A local information station 803 provides input of and access to travel information and transfer particulars in airports as well as confirmation services. Data updates are provided by a bar code identification 808 and a local information database 809 connected to the central database which are adequate for information services of boarding or loading. A local information database 809 introduces local information; such as locations of next boarding gate, baggage claim and check-in, airport terminal, restrooms, telephone booths, etc. In general, a number of local information stations may be installed as a desk-top decoder with color monitor at the critical points in airport terminal zones.

The coordinated integration of a large, powerful central database and its supporting local information stations and terminal decoders insures the adequacy of the capability of performance of security checks on air travel, of identification, and of avoidance of situations leading to misplaced baggage, as well as of passenger boarding verification. The inventive aspects of the system is in fusing information from various terminal decoders and providing a comprehensive and efficient display of alert or warning signals of potential violation of air travel security without adding human intervention on the part of passengers and airline personnel.

Figure 15:
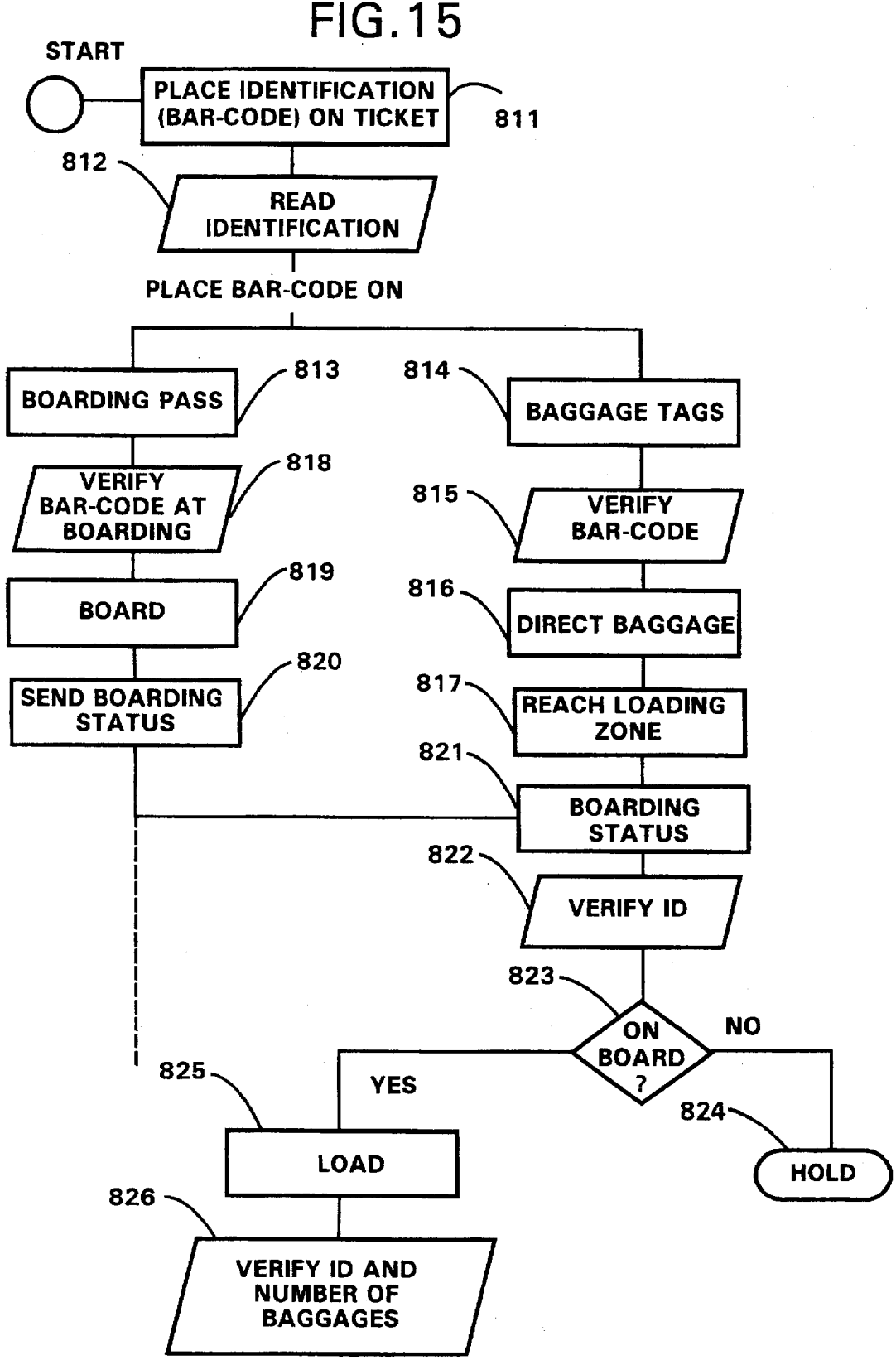
FIG. 15 is a logic diagram of the passenger boarding procedure and the associated baggage loading procedure constituting a portion of the airline baggage tracking system as it relates to FIG. 14.

In order to install the system for use, the system has to be configured by analyzing all possible functional situations, considering various conditions that may conceivably take place in any airport while boarding and loading, to assure the comprehensiveness of the tracking system. Considering the general aspects of air travel, the flowchart of the tracking system logic is shown in FIG. 15. The check in proceeds by printing a bar code representing an identification of a specific ticket at the corner of each page on the ticket, step 811. A check-in decoder will check in the passenger be reading the bar code on the ticket, step 812, and transferring the code to the boarding pass, 819. The same code is placed on the baggage, step 814. The bar code on the ticket is used as an identification and as a tool for tracking the baggage. The baggage are verified against the ticket, when the baggage is to be checked in through bar code scanning at the airline ticket terminal or curb check in, step 815. Each piece of luggage has a bar code related to the one on the passengers ticket in addition to a serial number and an indication of the number of pieces associated with the passenger including carry-on baggage. The baggage is then directed to its proper loading zone in step 816. The handler may use a light-pen decoder with a miniature monitor to check the destination of the baggage with the light number. This is particularly convenient for the baggage sorting and direction/redirection of baggage to various destinations. This action will not only keep track of the baggage but also avoid improper loading caused by human error. In the automated model, a decoder may be installed at the conveyer belt of each airline to direct the baggage through swing gates to the appropriate conveyer assigned to a specific destination.

A boarding decoder validates the bar code on the boarding pass, step 818, and modifies the passenger s data from "CHECKED IN" status to "ON-BOARD" status, step 819. In order to avoid potential boarding of explosive materials intentionally concealed in baggage without the accompanying passenger, leading of the baggage while or after verification of passenger boarding will assure security. Bar code decoders in boarding terminal decoders and loading terminal decoders communicate with each other to avoid loading baggage without the passenger being on-board. Thus, upon boarding of the passenger the boarding terminal decoder sends the status to the loading terminal decoder, step 820. The status is received by the loading terminal decoder, step 821.

Once the baggage arrives at the loading zone, step 817, the baggage handler reads the code on the baggage using a loading terminal decoder, step 822, then the handler verifies the baggage code on every baggage against the passenger status, step 823, and the baggage of passengers not on board can be held outside of the loading zone until the passenger has boarded, step 824. A similar policy has been employed in some of the airports in Germany, however the process is performed by time-consuming manual examinations rather than via automated security and prevention systems like the tracking system set forth hereinabove. For boarded passengers, the baggage is loaded, step 825 while being verified, step 826. As an additional measure of security, the bar code may be used to seal checked-in luggage. Breaking of the code tape prior to loading the plane can be an indication of foul play. There have been situations wherein unattended luggage has been tampered with and has been used for breaching security by unsuspecting bystanders.

Figure 16:
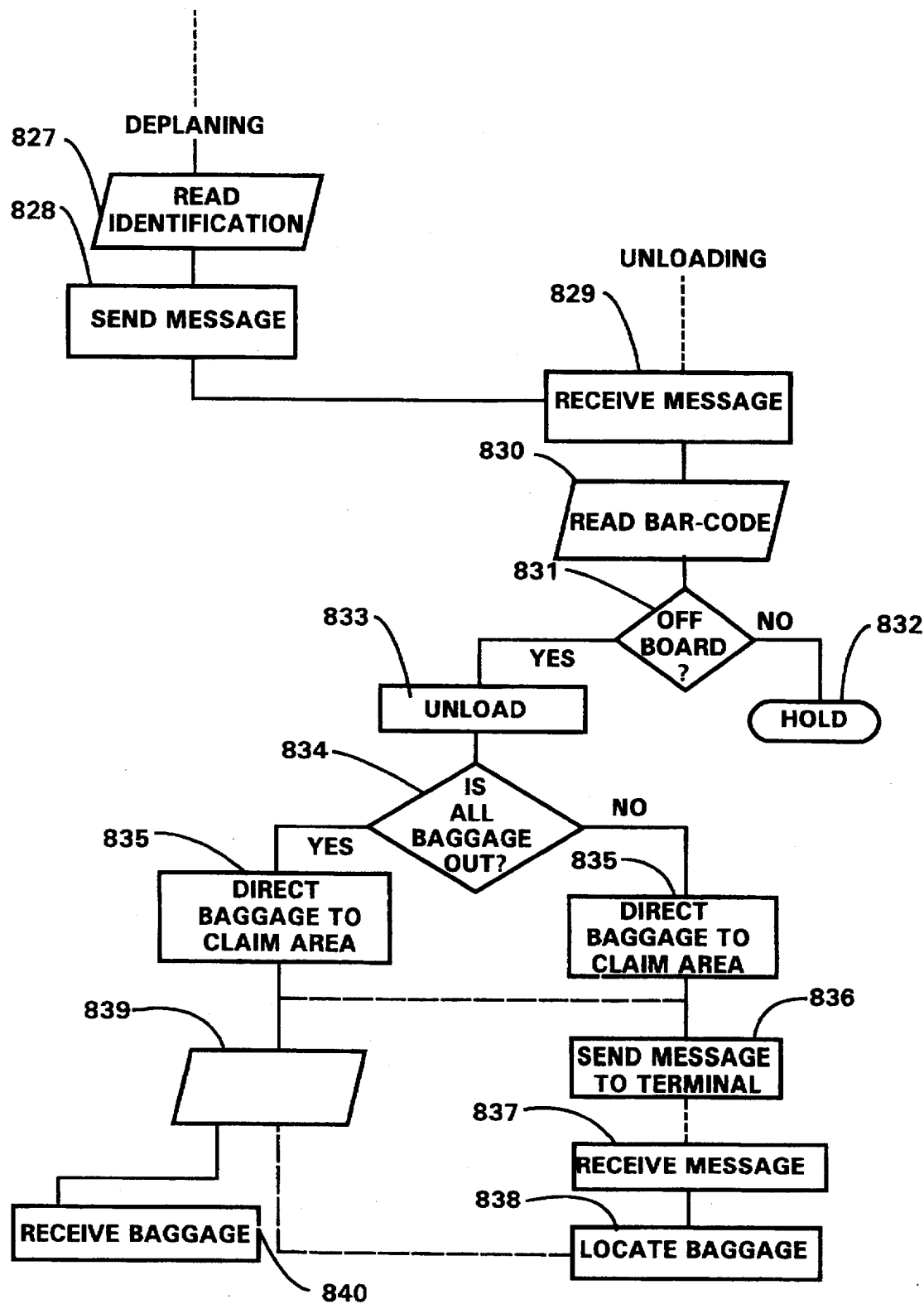
FIG. 16 is a logic diagram of the portion of baggage tracking system of FIG. 14 as it relates to procedures of passenger deplaning and the unloading and claiming of the associated baggage as well as the search and locate of lost luggage.

At deplaning, the procedure summarized by the flowchart shown in FIG. 16 is followed. A bar code on the ticket is read, step 827 and a message is sent to the baggage unloading terminal of the status of the passenger, step 828. Upon receiving the message, step 829, the bar code on the passenger s ticket is matched to the bar code specifics on the baggage, 830. To assure that the passenger cannot deplane without the associated baggage, the status of the passenger is verified against the baggage to be unloaded, step 831. If the passenger stays aboard, the baggage also stays, step 832, otherwise the baggage is unloaded, step 833. As an extra precaution, the number of baggages belonging to each deplaning passenger is verified, step 834. When all baggage is unloaded, the baggage is directed to the claim area, 835, and a message is sent to the area, step 837.

If all the baggage associated with a specific passenger can not be identified during unloading, the baggage handlers have to recheck the cargo area to trace the missing items. A message is promptly sent to the terminal, step 836, to alert the security as well as the claim area of the misplaced luggage. In case of continuing flights the airport security may have to hold the plane until the missing luggage is located to assure that the deplaning passenger does not leave an unchecked threat behind. Meanwhile, the identified baggage is forwarded to the claim area, step 837. At the terminal, the unlocated baggage is searched for until found, step 838. Locating misplaced baggage proceeds by electronic identification of the bar code sheet secured to the baggage. Not only airline personnel but also the passenger may be able to relocate misplaced baggage through the use of the tracking network.

At the baggage claim area, the bar code on the passenger's ticket is read and compared to that on the baggage, step 839, to assure receiving the proper baggage, step 840. The bar code attached to the baggage can be a certificate of baggage check-out. The baggage information is directed also to the central database to update the information from "UNLOADED" to "CHECKED OUT".

Considering the service aspects of air travel, a passenger may acquire information by presenting his or her ticket with a specific bar code through a desk-top bar code scanner in one of the local information stations located at critical points in airport. The information may include: time schedule of boarding; the number and location of the boarding gate; an introduction or a display map of the airport to show location baggage claim areas, restrooms, telephone booths and other airport facilities; weather; and information on the local city.

Figure 17:
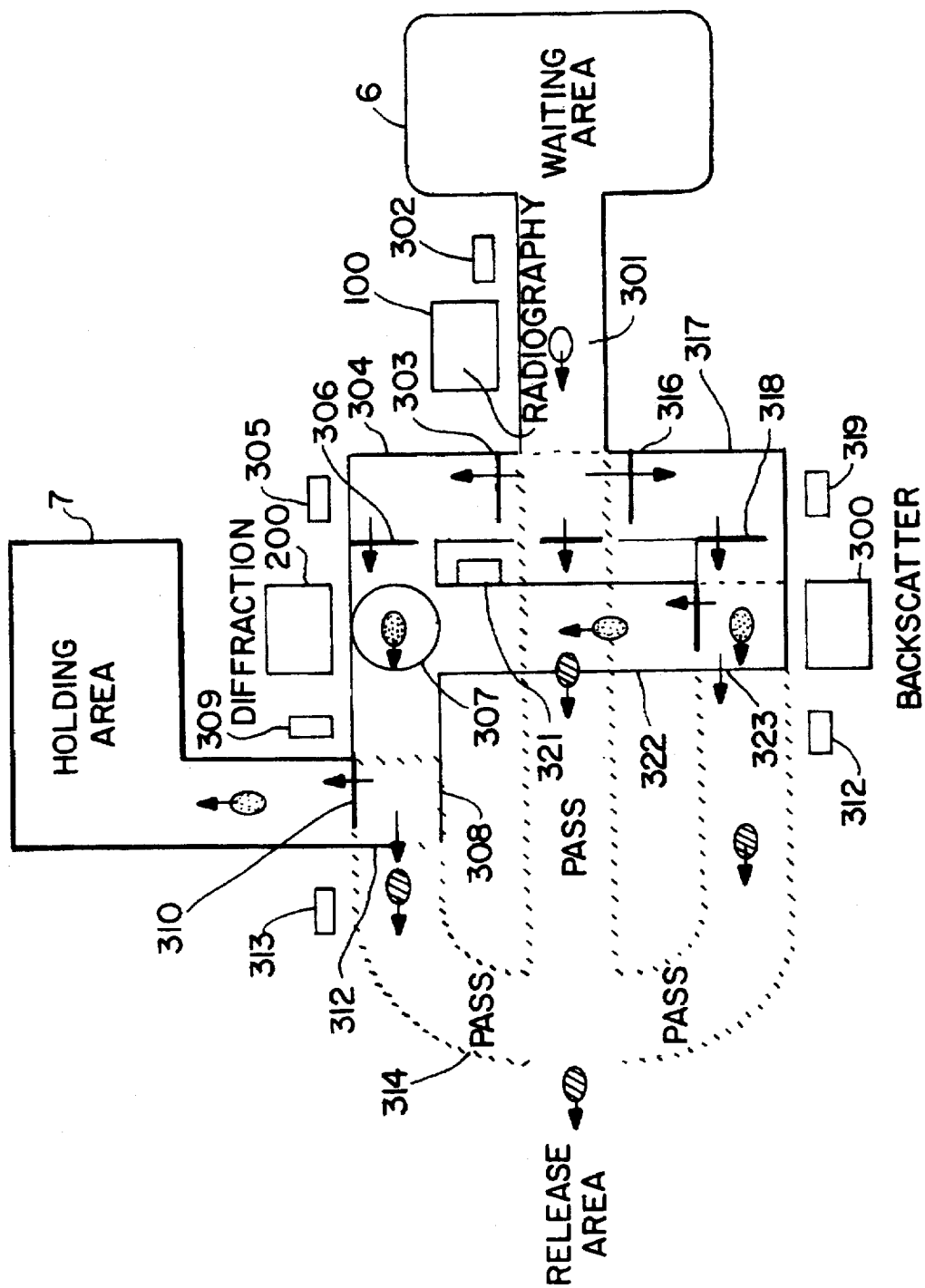
FIG. 17 shows a schematic top view of the screening system of checked-in baggage and cargo using the arrangement of FIG. 13.

The detection component of the second aspect of the invention is described by the top view schematic of the process shown in FIG. 17. In case of low density cargo or baggage as indicated by the radiographic imaging station, the baggage proceeds in the manner described in the case of carry-on baggage in FIG. 3. In fact, the system shown in FIG. 17 may also be used for light carry-on baggage. An article to be inspected at the waiting area 6, is placed on a lower level conveyer 301, the bar-code placed earlier at the coding center is read by the bar-code reader 302 and the information is sent to the microprocessor. Next, the baggage is examined by the radiographic unit 100, and the signal from the unit is sent for processing to the computer. An innocent article which does not appear to be dense continues to move on conveyer 301, crossing gate 315 which is normally open, and the article passes inspection and is released.

In case of an article which is not dense but is found suspicious or identified as a threat, the computer sends a signal to actuate relays on gates 303 and 306 to open, to actuate a relay on gate 315 to close, and to put conveyer 304 into motion and the article is directed to the diffraction unit 200 for analysis through gate 306 after recording its barcode in the reader 305. A turntable platform 307 is incorporated to provide the necessary depth information. Items would be scanned at a faster rate as they pass in front of the detection station on the conveyor and the interrogation cycle proceeds as presented in association with FIG. 3 for carry-on baggage. If the diffraction system identifies the article as innocent, the article proceeds to conveyer 314, crossing gate 312 which is normally open, its bar-code is recorded by the reader 313, and gets released. In case of identification of a threat at the diffraction unit 200, the computer closes gate 312, actuates a relay to operate elevator 308 which lifts the article to an upper conveyer 311 after opening gate 310, where the bar code is read by reader 309, and the article is apprehended at station 7 for further interrogation and action.

In case the baggage is identified as dense by the radiographic unit 100, gate 315 is closed and gate 316 is opened while conveyer 317 is set in motion. As the bar-code is read by the reader 319, gate 318 is opened and the baggage is interrogated by the x-ray backscatter system 300. Innocent dense baggage proceeds through gate 323 which is normally open and the bar-code is recorded in 312. A suspicious baggage is directed to conveyer 322 which is put in motion after opening gate 320 and closing gate 323 and the bar code is recorded by 321. The baggage is then examined by the diffraction unit in the same manner as before.

Figure 18:
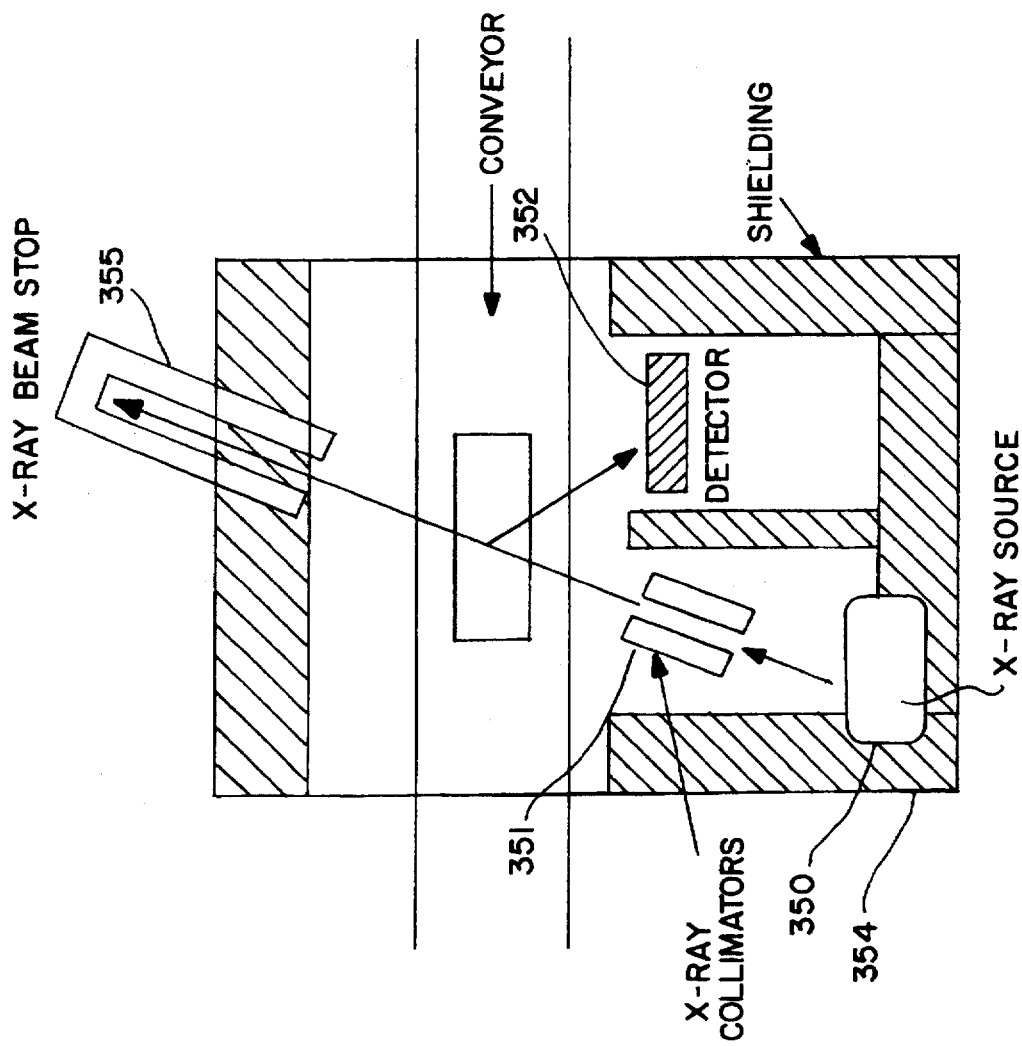
FIG. 18 schematically shows the radiation detector and x-ray source in an x-ray backscattering station.

The configuration of the x-ray diffraction is set forth in FIG. 4. The configuration of the x-ray backscattering unit is shown in FIG. 18 and comprises x-ray source 350, collimator 351, detector to detect backscatter rays 352 which is shielded from the source by shield 353, a perimeter shielding 354, and a beam stop 355.

When an electron beam is accelerated through a high voltage potential to strike a target (anode), x-rays are produced. The x-rays produced include a white radiation background (Bremmsstrahlung), and intense radiation at specific wavelengths characteristic of the target material. Since the x-rays appropriate for detection of hidden explosives in baggage or cargo must be highly penetrating, energies must be in the range of 100 to 160 kV. Since this is higher than the characteristic lines corresponding to any target material, one is limited to using the white background radiation, FIG. 19. Absorption of the x-ray beam is given by Beer s law, $$I/I_o = \exp(-\mu t)$$

where $I_o$ and $I$ are the intensities of the incident and the transmitted beams respectively, u is the linear absorption coefficient and t is the path length. The absorption coefficient may be estimated from the composition of the material and assuming a Victoreen dependence on wavelength at these high energies, $$\mu/\rho = C\lambda_3 - D\lambda_4 + \sigma NZ/A$$

where $\rho$ is the density of the material, C and D are constants to be determined for a specific material, $\lambda$ is the wavelength, $\sigma$ is the linear scattering coefficient, N is Avogadro's number, Z is the atomic number, and A is the atomic weight in atomic units. The backscattering x-rays will result primarily from Compton scattering, with an intensity proportional to, $$I/I_o \approx N^2 [e^2/mc^2]^2 AVP\Omega \left[ Z \sum_{i=1}^{Z} f_i^2 \right]$$

where A is the absorption factor, V is the volume of the scattering material, P is a polarization factor, $\Omega$ is the solid angle interception by the detector, and $f_i$ is the atomic scattering power. Since backscattering is very weak, as large a detector area as possible is desirable.

In the preferred embodiment of this aspect of the invention, scintillation detectors such as NaI detectors are used. Though they have poor energy resolution, they have high efficiency for the explosive detection application. Proportional gas counters can be made position sensitive and have moderate energy resolution, but have low efficiency at high energies. The efficiency can be increased by the use of xenon gas. Solid state detectors have high energy resolution but low efficiency and are rather expensive. The x-ray source is an array of x-ray tubes, each capable of producing a narrow x-ray beam. The tubes and the high voltage and power supplies being conventional items. The detectors needed for the backscattering measurement are manufactured to suit the particular application. Recently, large crystals have been produced for scintillators employed in whole body counting. Means to process the signals are similar to those used in health physics, radiology, and nuclear energy fields.

X-rays are appropriate for detection of hidden and concealed objects as well as in identification of the physical and chemical properties of unknown materials. This is due to their relatively short wavelength, provided that sources with sufficient intensity are used, for the rays to penetrate object to the desired depths. X-ray transmission (radiography) and tomography are feasible if the object is not highly absorbing. For highly absorbing objects, x-ray backscattering provides an alternative imaging method. Switching between two applied high voltages will change the energy distribution of the x-rays produced, resulting in improved contrast in the imaging of hidden objects. Use of multiple energies can further enhance the backscatter imaging and assist in discrimination between objects. A linear array of x-ray tubes, mounted in front of a slowly moving conveyor belt can provide the x-rays required for identification of hidden objects. By electronically switching between the linear array of x-ray tubes, the signal coming from the large area detector at any point can be identified with the x-ray backscattering from matter located in the beam of a particular x-ray tube. Output of the detector to a video display, coupled with the forward motion of the object will produce a two dimensional image of the backscattering from the object. Alternatively, detector output and storage in the video memory of a microprocessor would allow display and image processing of the observed x-ray backscattering.

The detection of objects in an interrogated area is based upon the difference in penetration depths. Scattering of incident x-rays depends on the material present and the atomic number of the constituting elements. Hence, a backscatter image is expected to show dark and or bright patterns with different degrees of brightness (gray scales or colors) that can be interpreted to identify the hidden objects as being a piece of metal, an explosive with a plastic casing or an explosive with a metallic casing, etc. In case of water-based explosives, the baggage "density" is measured, that is scanned from two (2) different directions. Given the volume of the object with the transmitted and/or backscattered x-ray intensity a measure of density becomes possible. Sheet explosives will be identified as suspicious in the x-ray backscattering and/or the radiography station of the detection system due to higher density (1.4–1.55 g/cm$^3$) compared with paper, fabric, and similar shaped materials which have substantially lower densities (0.7–1.2 g/cm$^3$).

Figure 20:
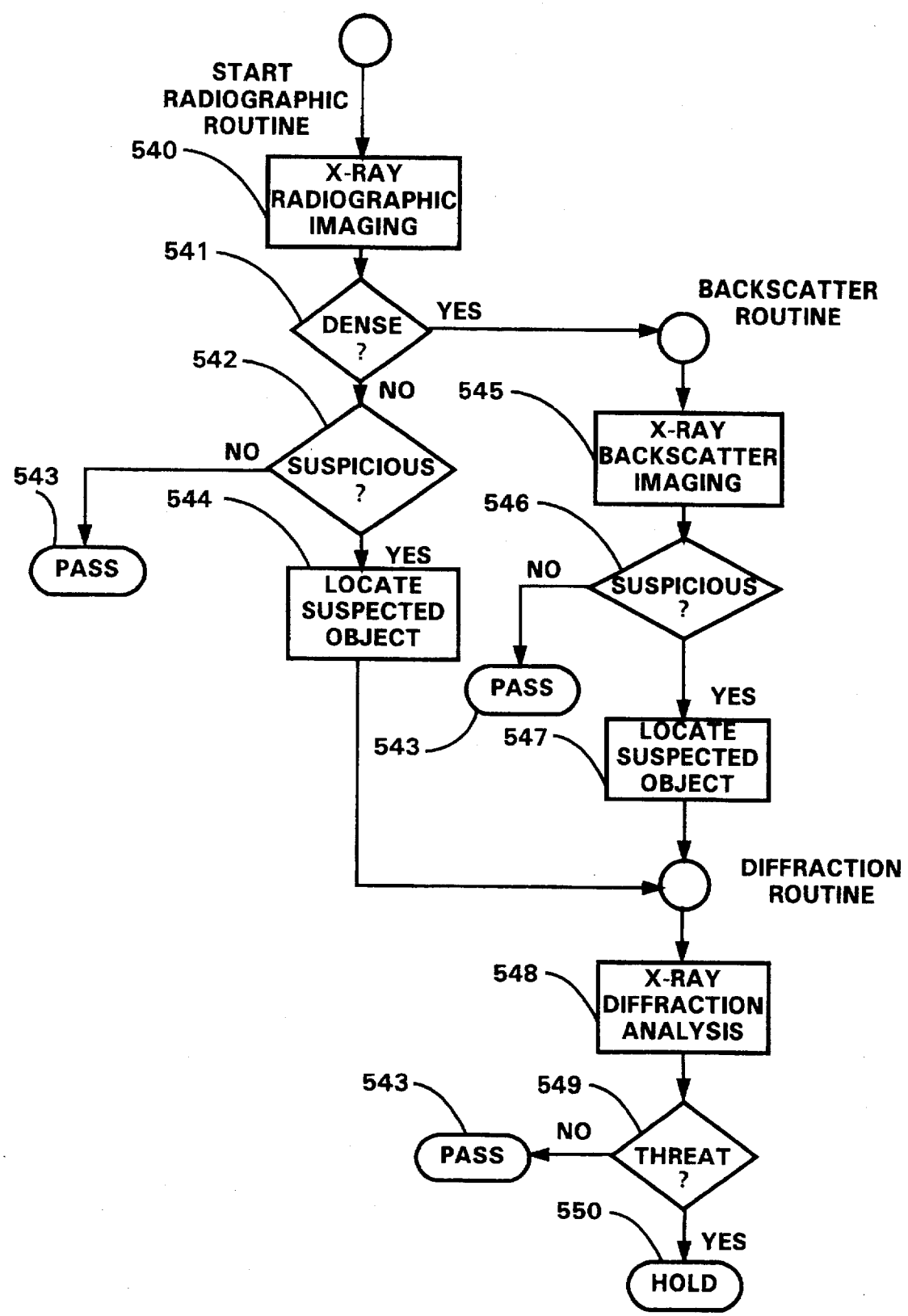
FIG. 20 is a flow chart of the logic of screening of checked-in baggage and air cargo.

A flow diagram of the procedure is shown in FIG. 20. The detection is divided into three routines, beginning with the radiographic x-ray imaging routine 540 for cargo and/or baggage. The first test 541 included in this routine concludes whether or not the item interrogated is too dense to be tested by the radiographic imaging. If the answer is NO, the baggage or cargo is tested in step 542 for detection of suspicious objects. The baggage is then routed to the PASS exit as in step 543 if innocent, otherwise the baggage is routed to the x-ray diffraction analysis routine in step 544. In case of dense cargo, the item is first routed to the backscatter imaging routine 545. In step 546, the results of the backscatter routine determines whether the item is suspicious or not. If NO, the baggage is routed to the PASS exit 543, otherwise the baggage is sent to the diffraction routine after one location of a suspicious object is defined by the computer in step 547. The diffraction routine 548 performs the final test in step 549 wherein the interrogated item is routed to PASS 543 or HOLD 550 according to the result of the analysis. The different routes are controlled by signals fed from the computer to the relay switches controlling the successive exit doors, conveyers and elevators as set forth hereinabove.

Considering the data processing system, instead of applying the picture to a monitor directly, it is fed to a microcomputer via an analog-to-digital converter (ADC), or a video digitizer as an alternative. The input picture is compared to templates which are pre-stored in the PICTURES DATABASE, in the computer external storage. The templates contain threats (firearms, grenades, incendiary and explosive devices, or pure incendiaries and explosives, etc.) in different positions. The parameters on the templates differ from one detection system to the other. With backscatter or radiographic routines, they are 2-dimensional binary pictures representing the intensity of every pixel in gray scales, while with the diffraction routine, they represent the diffraction patterns of different threats. If a match occurs between the input picture and the reference template, the response may be an audible alarm or an audio/video alarm. In addition control signals will be sent to swing gates to control routes of the examined baggage and cargo in the lines of detection.

Matching the x-ray images with the reference template in case of x-ray backscatter imaging and/or radiography involve using commercially manufactured explosives can be used to generate templates based on shape and intensity—e.g. a stick of dynamite. These templates will form the initial knowledge base which may be further developed based on experience gained in operation of airport scanning systems to identify other explosives. In both cases the observed patterns are analyzed to find clues that can help determine the features of the image; such as color or shades of gray, depth, texture and motion. The clues may be found by a stereoscopic picture using two sources, or capturing a series of images of the moving target (baggage). Once the digitized image is analyzed, the constituents are identified by techniques; such as edge detection and model-based vision.

Figure 21:
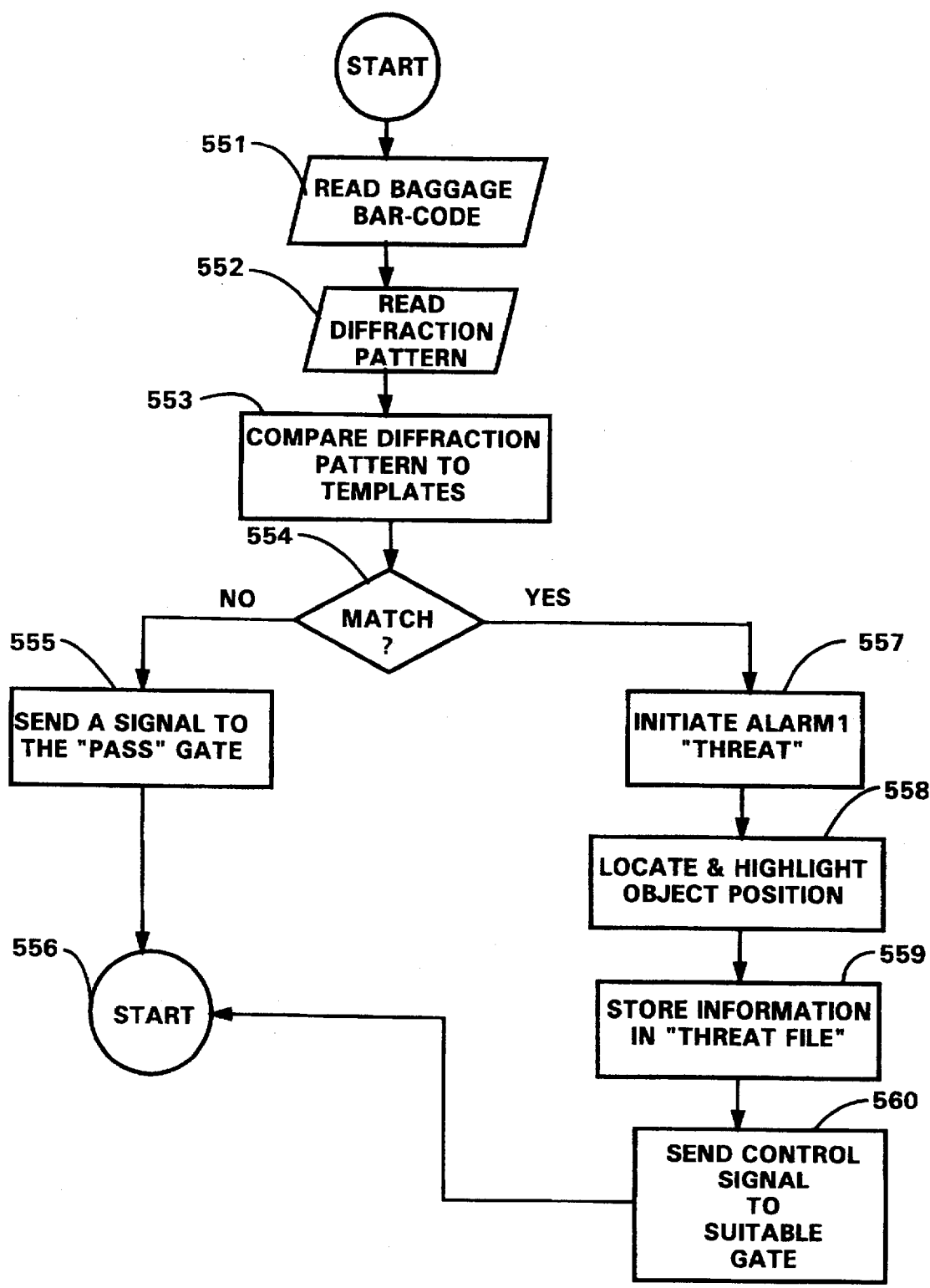
FIG. 21 is a flow chart of the logic of diffraction interrogation stage.

Matching with powder patterns is presented above. FIG. 21 shows a system flowchart of the diffraction detection process wherein the baggage bar code is read 551, and the diffraction pattern is read 552 and compared with templates 553. If no match is found in the matching step 554, a signal is sent to the PASS gate 555, otherwise alarm is initiated 557 and the threat is localized and highlighted 558 while the information is stored in the threat file 559 and control signals are sent to suitable gates 560.

Figure 22:
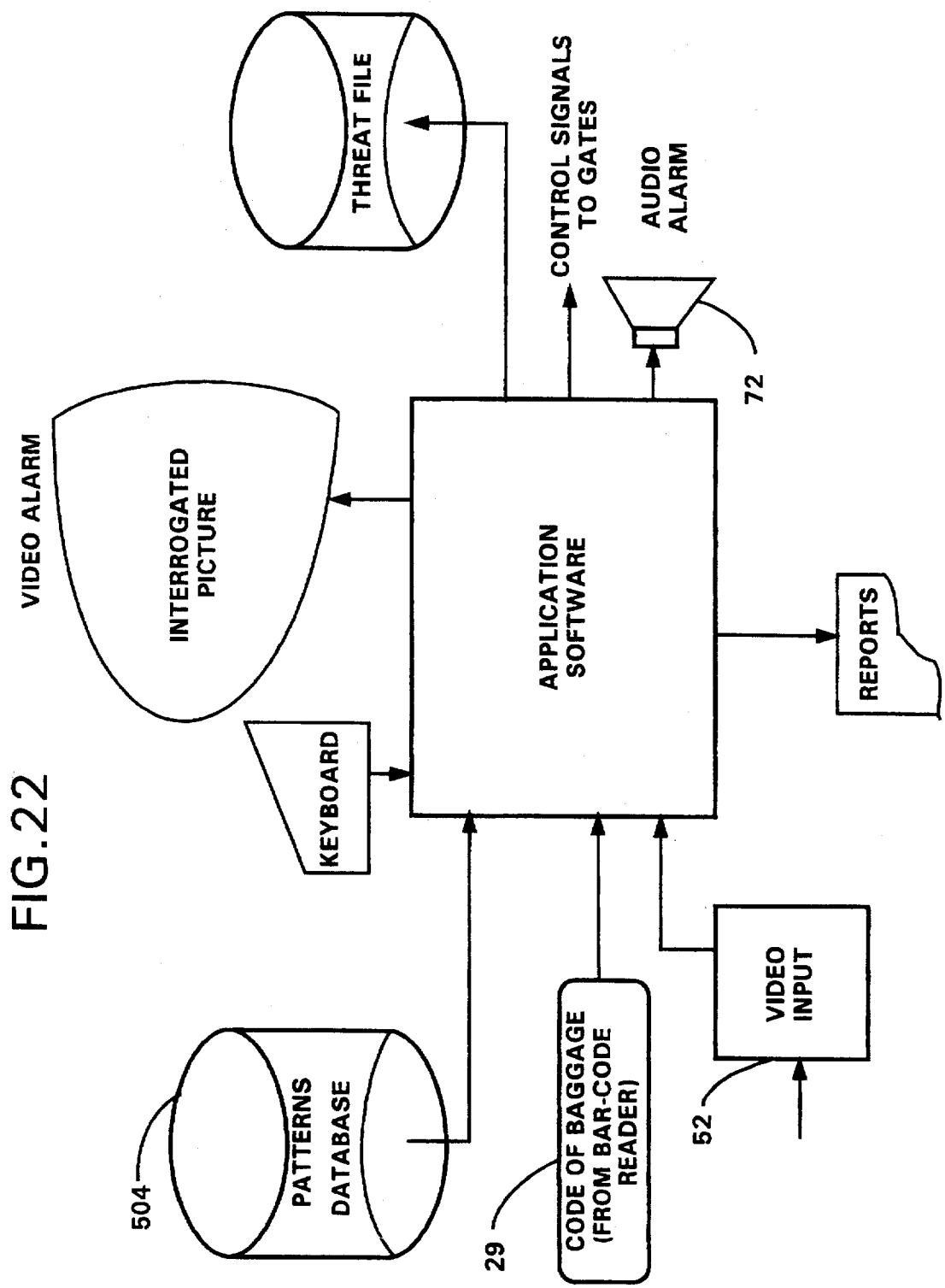
FIG. 22 is a schematic of the functional process of diffraction pattern analysis.

FIG. 22 shows the procedure for comparison with diffraction pattern templates of pictures generated from the diffraction analysis signals. The inspection procedure starts with comparing the interrogated picture input as a video signal 52 with the templates previously stored in the pictures database 504. If a match occurs, then an audio alarm is initiated by the program and fed to the loudspeaker 72. This alarm means that one of the previously specified threats is located. The location of the threat object is defined and the picture is saved in the "threat file" 501 as well as the necessary information such as the bar-code of the baggage/cargo 29 is received from reader 309 and the location of the object. Such information will be helpful when the baggage is manually inspected by the authorized person, as the picture can be retrieved and the position of the threat-object is highlighted in order to enable the inspector to go directly to the required object and take the necessary precautions. The bar-code is also useful in identifying the bag at the gates. This is done by sending the signal to a certain gate combined with the bar-code of the specific baggage or cargo. In this case, the gate is opened only after the bar-code is verified.

Figure 23:
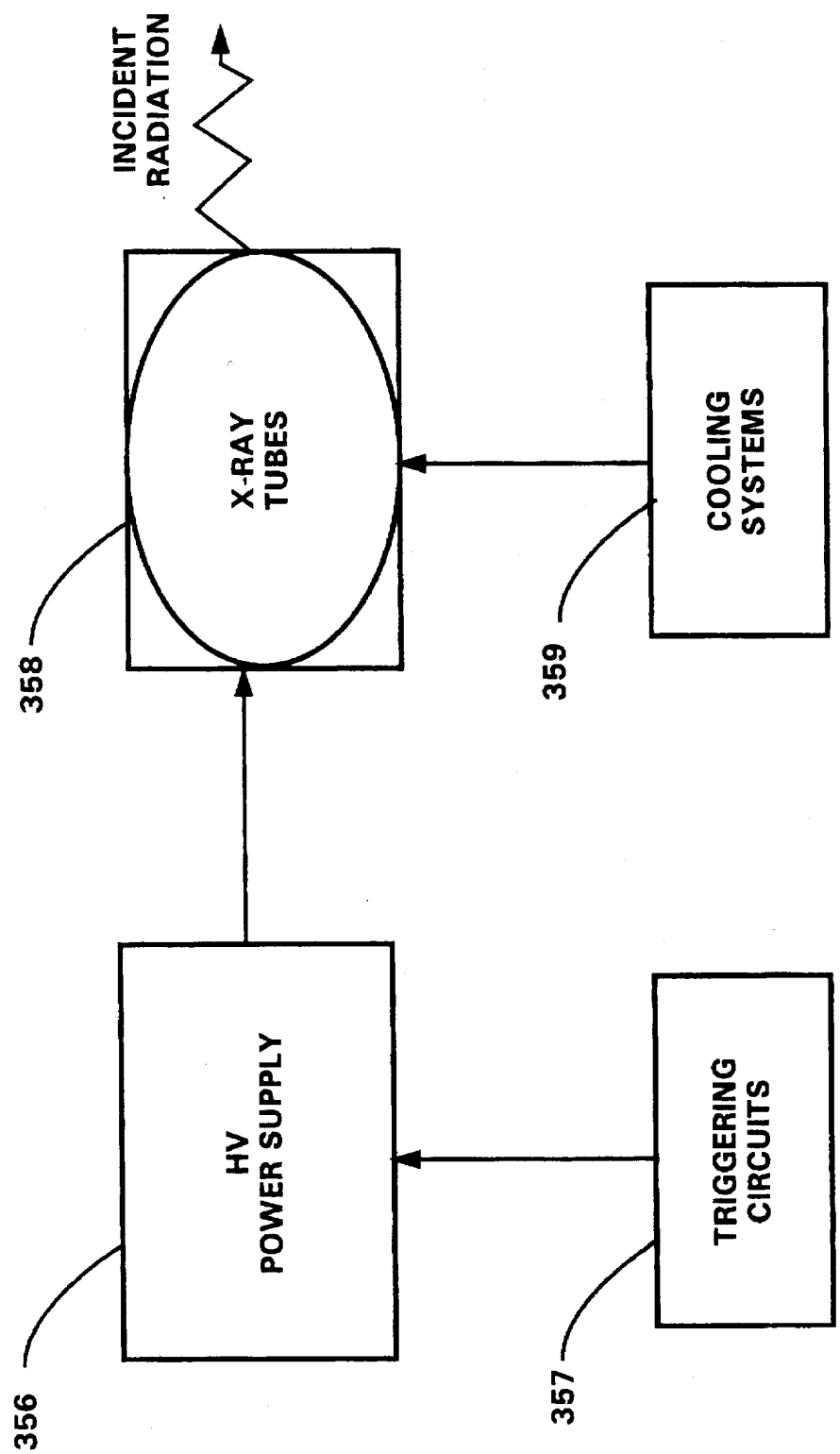
FIG. 23 is a block diagram of the x-ray production system for the backscattering unit.
Figure 24:
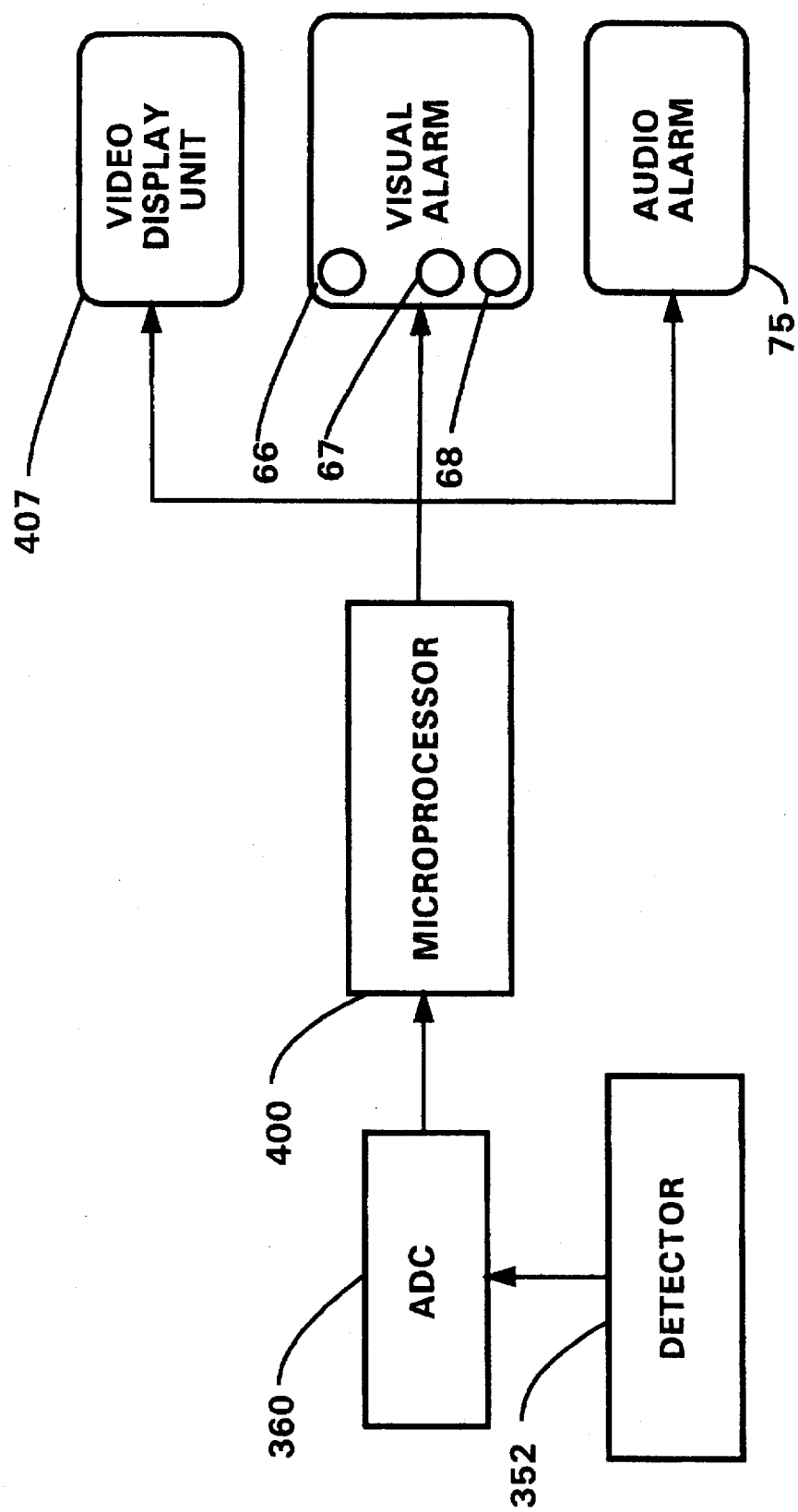
FIG. 24 is a block diagram of the detection and imaging processing of the backscattering unit.

The backscattering unit is a dual-energy x-ray backscatter imaging system for rapid interrogation of highly absorbing baggage and cargo. The source FIG. 18 is mounted in front of a conveyor belt travelling at a speed of 0.35 meter per second (14 inch per second) interrogating an area of 1.5 meter width. The x-ray system contains 120 tubes successively fired one after the other to supply a peak power of 100 kW for a pulse duration of 100 microseconds. Switching tubes between two high voltage pulses (120 kV and 160 kV of 1,000 mA) occurs for alternate pixels, implying a switch rate of 4,500 per second. X-rays are collimated to produce an illuminated spot on the object of about 1 cm in diameter. A large scintillation single crystal detector, NaI(Tl) is used. The output of the NaI(Tl) detector is mapped into the memory of a computer and fed to a visual display unit giving an image of the interrogated area to identify the location of possible explosives. An integrated functional diagram of the backscatter x-ray production system is depicted by FIG. 23 which basically comprises a high voltage (HV) power supply 356, triggering circuits 357, x-ray tubes 358, and a cooling system 359. The detection and image processing system is shown in FIG. 24 which comprises a video display unit 407, a visual alarm with green light 66, amber light 67, and red lights 68, and an audio alarm 75 as outputs from a processor 400. The input signal from detector 352 are acquired through an ADC 360.

Figure 25:
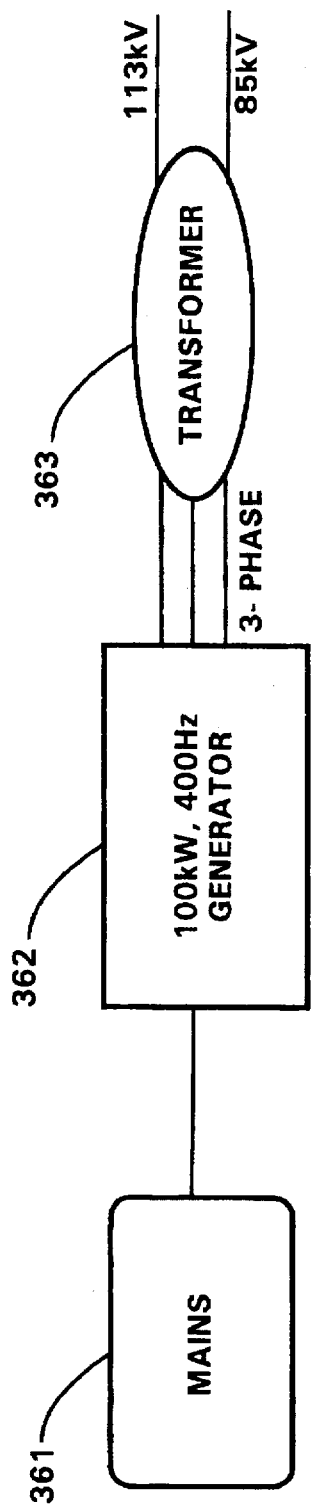
FIG. 25 is the power supply arrangement for the backscattering unit.
Figure 26:
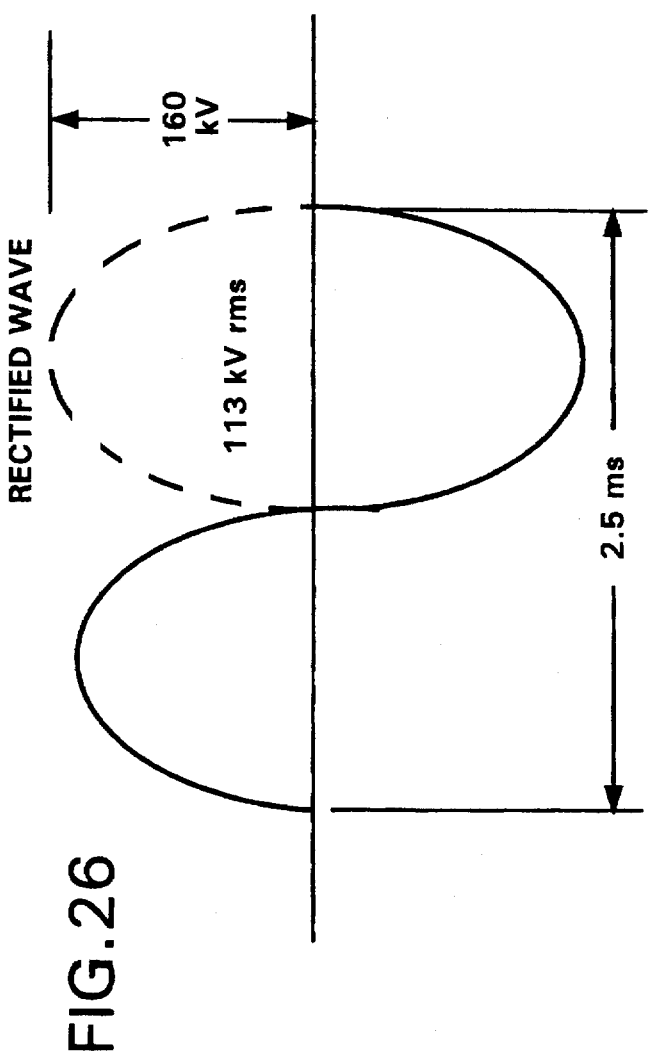
FIG. 26 is a waveform of the input of the power transformer of FIG. 25.

A block diagram of the arrangement of the main power system shown in FIG. 25 may consist of the mains 361, a 400 Hz±10%—generator 362 comprised of class 3-phase transformer capable of carrying the full average power of roughly 100 kW; a 24-phase power transformer with each phase capable of carry 1 A and a peak power of 100 kV for 0.1 millisecond, and a full wave 3-phase HV rectifier bridge. The 400 Hz transformer 363 will contain two-electrically isolated but magnetically coupled HV winding with predetermined center taps. One secondary is used for the odd-numbered set of x-ray tubes, namely tubes #1, 3, 5 . . . , 119. The other secondary is used for the even-numbered set of x-ray tubes, namely tubes #2, 4, 6, . . . , 120. The maximum peak voltages of these secondaries will be in the ranges of 160 kV or roughly 113 kV root mean square (RMS); and 120 kV or roughly 85 kV.RMS respectively. The phase skirt of each phase is 15 electric degrees. Thus, a 24-phase with 7.5 electric degrees can be achieved. The output wave shape form of the power supply output is shown in FIG. 26.

Figure 27:
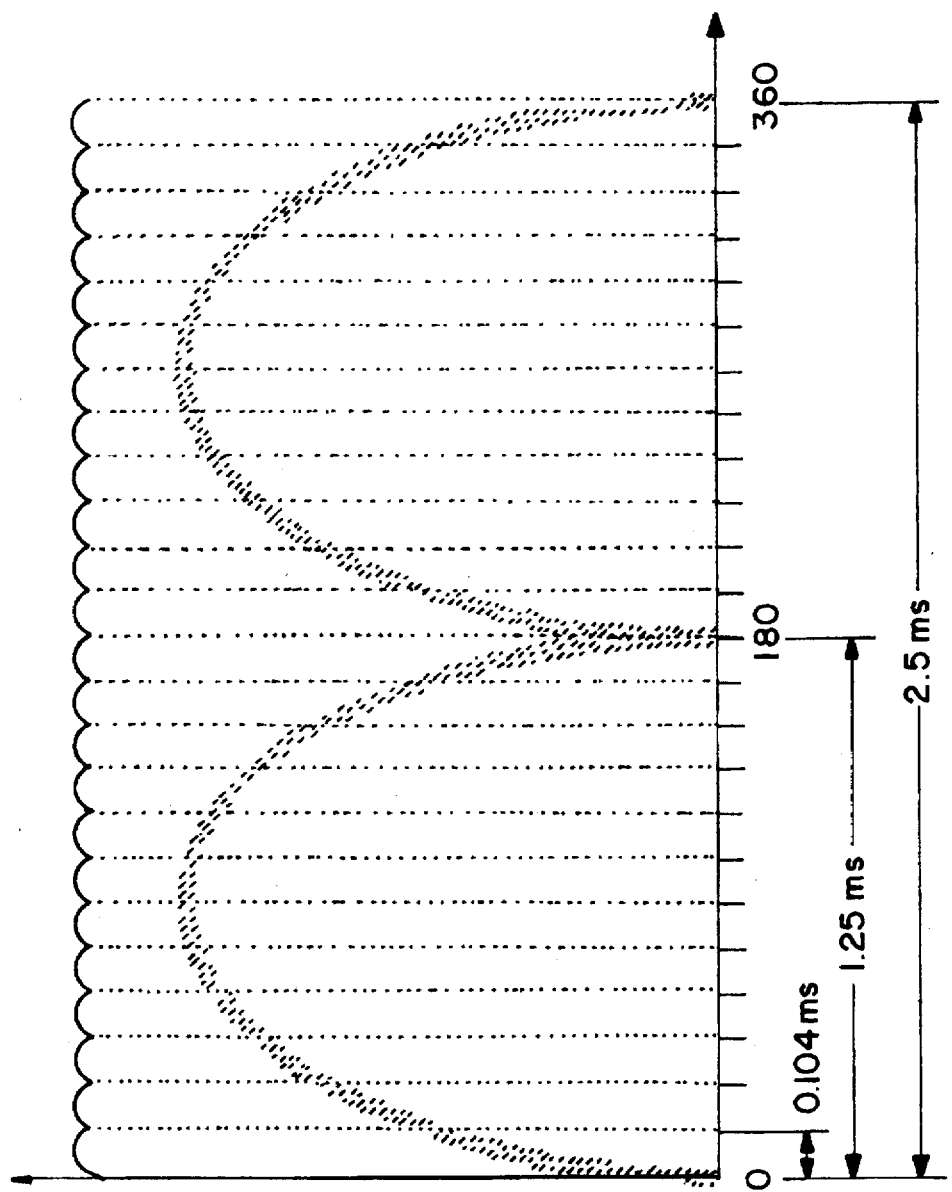
FIG. 27 is the waveform of the output of the power supply of FIG. 25.
Figure 28:
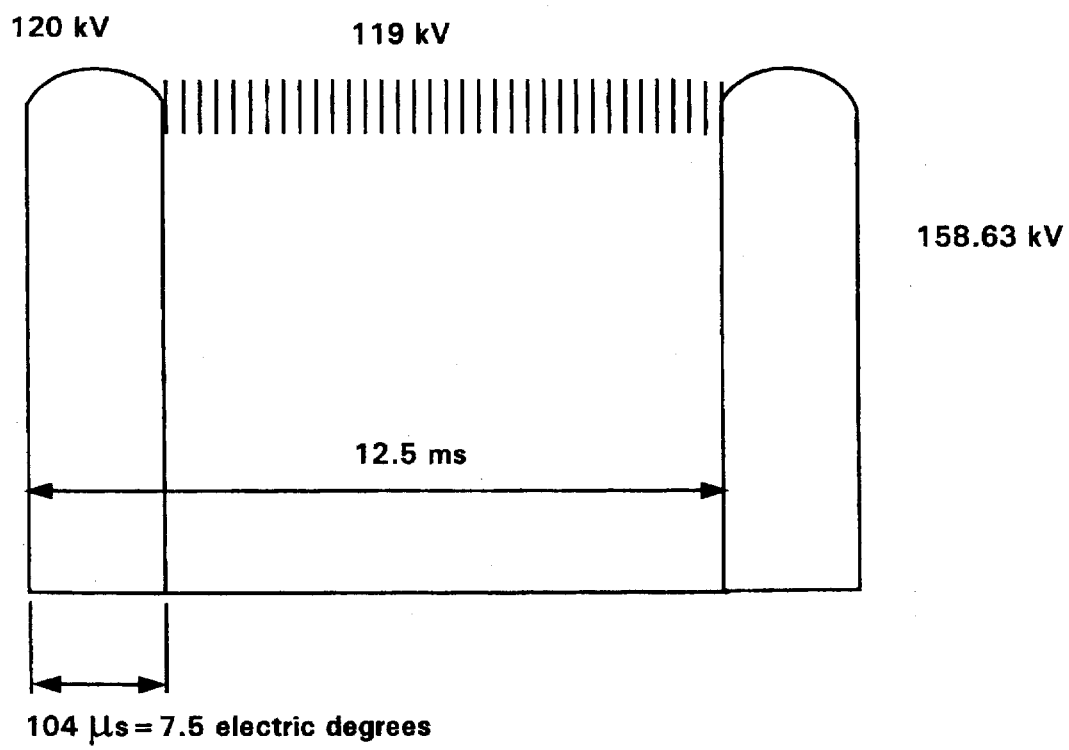
FIG. 28 is the output of the power supply and switching stack for 120 kV.
Figure 29:
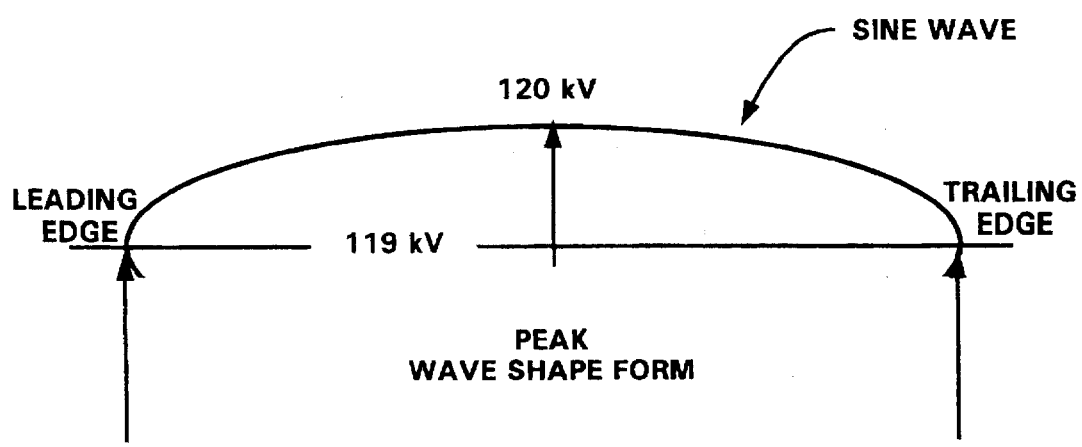
FIG. 29 is the wave shape form of each pulse for 120 kV.
Figure 30:
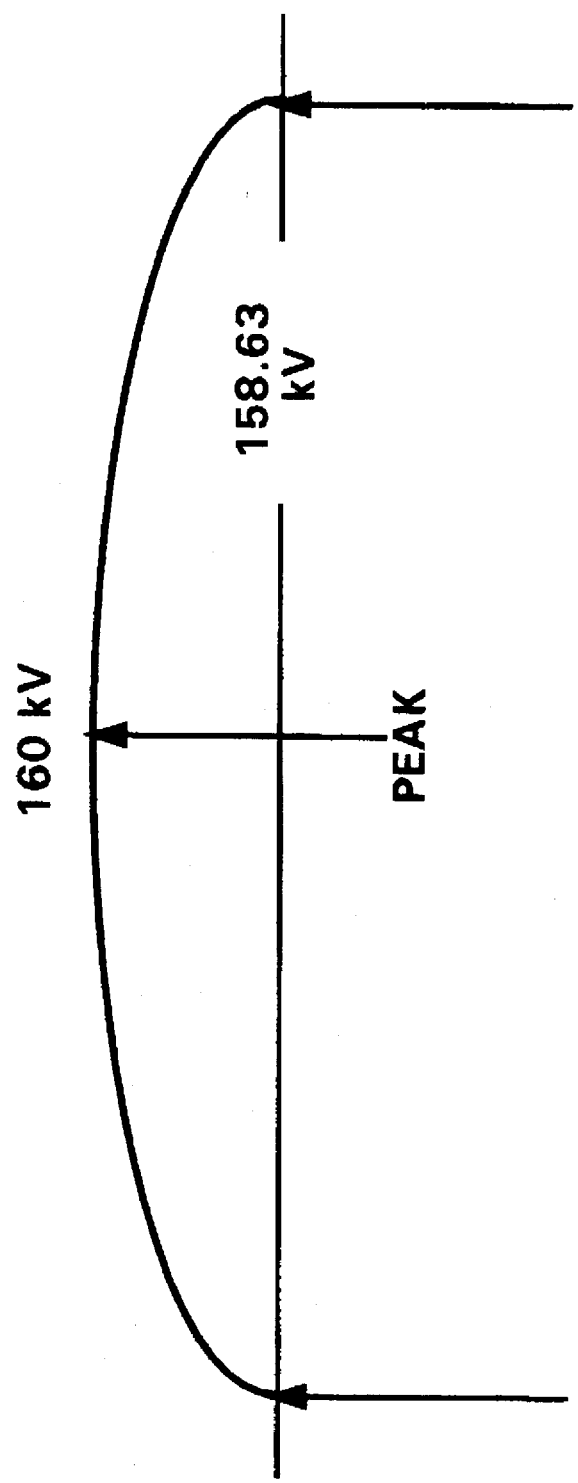
FIG. 30 is the shape of the wave form of each pulse for 160 kV.

Each of the full rectified output voltage waveforms will be 0.104 millisecond. The output of the power supply is shown in FIG. 27. When combined with the stack of switching devices, the output of the power supply will be as shown in FIG. 28; where 7.5 electric degrees at nominal 400 Hz frequency is equivalent to 104 microseconds. However, a 100 microseconds can be exactly obtained by a slight change of the main generator speed. This will also reduce the cycle to 12 milliseconds. The wave shape form for each pulse is shown in FIGS. 29 and 30.

Figure 31:
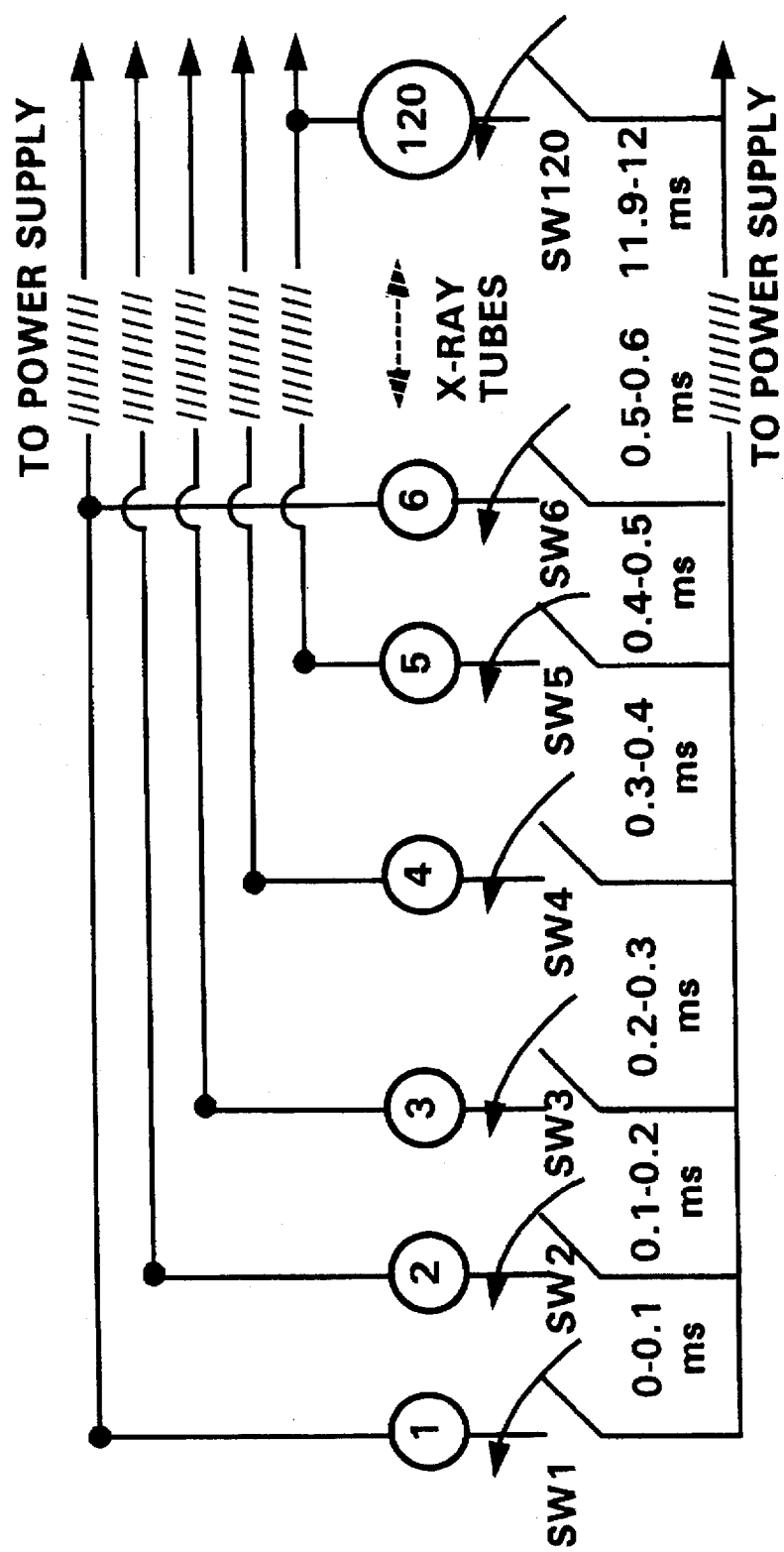
FIG. 31 show the circuit diagram of the distributed switching system.
Figure 32:
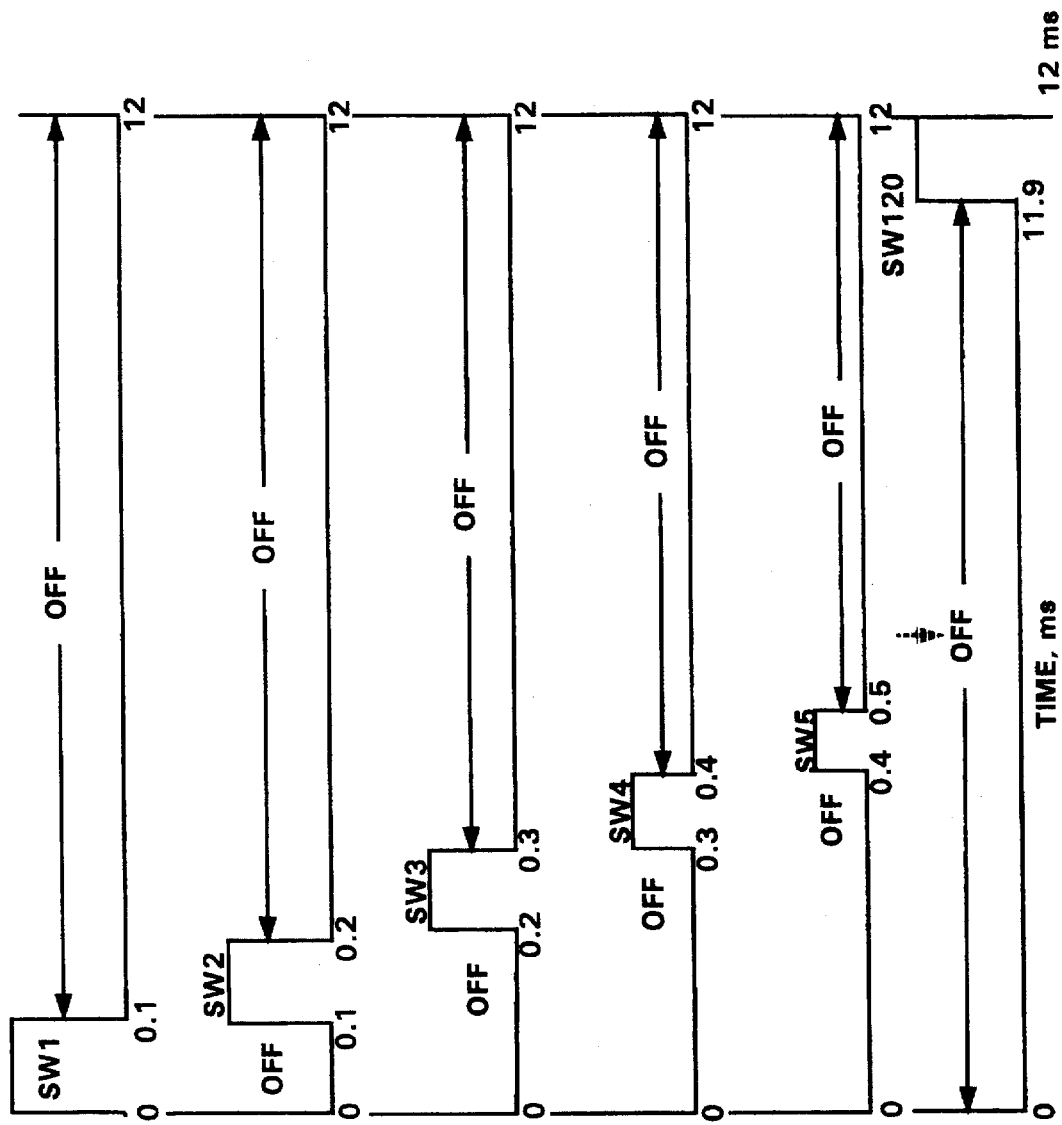
FIG. 32 shows the switching sequence.
Figure 33:
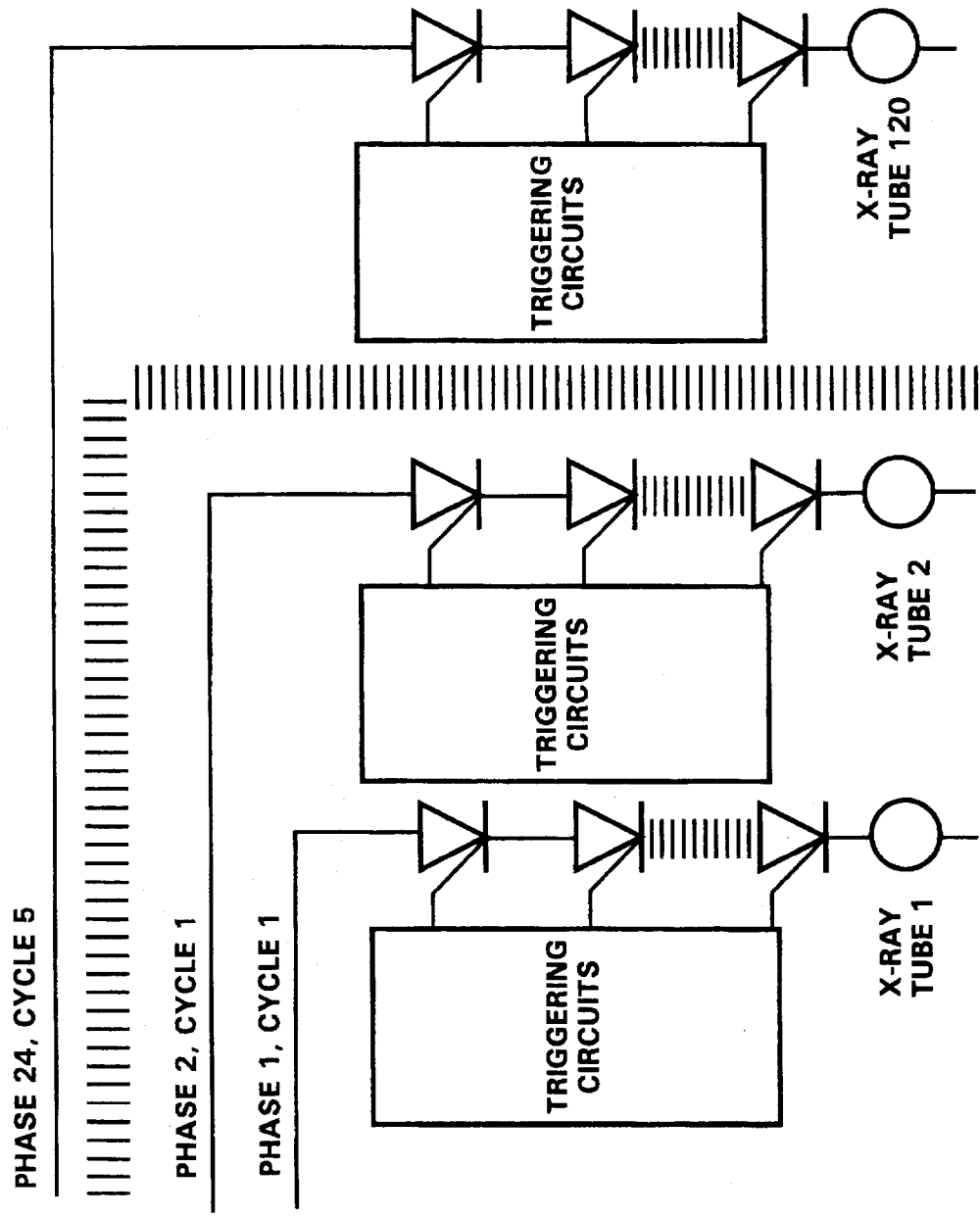
FIG. 33 shows the triggering system.

The switching system is simplified in FIG. 31. As shown in FIG. 32, each switch (SW) is closed or tuned on for a period of 100 microseconds (0.1 millisecond) and must be off for a theoretical period of 12,000 microseconds (12 millisecond). Thus, SW1 will be on from 0–0.1 millisecond and off for 11.9 millisecond, SW2 will be on from 0.1–0.2 millisecond and off for the rest of the period and while SW1 is on, etc., SW120 will be on from 11.9–12 millisecond and off for the rest of the cycle. The odd numbered switches will be connected to a lower energy source of 100–120 kV and the even numbered to a higher energy source of 120–160 kV. The switching system employs a distributed switching approach. As shown in FIG. 33, each branch will be equipped by a separate stack of suitable solid state switching devices. The switching system and its power supplier are compact, reliable, and reasonably light weight. This is achieved by use of solid state devices. The advantage of the distributed switching system is its natural and much simpler commutation and control of all the switching valves. Silicon controlled rectifiers (SCRs) are the most appropriate switching device for this system, although HV power transistors or gate-controlled switches may also be used as well as some of the more common triggering circuits. Synchronization is programmed by microprocessors to produce appropriate scanning for each x-ray tube. Light activated, xenon flash and fiber optics are utilized for HV isolation. Commonly available delay circuits are also incorporated. To isolate the various gates, commercially available pulse transformers may be used. Once the triggering circuits are synchronized and programmed, the sequence of tuning on and off the 120 x-ray tubes can be easily achieved.

Several alternate embodiments are available, including variations on the switching system design, x-ray tubes size and arrangements, or the use of alternative components. Those are given here for consideration of simplifying the design, reduction of the cost, and/or providing alternate means to achieve the performance goals. The alternate voltage switching system has exactly the same circuits as FIG. 31; however, energizing the odd-numbered set by the 120 kV is followed in the next scanning by application of the 160 kV. Similarly the energization of the even-numbered set will alternate between 160 kV and 120 kV. This scheme is, in principle, preferable to energizing each set by only one voltage source.

Figure 34:
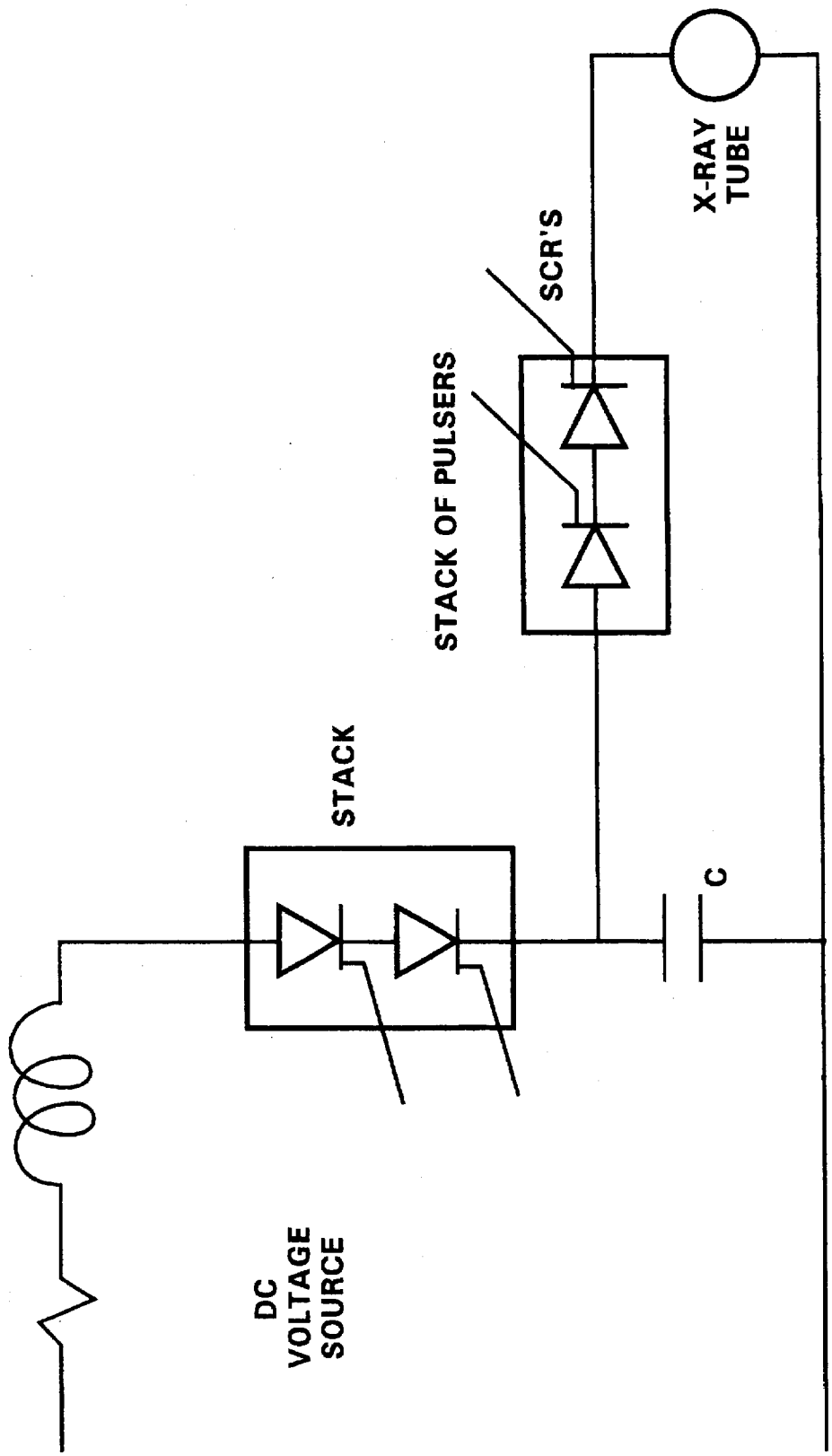
FIG. 34 shows an R-C pulsed switching system.
Figure 35:
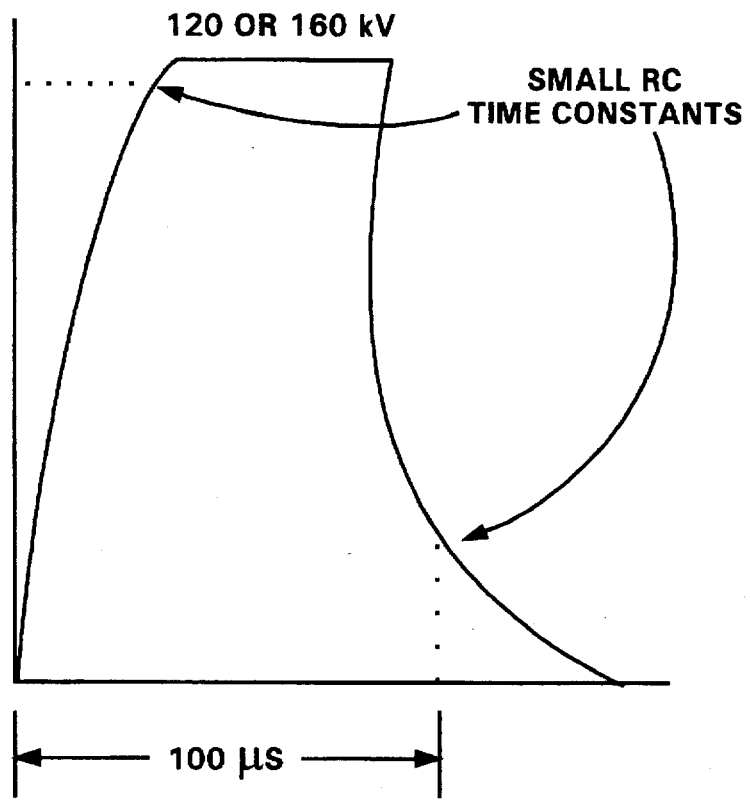
FIG. 35 shows the waveform of the R-C pulsed switching system of FIG. 34.
Figure 36:
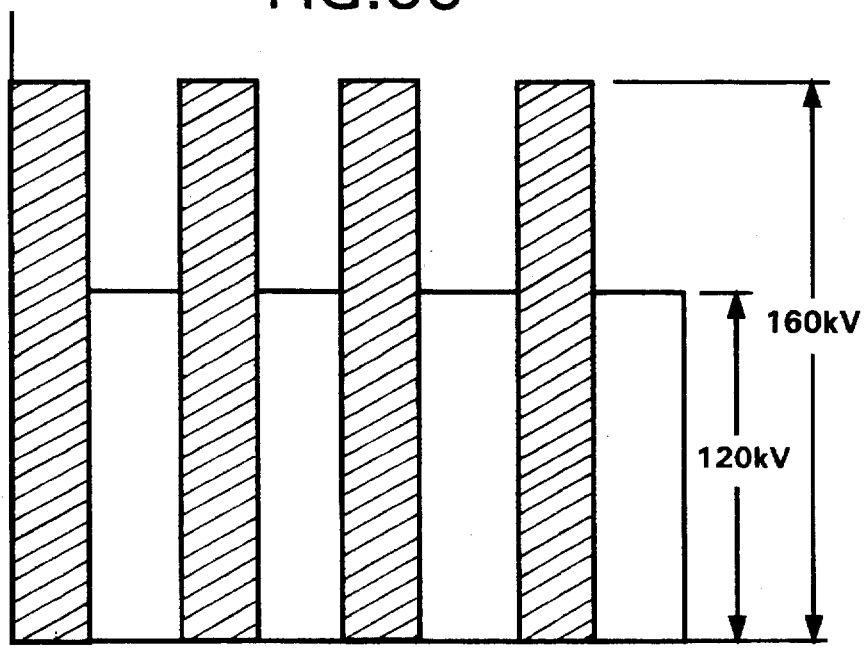
FIG. 36 shows the waveform of a centralized switching system.

The R-C pulse switching system circuit shown in FIG. 34 may also be used with a general arrangement similar to that of the distributed system of FIG. 31, with the exception of charging a capacitor for each branch (or each x-ray tube circuit). The capacitor in FIG. 34 is discharged whenever needed. The output waveform shape across the tube is approximately rectangular with an R-C time constant as shown in FIG. 35. A third alternate embodiment is the centralized switching system, wherein the main power source is a combination of the nominal 400 Hz generator, a 3-phase HV transformer with center taps and two HV secondary windings and a high voltage bridge rectifier to separately produce 100–120 kV DC and 140–160 kV DC. The design of the switching system is then converted to the design of an inverter HV circuit that will produce a 120 kV (or 160 kV) pulse with an approximate width of 100 microseconds. The output voltage waveform includes more harmonics and the triggering circuits are more complex. FIG. 36 shows the waveform without the harmonics.

Various switching devices may also be used such as gate controlled switches (GCS), light activated switches, HV and high gain silicon power transistors. Furthermore, the switching frequency may be reduced to a rate of 67/s, that is the switching would occur for every other sweep of the x-ray source (alternative scanning lines).

Water cooling is a preferred candidate for ameliorating the effects of power dissipation, however, proper grounding in this case becomes a major factor for safe and reliable operation. Liquid metal and pressurized gas cooling is also a possibility. Cooling may be enhanced by using a rotating anode and the use of magnetic seals. Protection of personnel against radiation is a standard procedure. Conventional shielding is appropriate. For protection from high voltage, Xenon flash and fiber optics may be used.

Figure 19:
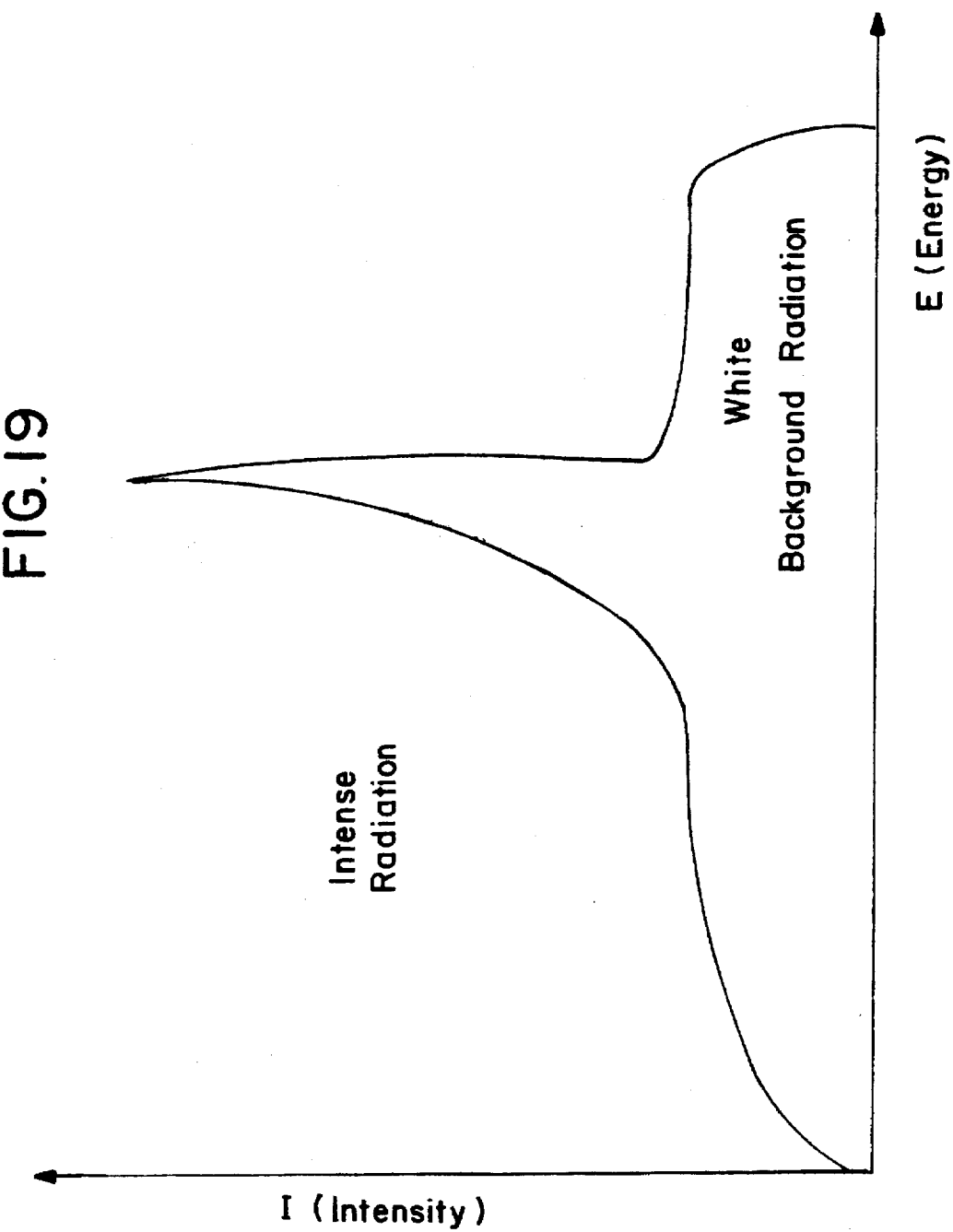
FIG. 19 is a display of a typical x-ray intensity-energy relationship.
Figure 37:
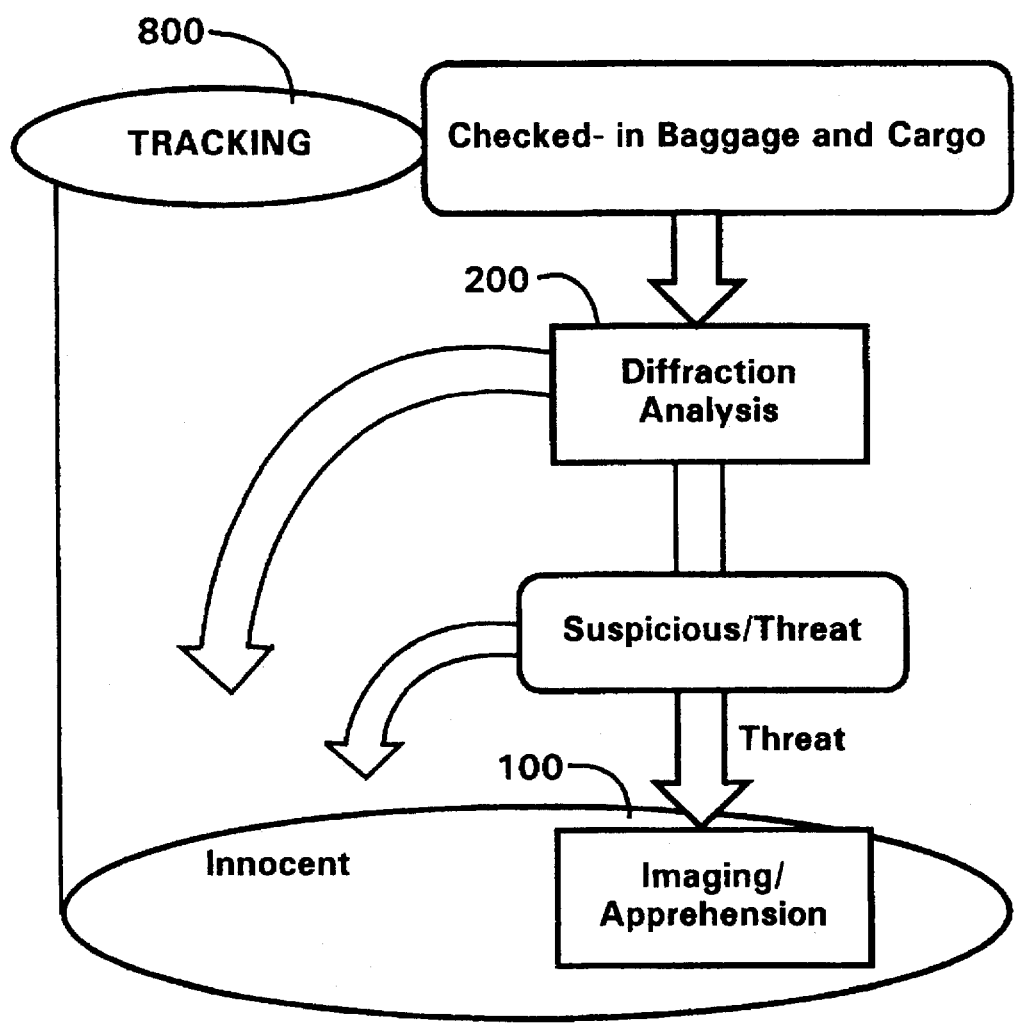
FIG. 37 shows a flow chart of an alternative arrangement for an integrated x-ray diffraction system for detailed interrogation and x-ray radiography system for locating threats and screening checked-in baggage and cargo.

A simplified embodiment of the second aspect of the invention provides a non-vapor, non-nuclear explosive and contraband detection system for dense checked-in baggage and/or air cargo excludes the backscattering stage of FIG. 19 and utilizes the x-ray diffraction as the main screening unit while delegating to the radiographic imaging the localization of the detected threats. This embodiment process the units at a slower rate than in the more complex system which may be in the neighborhood of one unit per minute, however higher detection probability is expected. The flowchart of this embodiment is shown in FIG. 37. The baggage is first checked by the diffraction analysis station 200 and only suspicious items or threats are directed to the imaging 100 for apprehension. The tracking system of FIG. 16 may be used in parallel with this process.

Figure 38:
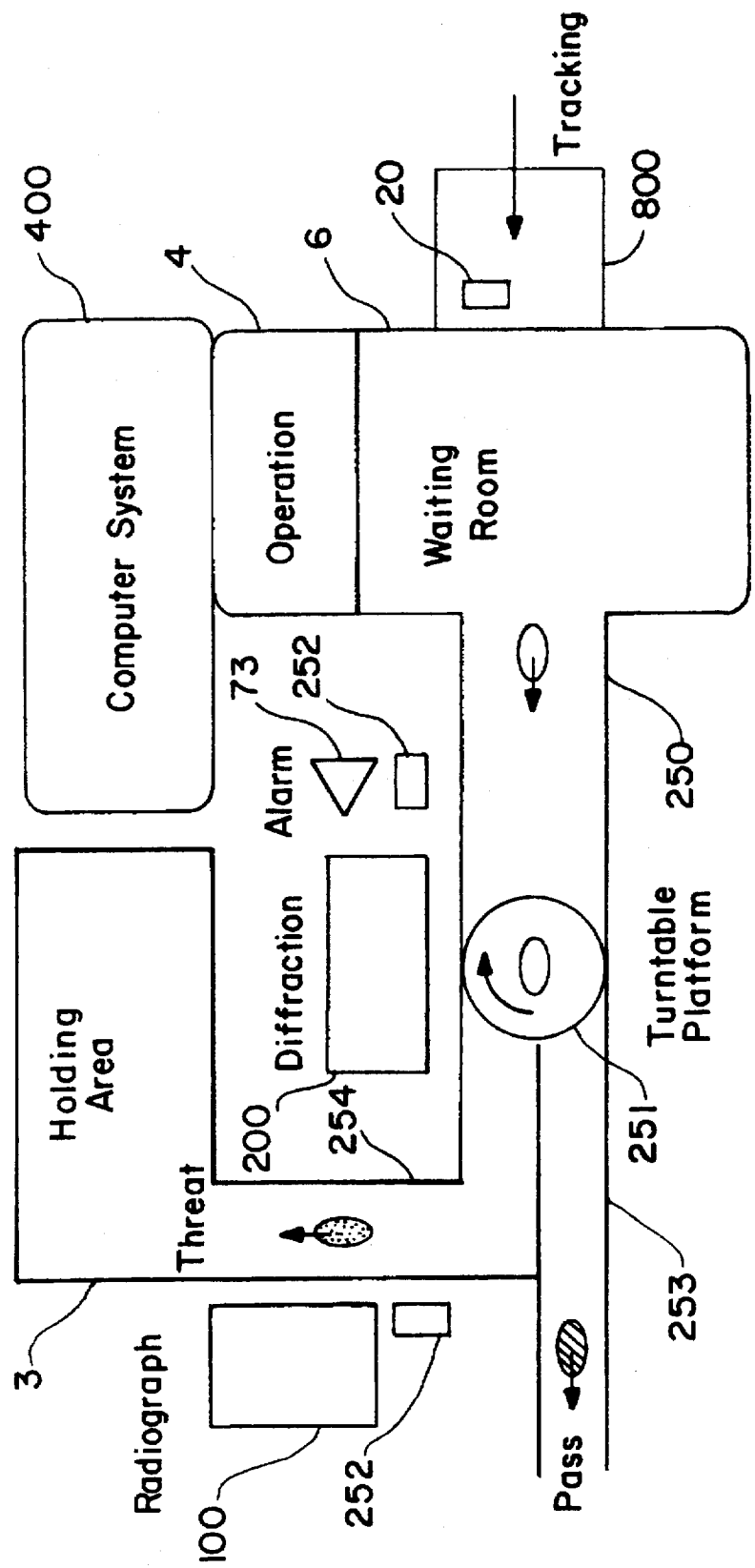
FIG. 38 is a schematic top view of the layout and the process flow of the explosives detection system for dense checked-in baggage and air cargo of FIG. 37.

The layout and the flow of the detection process is shown in FIG. 38. All items are directed by a conveyer belt to a waiting room 6. An article is directed first to a bar-coding unit 20 where a bar code is placed on the item either manually or automatically. As a bar-coded article is ready for interrogation, the bar-coded article is moved to a COMMON conveyer belt 250 out of the waiting room 6, and is directed to a turntable platform 251 in front of an x-ray diffraction unit 200, for interrogation by the diffraction routine to identify any threat and specify its location and to relay the results to the process computer 400. The diffraction unit 200, and the computer system 400 are connected to a bar-code reader station 252 which reads the bar code on the article prior to interrogation.

At the x-ray diffraction station 200, the object to be inspected is positioned on the rotating platform 251 for interrogation of one side. After the first interrogation cycle is completed, a computer signal from the computer system 400 sets the platform 251 in motion and rotates the object 2 (baggage/cargo), 90°, then 180°, and then 270°. The rotation occurs until all quadrants of the object are interrogated, whether or not a threat is detected at one of the earlier cycles. This is to carefully specify the location of the threat.

According to the result of the analysis, if the interrogated item is an innocent article it is routed to a PASS conveyer 253 which directs the innocent item to the plane loading zone. In case item is realized to be a threat, an audio alarm system 62, connected to the diffraction station 200, is sounded and a HOLD conveyer 254 directs the threat to a holding area 3. The bar code of the threat is read by the bar-code reader 255, and the threat is checked by the radiographic imaging unit 100, as the threat is moved to the holding area for either apprehension, or further analysis, or manual inspection.

The unattended explosive detection system using x-ray action analysis with four tubes pictured in FIG. 5 may be used. In this case it is unlikely to deliver any dose to any individual including the operator. In case of interference by an operator as in the system shown in FIG. 38, the operator is expected to be exposed to a dose level much less than that received from a dental x-ray and the dose limit will be well below the recommended level for the general population. The main radiation dose will be to the cargo. However, that exposure will not adversely affect the content of the cargo or the container. Since the x-ray source consists of a relatively small collimated beam which is collected by a beam stop on the opposite side of the sample, the potential radiation hazard to individuals will arise largely from radiation scattered from the baggage. The system includes proper shielding for this scattered radiation to limit the exposure of the operators to less than 72 mrem/year. The cargo exposure would result in an estimated exposure of 36 Roentgens/sec. For a baggage/cargo item of length 1 m, traveling on the conveyor at 0.2 m/sec, the total exposure would thus be 180 Roentgens. This is not expected to cause any adverse effects on the cargo. Since most of the x-ray beam is transmitted, the actual absorbed dosage would be much less, depending on the density of the cargo and the absorbing materials present.

Figure 39:
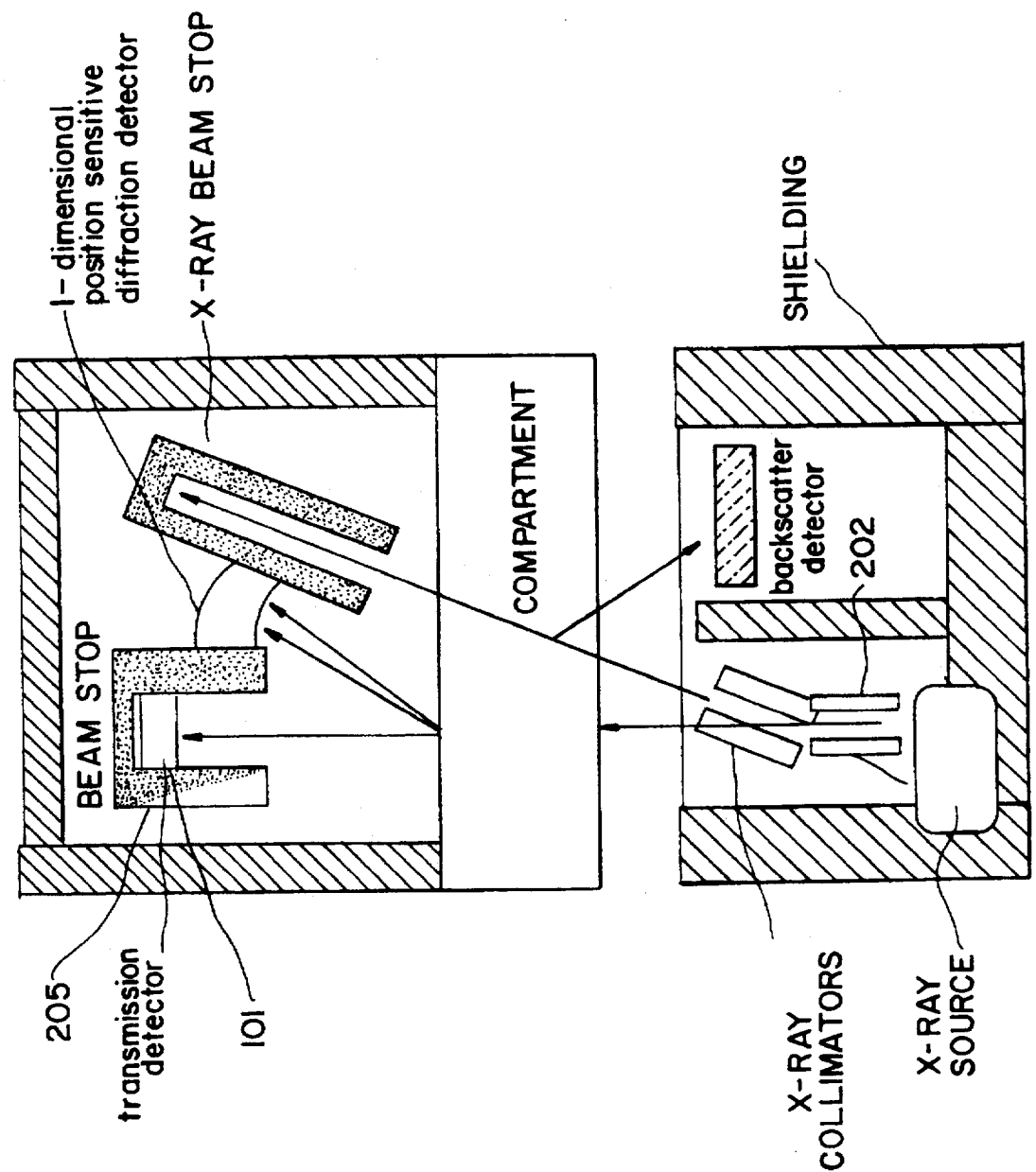
FIG. 39 is a schematic of the portable probe for drug detection in concealed environment and in open environment aboard vessels.

In another embodiment of the present invention, a portable drug detector is disclosed for inspection of open environment and concealed compartments aboard vessels. In the open environment, the systems disclosed for contraband detection in carry-on baggage and dense baggage can be used. For both open environment and concealed compartments the portable probe is comprised of two adjustable components as shown in FIG. 39. The system can be adjusted to operate in the transmission, diffraction or backscatter mode or as a combination of each mode. The probe is a fully automated x-ray analysis unit for detailed interrogation of concealed compartments. Should the analysis show positive identification of a drug or an object that raises suspicion, because of drug content, an alarm will be sounded automatically to alert the operator to take the necessary subsequent action which may include opening the compartment and manual inspection, seizure, and apprehension. The item will otherwise pass the checking process. For analysis, a laptop computer may be used. The probe is designed such that it will pose no hazard to the user or to persons in the vicinity and will not affect any changes in the content of a concealed compartment.

Standard x-ray radiographic imaging, and x-ray diffraction are appropriate wherever x-rays transmission is feasible, such as in the case of compartments accessible from both sides. In this case, the arrangement of the portable detector will be as shown in FIG. 4 which allows the detection of transmitted images or diffracted patterns by the use of collimator 202 and the beam stop 205. A detector 101 for transmitted images is enclosed within the beam stop 205, as shown in FIG. 39. The x-ray backscatter imaging is applicable for configurations which can be interrogated only from one side, such as floors. The arrangement in this case will be as shown in FIG. 18.

Radiographic imaging is appropriate for scanning of thin, small, low density concealed compartments. Suspicious compartments can then be searched manually or can be screened further by the x-ray diffraction capability for finer spot inspection to confirm the suspicion prior to opening for manual search. In case of dense medium, x-ray backscatter imaging is appropriate for general interrogation while x-ray diffraction is adequate for detailed analysis. Alternatively, x-ray diffraction can be used directly on suspected concealments, if time allows. For documentation, a radiographic imaging mode may be also used. The selection of any combination of these modes is appropriate to maximize the utility of the probe while reducing the misses as well as the false alarms.

The difference between the drug density and background material in the concealed compartment (clothing, personal articles, stored material, etc.) density will lead to different intensities of backscattering of the x-rays incident on the barriers of the compartments. The variation in the intensity of the backscatter also reflects the non-homogenity of the materials in the backscattering media. X-rays are appropriate for detection of drugs due to their relatively short wavelength; provided that sources with sufficient intensity are used, for the rays to penetrate the barriers to desired depths. The absorption in the barriers is determined by the heaviest element content. The detection of hidden objects in an interrogated area is based upon the difference in penetration depths. Scattering of incident x-rays depends on the material present and the atomic number of the constituting elements. If displayed as an image on a screen (CRT), the intensity of the backscatter will show dark and/or bright patterns with different degrees of brightness (gray scales or colors). Those patterns identify concealed objects. The differences both in the shape of the image and in the intensity leads to differentiation between concealed drugs and other objects.

X-ray images of various drugs hidden in representative compartment barriers aboard marine vessels need to be stored on the computer for reference comparison. In the x-ray diffraction, interrogation patterns would be collected by computer-assisted surveillance of localized spots throughout the concealed compartment contents and compared with the powder patterns of cocaine and heroin. Since each crystalline chemical compound has a unique x-ray powder pattern, the patterns of cocaine and heroin can be rapidly compared with the observed spectrum. The x-ray pattern consists of a series of lines at fixed scattering angle (for a given wavelength) and fixed intensity. The widths of the lines may vary slightly with differences in microcrystalline particle size. When several different substances are present in the x-ray beam, their spectra will be superimposed in the observed pattern, but they can usually and easily be resolved by well known pattern matching and subtraction techniques, yielding in addition, the relative amounts of each substance. The computer will add stored (known) patterns to get best fit to the observed pattern, giving relative percentage of each kind of drug.

Particulars of x-ray action which are important in discrimination between drugs and the look-alike objects include: patterns for crystalline nylon, wool, and other fabrics which show only a few weak lines and amorphous scattering at low angles and which can probably be ignored, or alternatively stored in the computer memory and subtracted from the spectrum. Also, concealment with water-based material will show characteristic powder patterns when drugs or undissolved additives are present. X-ray powder patterns from drugs or undissolved matter (if present as in slurry) can also be used for recognition of water-based explosive systems and for differentiation from other liquids [water-based objects which may be used to conceal drugs have the unique properties of higher-density [1.1–1.4 $g/cm^3$) and the liquid-air interface is not horizontal]. Thin layers of drugs should be relatively easy to detect in a diffraction system, as opposed to a radiographic imaging system, since the powder pattern is collected over a relatively large area. Drug layers show the characteristic x-ray powder pattern of cocaine or heroin crystallites. [Layer drugs have higher density (1.4–1.55 $g/cm^3$) compared with paper, fabric, and similar shaped materials which have substantially lower densities (0.7–1.2 $g/cm^3$)].

When x-ray diffraction is used for the analysis, the scattered x-rays have the same energy as the probe beam. Thus, highly penetrating short wave-length x-rays may be used to probe highly absorbing materials. In addition, since each chemical compound has a characteristic pattern, not only are all elements detected, but the actual chemical compounds can be identified. The problem thus becomes one of obtaining an adequate signal to noise ratio.

A hand-held, dual-energy x-ray backscatter imaging system is set forth herein for buried mine detection in rough terrain. X-rays are appropriate for detection of land mines due to their relatively short wavelength; provided that sources with sufficient intensity are used, for the rays to penetrate the soil to desired depths. The absorption in the soil is determined by the heaviest element content; which is mostly iron (about 7% $Fe_2O_3$) except in sands wherein silica is the dominant factor. However; in black sands the presence of zirconium may enhance the absorption. The detection of objects in an interrogated area is based upon the difference in penetration depths. Scattering of incident x-rays depends on the material present and the atomic number of the constituting elements. If displayed as an image on a screen (CRT), the intensity of the backscatter will show dark and/or bright patterns with different degrees of brightness (gray scales or colors). Those patterns identify buried mines whether being a mine with plastic casing or a mine with a metallic casing. The difference both in the shape of the image and in the intensity leads to differentiation between mines and other buried objects, such as a piece of wood, a rock, a metallic fragment, etc. In case of a piece of wood, for example, a higher intensity of the backscatter will result because of the low density, and the shape of the object can also be distinguished. Switching between two applied high voltages will change the energy distribution of the x-rays produced, resulting in improved contrast in the imaging of buried objects. Use of multiple energies may further enhance the backscatter imaging and assist in discrimination between objects in some situations.

Figure 40:
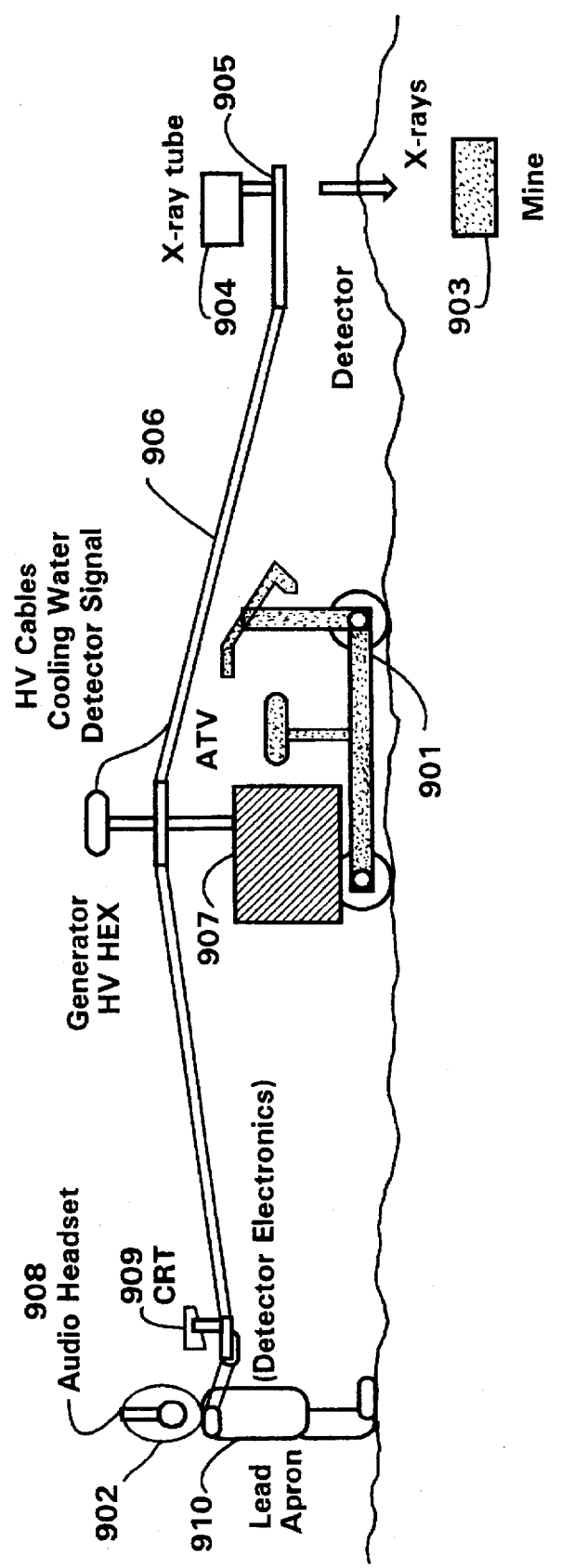
FIG. 40 is a schematic sketch of a hand-held antipersonnel mine detector.

The detector is to be mounted on an all terrain vehicle (ATV) 901, as shown in the arrangement of FIG. 40, remotely controlled by an operator 902, moving slowly and cautiously, interrogating a foot path. The arrangement of the integrated system is selected to increase the standoff position of the operator 902 by using the ATV 901 as a barrier between him and the mine 903 and the x-ray backscatter.

The x-rays source 904 consists of a 20 kW rotating anode x-ray generator that switches between two x-ray energies at a rate of 60 switches/sec. The x-rays produced will be collimated into a 2 cm diameter beam. The collimator sweeps across an area of 60 cm at a rate of 1 sweep/sec. At this rate, a forward speed of 120 cm/min will be achieved. The detector 905 comprises four scintillation detectors with an area of 20 $cm^2$ each, and displaced at differing heights will provide additional compensation for surface roughness. Both the source and detectors will be located approximately 30 cm above the surface. To reduce weight, only the anode and detectors are located on the probe boom 906. The power source, x-ray generator, and electronics 907 are located on the ATV. The detector electronics 911 are located on the handle of the system. Since the 60 cm sweep area would likely be insufficient for an ATV, it may be necessary for the operator to sweep the probe from side to side to clear a larger path or two rotating anodes may be used.

The difference in the counting rate which would appear in the presence of a mine may be used to sound an audio alarm signal or initiate a warning signal in the headset 908. For verification, the output of the detector is transmitted to a video display 909, coupled with the forward motion of the operator 902 to produce a two dimensional image of the backscattering from the object.

Means to protect the operators from the ionizing radiation is provided through the ATV barrier and a lead apron 910 without affecting the progress of the operator. Also a standoff arrangement is used to minimize exposure of the operator. Such arrangement is necessary to avoid lethal mine engagement and to minimize the distance between the source and the target.

Figure 41:
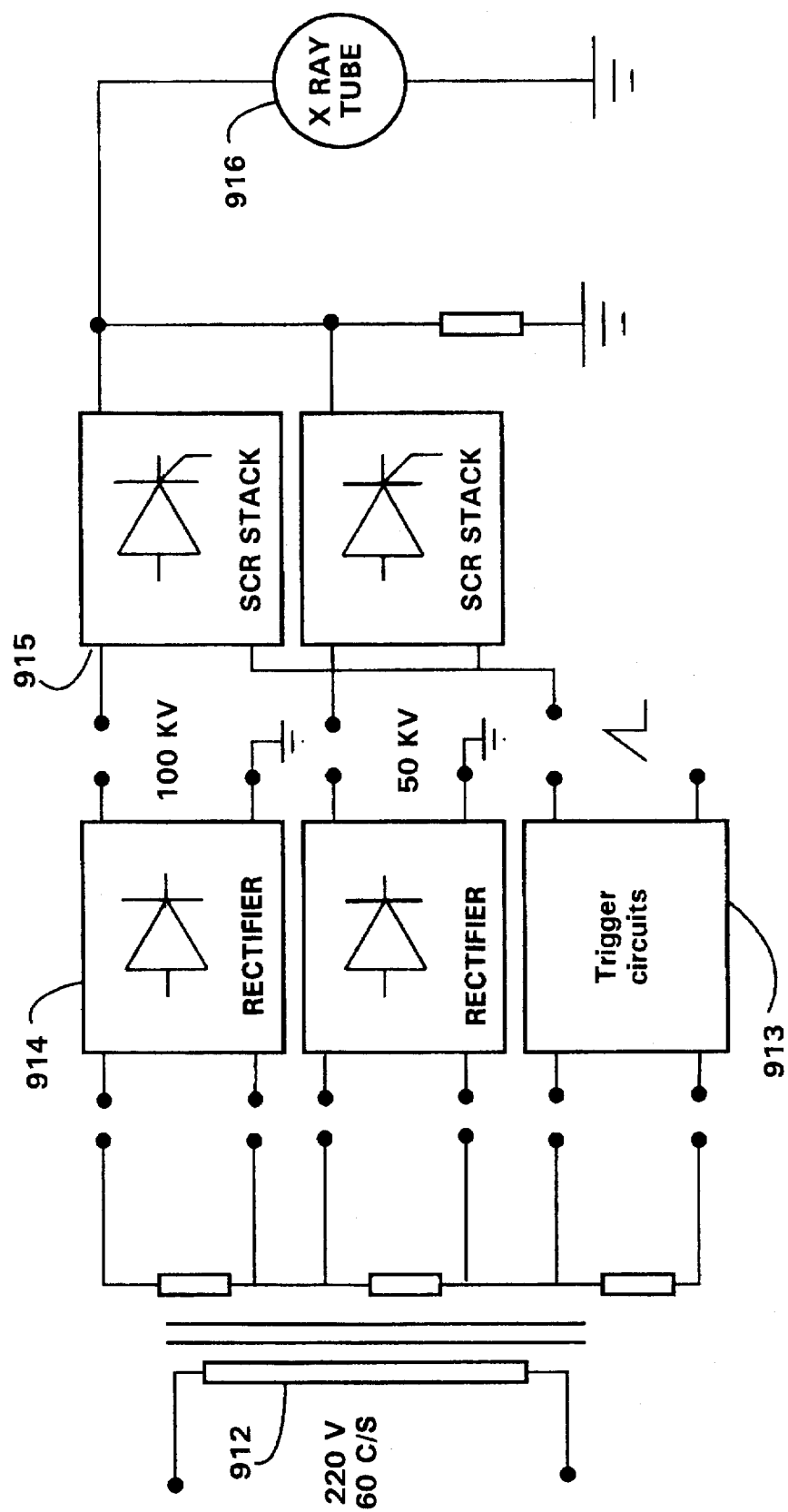
FIG. 41 is a circuit diagram of the switching circuit for the detector of FIG. 40.

The switching is accomplished by the simple circuit shown in FIG. 41 which includes the transformer 912, the trigger circuit 913, and two thyristors, such as silicon controlled rectifiers (SCRs) 914. The switching is programmed using an exclusive or logic such that the thyristors (SCR 1 and SCR 2) 915 are switched alternately to allow operation of each tube 916 at 50 keV and 100 keV. The integrated functional block diagram of the x-ray production system of the detector is as shown in FIG. 23 and the detection and image processing system is as shown in FIG. 24.

The field of interrogation of the x-ray backscattering detector involves a lateral extent of 120 cm, a path width of 60 cm/single pass/tube, a forward speed of 0.02 m/s (0.79 in/s) and a spot size of 3.14 $cm^2$. The total x-ray power is 20 kW, the duty cycle is 100% per tube, the average power is 20 kW/tube, the peak power is 20 kW/tube, the pulse duration is 16.7 microseconds, the instantaneous electron current is 200 mA, the voltage is 50 kV (low energy) and 100 kV (high energy), and the switching rate 60/s (alternate pixels) and 1 per second (alternate scan lines). Two (2) rotating anodes are used with a clearance to the face of the collimator of 30 cm and a focussed electron beam of 2 cm diameter. The major components are: an AC power supply, a high voltage supply, switching and power conditioning control electronics, x-rays source, a detector and oscillating collimator; signal processor, image processor and enhancer, analog-to-digital converter (ADC); CRT (LCD) for display imaging, and an audio alarm (earphones); cooling system; ATV carrier with a boom; ATV controls and x-ray system controls; lead apron and HV insulation; and a microprocessor.

The operation by the operator involves: driving the ATV; maintaining the proper elevation of the boom to assure proper distance between the detector and the face of the ground, especially in case of terrain irregularities or surface roughness; using an audio signal of different tune than the detection signal as well as a flashing amber light as means to alert the operator of improper clearance of the detector head from the ground; sweeping forward (or laterally); listening attentively to the headset to seize movement in case an alarm signal is received or should a change in the audio be sensed; and looking at the CRT screen to identify the image and intensity when receiving an audio alarm. Audio signals are the primary (initial) indicator. Changes in the audio signal will alert the operator to the possibility of locating a mine. Checking of the display will be mainly for verification of the identity of the hidden object.

The preferred embodiment is based on lateral scan while the operator would progress forward after each scan. The oscillating collimator is driven by a motor and is allowed to laterally swing around a pivot through an angle not to exceed 45°. An alternative embodiment is to allow the operator to sweep laterally whereas the collimator oscillates back and forth along the motion of the operator. The later embodiment may have a safety merit of providing the operator with a high level of confidence in his forward motion.

Discrimination between non-metallic mines, metallic mines and other buried objects was verified experimentally both by the backscattering intensity and the image appearing on the CRT. The detector capability can differentiate between the soil, a void in the soil (or a loose noncompacted region), a piece of wood and a mine due to the higher intensity of the backscattering detected from the wood (because of the low density) as well as the shape of the object. The detector is also capable of discrimination between mines with metallic casings and pieces of metallic debris, such as shells.

By computer simulation the required characteristics of the x-ray source and detector system were determined to design a realistic experiment. In order to calculate the expected x-ray backscattering from a buried mine, a computer program was written to estimate the penetration, absorption, and backscattering of the x-rays in the soil. A number of assumptions were made in order to simplify the calculations. The incident beam is assumed to enter the soil vertically. The penetration of an inclined beam would be reduced by a factor of sin e, where e is the angle of the beam with respect to the surface. The incident beam is collimated and only single Compton scattering events were considered. The incident beam is assumed to be monochromatic. A real system would include a distribution of x-ray energies for any potential applied to the tube. Compton scattering is assumed to occur with equal probability in all directions. In fact, measurements as a function of angle show somewhat higher probabilities for the forward and 180. (backscattering directions, and lower probability at intermediate angles). At the energies required for sufficient penetration, the expression for scattering reduces to that of a free electron. As a result, the scattering becomes a function of only the number of electrons per unit volume (density). This can be rapidly calculated using an approximation due to Compton, $$1/I_o = (8\pi/3)(e^4/mc^2)[1/(1+2\alpha)]$$

where $\alpha = h\nu/(mc^2)$.

For a backscattered photon to be detected, it must penetrate the covering of soil from the point of scattering to the surface. It is therefore necessary to include the effects of absorption by the soil on both the incident and scattered beams. This is done by numerical integration. The path of the x-rays through the soil (and mine) is divided into elements of 1 mm thickness. Starting with an incident beam of known intensity $I_o$ at the surface, the intensity in the next lower integration element is calculated by $$I_{o,n+1} = (I_{o,n} - I_{s,n})A_n$$

where $I_{s,n}$ is the amount lost by Compton scattering in the $n^{th}$ element and $A_n$ is the factor describing intensity loss by other absorption processes. These are calculated from the Compton approximation, an assumed density of the $n^{th}$ element, and the linear absorption coefficient. This calculation is carried to a sufficient depth (1 meter) such that the beam is completely absorbed.

For a backscattered photon to be detected, it must also be scattered in a direction where it will strike the detector. If the scattering from a particular element of the soil is equally probable in all directions, then only a fraction of the scattered photons will be detected. Given by the ratio of the detector surface area to the area of a sphere with radius corresponding to the distance between the point of scattering and the detector, $$D_n = \pi r_d^2 / (4\pi r_n^2).$$

To calculate the total backscattering intensity reaching the detector, the scattering is summed starting from the deepest element, $$I_{BS,n} = I_{BS,n-1}A_n + I_{s,n} \times D_n.$$

Here $I_{BS,n}$ is the total backscattering intensity due to scattering from the $n^{th}$ element and all lower elements.

A mine is simulated by filling an array corresponding to the points of integration with values of the density corresponding to the shape and composition of the mine. For the simulation plotted in FIG. 42, the mine was assumed to have a density of 1.7 g/cm³ and to be enclosed in a metal casing of density 4.0 g/cm³. The mine was assumed to be buried in soil with density 2.4 g/cm³ with the top of the mine 8.5 cm from the surface. To simulate the effects of rocks and other objects in the soil, a random number generator was used to vary the soil density in each integration element over a range of 10%.

Figure 42:
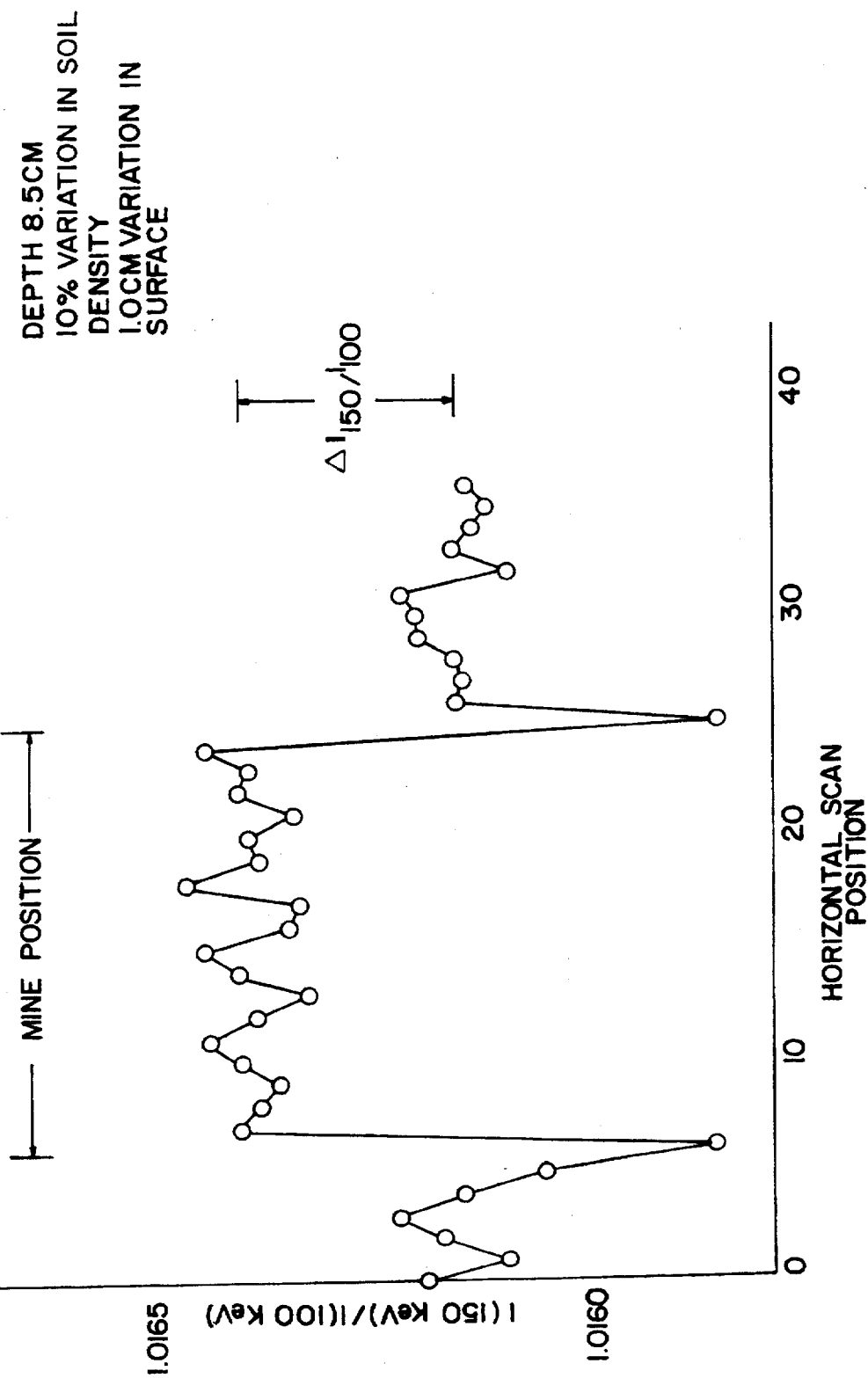
FIG. 42 is a plot the relationship between the ratio of signal intensity at 150 keV and the signal intensity at 100 keV, and the horizontal scan in centimeters at burial depth of 8.5 centimeter for 10% variation in soil density and 1 centimeter variation in surface irregularity.

A significant difficulty with the interpretation of the backscattering intensity is the influence of variations in the soil surface. To simulate a variation in the surface, a random number generator was used to produce surface variations over a range of 1.0 cm. The fluctuation in the signal observed in FIG. 42 is almost entirely due this surface variation. The fact that the simulation reproduces this effect is further evidence for the validity of the calculations. One technique for compensating for surface variation is to use two or more x-ray energies. This is included in the simulation by calculating the spectrum at each point with different wavelengths. In FIG. 42, the two energies chosen were 150 KeV and 100 KeV. The signal is then plotted as the ration of the scattering at the two energies.

The sensitivity of the backscattering to factors such as variations in soil density and composition, and surface roughness were examined experimentally. The assumptions made in the simulation of the mine detection capability mainly involved the use of a collimated source to effectively limit the backscatter to single Compton scattering events. A disarmed buried mine was used with composition and dimensions of a typical mine such as the nonmetallic M14 antipersonnel mine. The source and detector were located approximately 30 cm from the soil surface. The detector had an effective surface area of 80 cm². The source was switched between two energies in the range between 50 and 100 keV. The x-rays were produced from a 20 kW generator and rotating anode. Factors including the variation to soil density and especially the surface height variation were taken into account. The mine was buried 10 cm or more below the surface.

Figure 43:
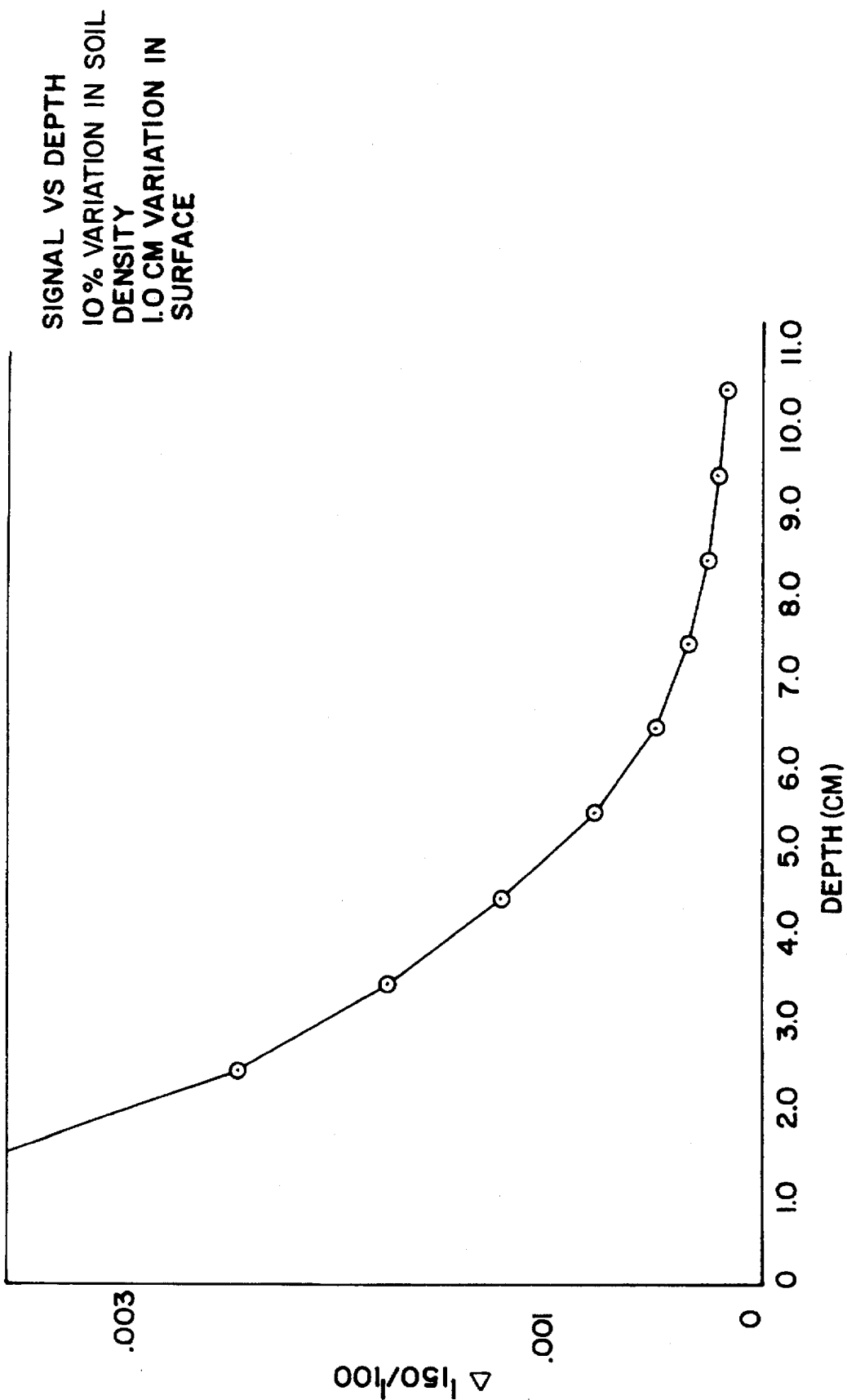
FIG. 43 is a graph showing a plot of the signal against the burial depth in centimeters, for 10% variation in soil density and 1 centimeter variation in surface irregularity.
Figure 44:
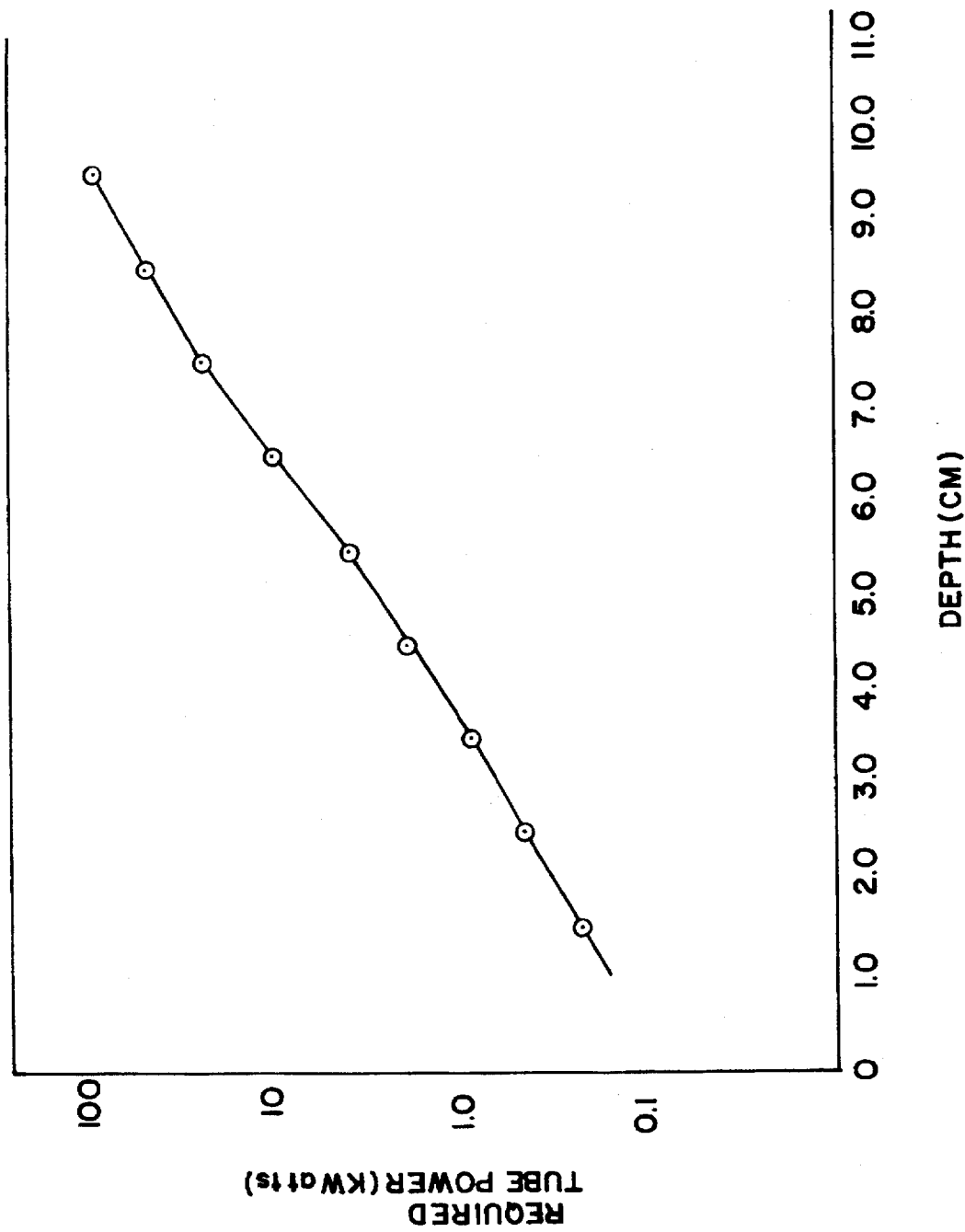
FIG. 44 is graph of the required x-ray tube power versus the burial depth.
Figure 45:
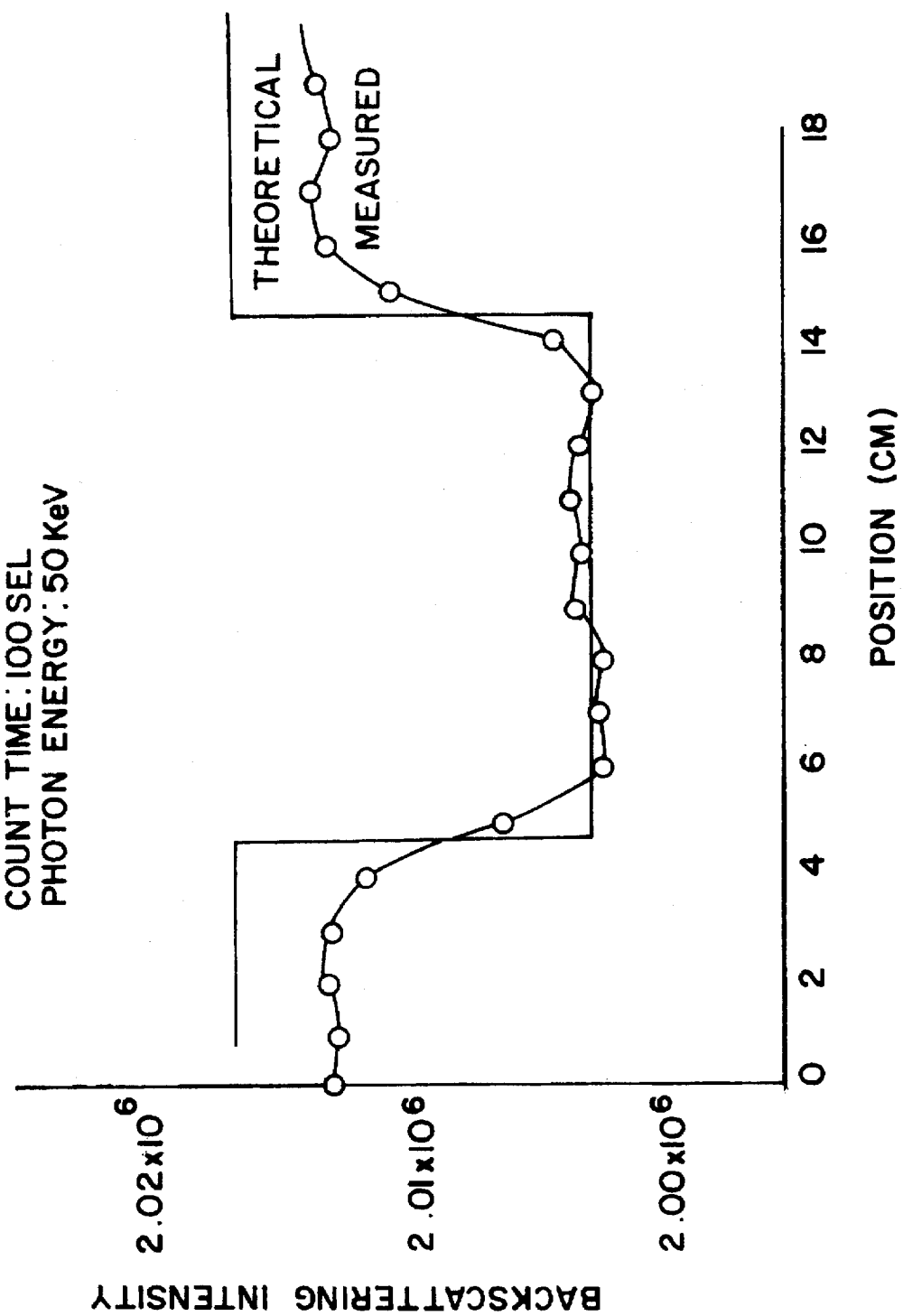
FIG. 45 is a plot of the variation in the backscattering intensity as function of the scanning position relative to mine location.

The x-rays produced had sufficient backscatter intensity to yield a signal above background for the buried mine. Effects of variation to soil density and especially surface height variation were not influenced by the beam intensity, hence there is little value in using a larger x-ray generator. The plot given in FIG. 42 is of the signal (ratio of intensity at 50 KeV and 100 keV) versus the horizontal scan position for an 8.5 cm depth. In FIG. 43, the signal is plotted against the depth. Both graphs are for 10% variation in soil density and 1.0 cm variation in surface. The required tube power in KW is plotted against the depth in cm in FIG. 44. The results of a typical scan are plotted in FIG. 45. The curve predicted on the basis of the theoretical calculations has been scaled to fit the experimental scattering at the mine position.

Figure 46:
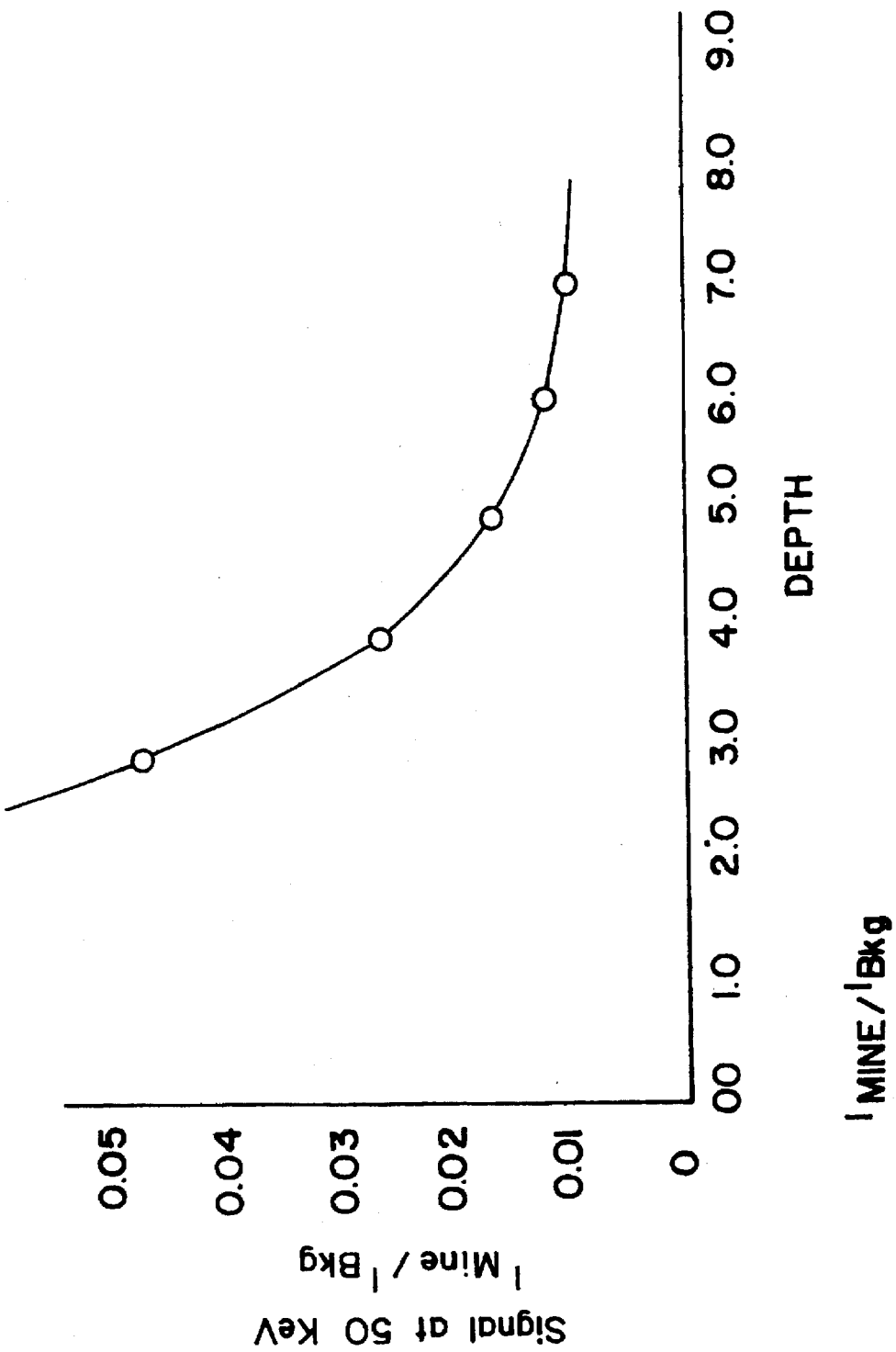
FIG. 46 is a graph of the ratio of the signal intensity from the mine to the background intensity versus burial depth at 50 KeV.

The absolute count rate at this position is about 15% of the calculated value. The predicted signal (difference between the scattering at the mine position and background), however, agrees with the calculation to within about 25%. This is reasonably good agreement considering the uncertainties associated with the scattering process such as the contribution from multiple scattering, variations in the density of the sample, etc. (Note that absolute intensity is used here in contrast to ratios of intensities used in FIG. 42). Fluctuations in the signal with position are most likely a result of variations in the density of the sample and some contribution from long range variations in the source, rather than statistical variations in the signal counts. The change in the signal with depth is shown in FIG. 46.

High detection/false signal ratios can be achieved by use of redundant means of annunciation through a headset, an image and intensity differentiation. For mines on the surface or buried at relatively small depths, the power requirements are such that the weight can be supported by the ATV. Also, either rechargeable batteries, or ac power supplies can be used. Light power supplies appropriate for the application are readily available as off-the-shelf items. The use of rotating anodes reduces the number of x-ray tubes required for scanning by one-half since each tube is capable of producing two consecutive beams with two different wavelengths. By displacing the detectors, compensation to surface roughness and terrain irregularities was possible. The variation in the heights of the detectors allows triangulation on source of scattering. The switching is achieved for a pulse duration of 1/60 seconds by a simple switching circuit.

Figure 47:
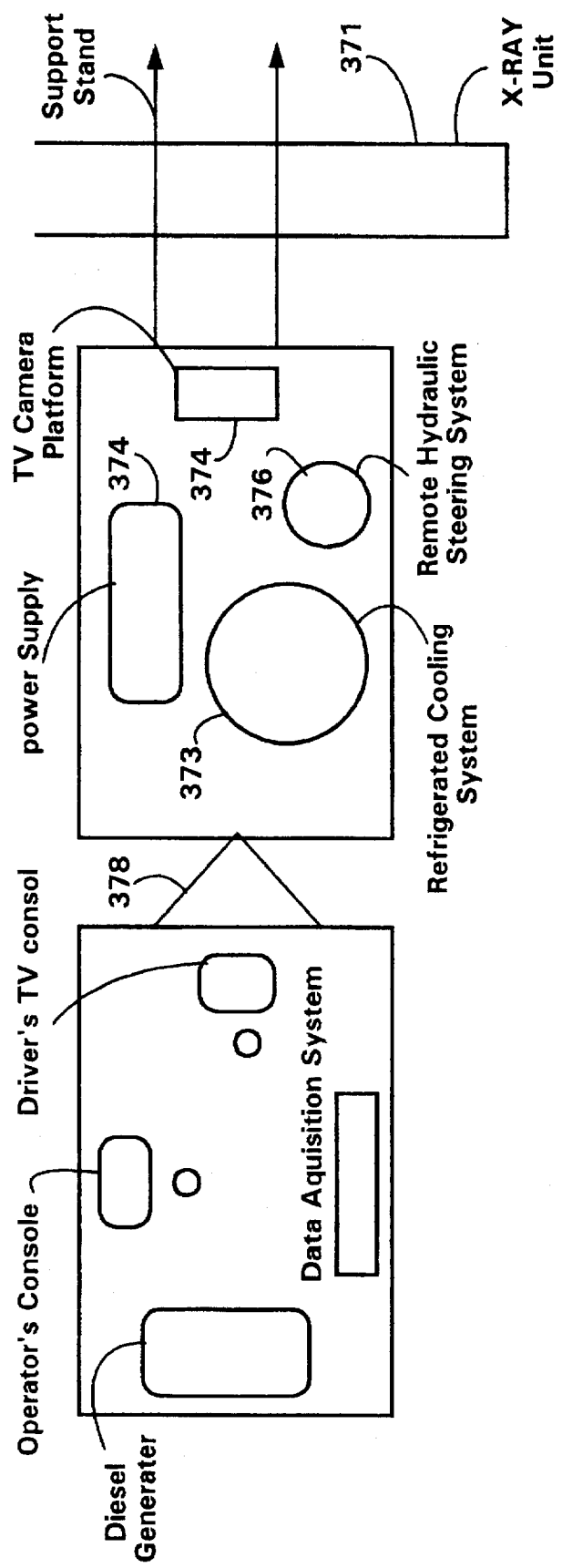
FIG. 47 is a top view of the mounting arrangement of a detection system for antivehicle and anti-aircraft mines.
Figure 48:
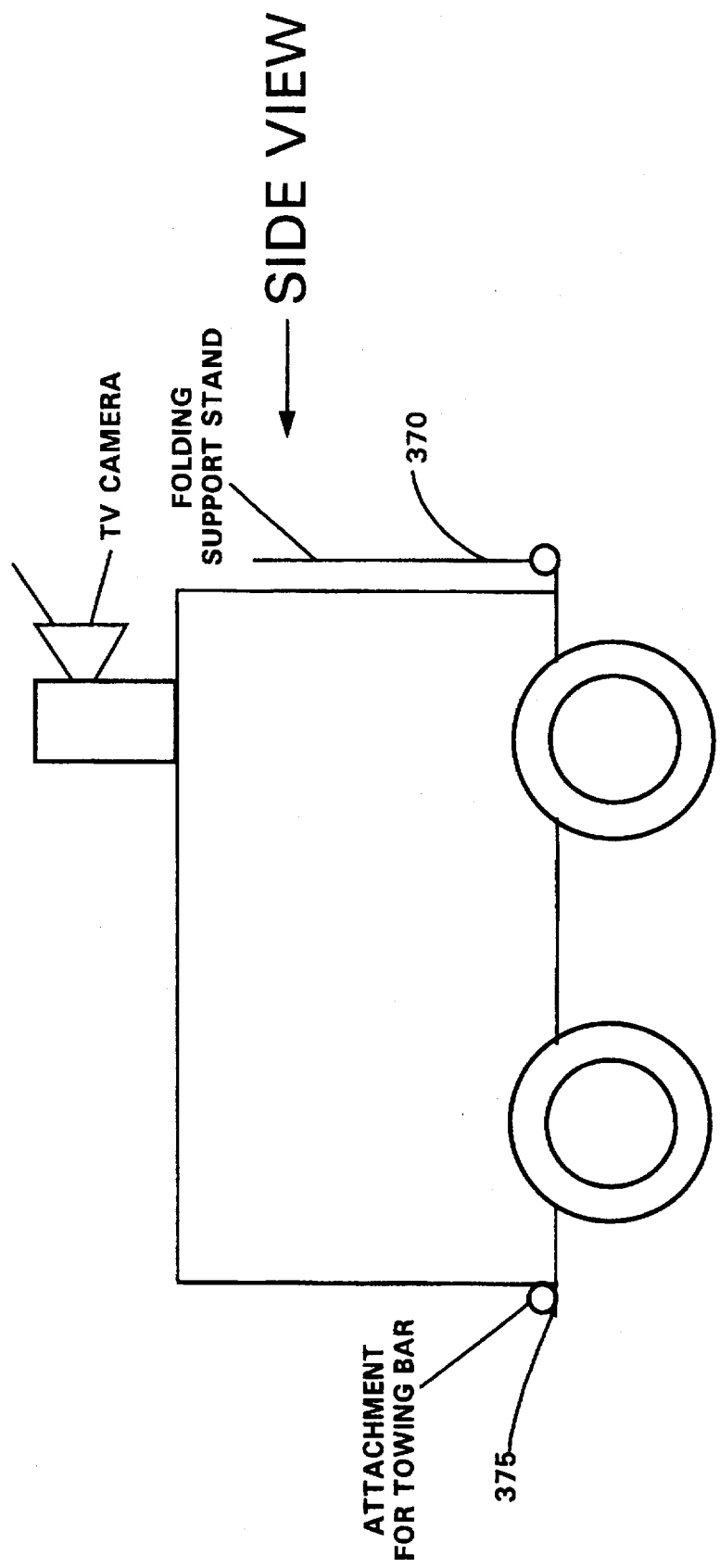
FIG. 48 is a side view of the mounting arrangement of the detection system of FIG. 47.

An x-ray backscattering system similar to that designed for dense baggage as shown in FIG. 18 may be used for detection of antivehicle and anti-aircraft buried mines. The switching system will be as shown in FIGS. 91, 33 and 34. A top view of the mounting system is shown in FIG. 47. The front vehicle is remotely operated and has an extended folding support stand 370 carrying the x-ray unit 371. The vehicle carries the power supply 372, the cooling system 373 and the TV camera platform 374 on which the TV camera 375 is mounted, and the remote hydraulic steering system 376. At the rear of the vehicle an attachment 377 is located for the towing bar 378. The driver console 379 and the operator console 380 are located on the towed vehicle for standoff protection from radiation and possible engagement of a mine. On the rear vehicle the heavy diesel generator 381 and the data acquisition systems are mounted. A side view of the mounting arrangement is shown in FIG. 48.

The source of the detector is mounted on a vehicle of speed 1.34 meters per second (3 miles per hour) interrogating an area of 3 meters width. The x-ray system contains 120 tubes successively fired one after the other to supply a peak power of 100 kW for a pulse duration of 100 microseconds. Switching tubes between two high voltage pulses (120 kV and 160 kV of 1,000 mA) occurs for alternate pixels, implying a switch rate of 4,500 per second. X-rays are collimated to produce an illuminated spot on the ground of about 2 cm in diameter.

A large scintillation single crystal detector, NaI(Tl) will be used. The output of the NaI(Tl) detector is mapped into the memory of a microcomputer and fed to a visual display unit giving an image of the interrogated area to identify the location of the targets. Also, an audio signal is produced via a headset to alert the operator to the presence of a mine. The field of interrogation is 3 meters lateral extent and a line scan of 15 milliseconds/sequence.

In the embodiment of the redundant standoff detection capability a combination of prompt gamma detector and x-ray backscatter imaging is used. A gas chromatography may also be used in addition or in place of the backscattering unit should data become available on gases/decomposition by products diffusion from soil (types of soils to include clay, sand, and mixtures of both), and on sensitivity and linear range of suggested detectors for various gases and decomposition byproducts of explosives used in ordnance such as HMX and RDX.

Figure 49:
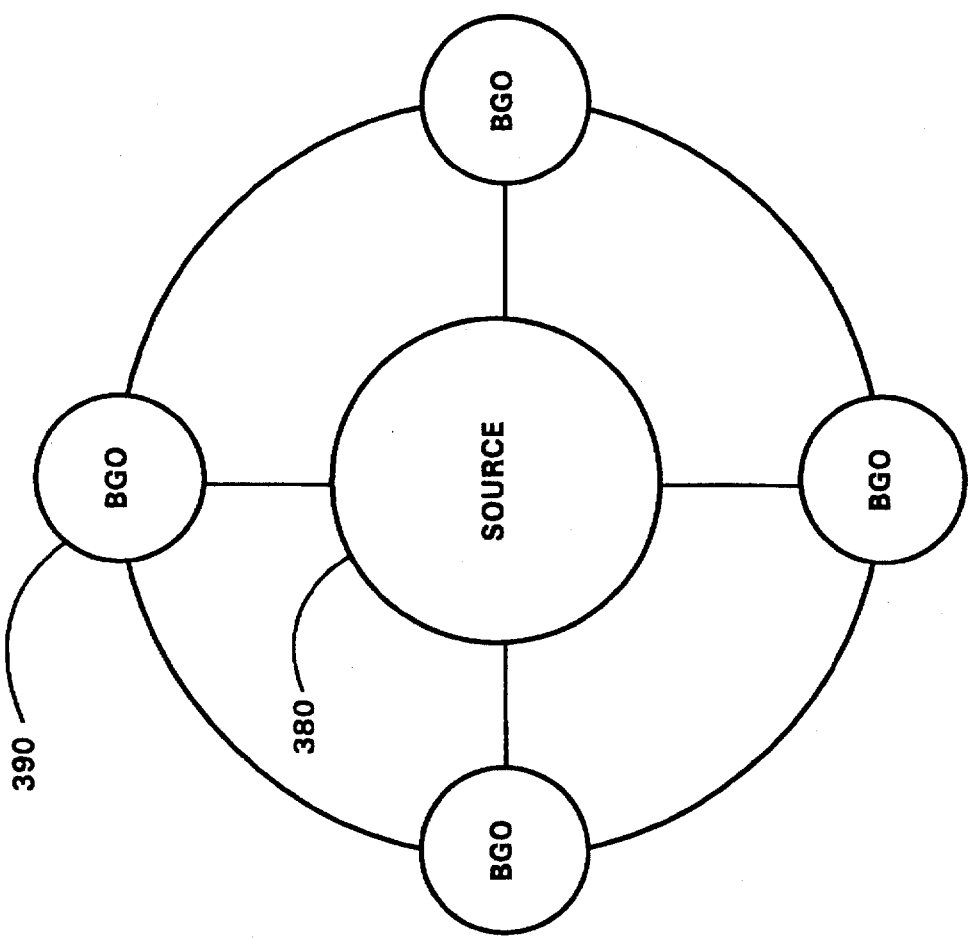
FIG. 49 is a schematic of the arrangement of the neutron source and the detectors for the prompt gamma system for detection of antivehicle and anti-aircraft mines.

The prompt gamma detector utilizes a 10 kHz repetition-rate deuterium-tritium neutron generator, such as that developed at Sandia National Laboratories, to deliver $10^3$ to $10^4$ neutrons per pulse. More than 90% of the neutrons are emitted during a time window that is 10 microsecond wide, and which starts 3 microseconds after the trigger pulse. The core of the system shown in FIG. 49 is a small-size neutron source such as the Zetatron Neutron Tube (assembled by General Electric) and consists of an ion source, an ion accelerator, and a metal target loaded with deuterium and tritium. A mixture of deuterium and tritium ions is accelerated at 25 to 60 keV into the target, to produce 14.1 MeV neutrons and 3.49 MeV alphas. The excited levels of $^{14}N$ at 2.313 MeV (0+), 3.948 MeV (1+) and 6.444 MeV (3+) are most easily excited (populated). For carbon, oxygen, silicon, calcium, and iron, the most easily excited states lie at 4.439, 6.049, 1.779, 3.352, and 0.847 MeV respectively. These states have very short life times and hence detection of the de-excitation gamma rays must be done during the 10 microsecond neutron pulse.

The source-detector configuration is shown in FIG. 49. The Zetatron 380 is located at the center, and four 15.2×15.2 cylindrical Bismuth Germanate (BGO) detectors 390 are located on the periphery of the system. The detectors are shielded with lead and boron are used for event counting. The BGO detector is preferred over the NaI(Tl) device because it has a much higher efficiency for high energy gamma-rays and has efficiencies of 10% to 20% for gamma-ray energies ranging from 2 to 8 MeV.

The activation (prompt or otherwise) of a material and its subsequent de-excitation or radiation can be calculated using the following relationship:

$$N(g/sec) = N_t \times \Phi \times \sigma,$$

where $N_t$ in atoms/cm² is the number of target atoms per centimeter square, $\Phi$ in neutron/sec is the neutron fluence, and $\sigma$ in cm² is the cross section for the reaction. The (n,n') inelastic cross-section is approximately constant and is approximately $5 \times 10^{-25}$ cm² for the target nuclei for the most commonly used military explosives, according to their nitrogen content and densities. Nitrogen is uniquely identified with high explosives, and is readily identified in soil/water environments when buried to a depth of three feet. Nitrogen contents for most primary and secondary explosives range from 10 to 40 percent conservatively an average volume of 30% may be used in the calculations for nitrogen content in explosives.

Considering typical explosive loads of one to ten kilograms, a one kilogram explosive is assumed to be buried at surface to 1 foot below surface, ten kilograms of explosives are also assumed to be buried at depth of 1 foot. To examine the capability of detection, several assumptions are made. The neutron generator operates at 10 kHz, and produces $10^7$ n/sec, with the neutrons having an isotropic distribution. The neutron generator is placed at a height of 50 cm above target surface, the target density is 1.6 g/cm$^3$, and its nitrogen content is 30%, and one kilogram explosive load is contained in a 6 in diameter package. Accordingly, the activation rate N(g/sec)=18,720 g/sec. For a gamma-ray source emits radiation isotropically the gamma-ray intensity varies inversely with the square of the distance. The detector efficiency may be taken as 15%, and a soil attenuation factor ranging from 44 to 97% at depths of 5 cm to 30 cm, respectively. The total reduced signal return taking into account the isotropic neutron fluence, depth of target, isotropic gamma-ray distribution and efficiency, and attenuation of neutrons and gamma-rays combine to yield values of: $3.48 \times 10^{-3}$ at the Surface, $2.36 \times 10^{-3}$ at 5 cm depth, $1.65 \times 10^{-3}$ at 10 cm depth $1.14 \times 10^{-3}$ at a depth of 15 cm, $8.27 \times 10^{-4}$ at a depth of 20 cm, $5.88 \times 10^{-4}$ at a 25 cm depth, and $4.39 \times 10^{-4}$ at 30 cm depth. This provides a range of return signal values ranging from 8 to 65 measured gamma-rays per second above any background for the positive detection of explosives within the assumptions made. That is, if a 10 kg explosive device were placed at the surface, we would measure 650 g/sec.

The entire assembly may be assembled and supported by a 10 meter-long boom, and allowed to sweep a 180×arc in front of the carrying vehicle. For a total area of 3.14 m$^2$, and based on velocities of 2 meters per 10 seconds, one would obtain coverage of rates of 1 acre in 3.6 hours. This allows for the detection of 80 to 650 events per true positive signal in the vicinity of the system (8 to 65 g/s). An order of magnitude improvement can be made by improving the operating voltage and ion source current.

The present invention relating to detection of buried antipersonnel, antivehicle and anti-aircraft mines apply to various situations other than combat. Since the mine detection system, principally the neutron activation component, detects the explosive fill within the ordnance, it can be most beneficial for bombing/gunnery range clearance and ordnance demilitarization. Actively and formerly used bombing/gunnery ranges are typically contaminated with surface and buried bomb and shell fragments making detection with a metal detector type ordnance locator impossible. Complicating the matter are volcanic soils with high iron content which render ferris metal detectors useless. Explosive Ordnance Disposal (EOD) technicians, to be successful, have to "eye ball" unexploded ordnance on the surface or turn over the surface layer of the soil to discover buried explosives. The same mine detection system configuration as the combat hand held and vehicular-mounted mine detection system is required for this application but it does not have to be as rugged.

Scrap metal, shell casings, practice bombs/ordnance removed from bombing/gunnery ranges are sometimes contaminated with undetonated/unburned explosives/propellent. Similarly, the scrap metal from demilitarized ordnance (i.e., ordnance which has the destructive components inert/removed) potentially could be sold at a premium price. However, because it could still be contaminated with explosive/propellent residue, its market value is less. Before any of the scrap material can be disposed/recycled to a scrap dealer, a check to ensure it is explosive/propellent free is required. Many times an "inert certification" is required before it can be removed from the bombing/gunnery range/ordnance demilitarization facility as non-hazardous waste. Currently, there are few scrap dealers that will recycle such scrap metal, however, the screening of this scrap is manpower intensive. Here, the invention provides an alternative to conventional methods.

While the present invention has been described with references to several embodiments, it will be appreciated by those skilled in the art that the inventions may be practiced other, vise than as specifically described herein without departing from the spirit and scope of the invention. It is, therefore, to be understood that the spirit and scope of the invention be limited only by the appended claims.

What is claimed is:

1. Apparatus for detection of buried antipersonnel land mines and explosive-filled ordnance, comprising:

a vehicle for articulatingly supporting a boom;

an x-ray generation means mounted on a first end of said boom for generating x-rays;

a detection means mounted on said first end of said boom for detecting backscattered x-rays from the earth surface and earth covered objects;

an advance control means for controlling the advancement of said boom;

an audio and visual alarm means for notifying an operator of at least the possible presence of land mines and explosive-filled ordnance mounted on a second end of said boom; and shielding means for shielding an operator;

wherein said vehicle is positioned between said first and second ends of said boom and is remotely operated by said operation.

2. Apparatus as set forth in claim 1, wherein said shielding means comprises a lead apron for the operator and the barrier provided by said vehicle.

3. Apparatus as set forth in claim 1, wherein said boom includes a platform mounted on said second end of said boom and the x-ray generator is pivotally connected to an insulated pole for mounting the high voltage cables.

4. Apparatus as set forth in claim 3, wherein said power supply and said insulated pole are mounted on said vehicle.

5. Apparatus as set forth in claim 3, wherein said insulated pole is fixed atop said vehicle and provides a center of motion of said platform.

6. Apparatus as set forth in claim 5, wherein said platform is hinged to said insulated pole to allow lateral motion.

7. Apparatus as set forth in claim 6, wherein said platform is fitted with hand controls of forward motion of said vehicle.

8. Apparatus as set forth in claim 1, wherein said x-ray generation means comprise two x-ray tubes, a high voltage generator, a power supply, a cooling system, high voltage cables, triggering and switching means, and detector electronics.

9. Apparatus as set forth in claim 8, wherein said triggering and switching means comprise rectifiers, transformers and triggering circuits.

10. Apparatus as set forth in claim 8, wherein said detector electronics include signal processing means to produce display images and audio signals.

* * * * *